US011594222B2

(12) United States Patent
Lefkofsky et al.

(10) Patent No.: US 11,594,222 B2
(45) Date of Patent: *Feb. 28, 2023

(54) COLLABORATIVE ARTIFICIAL INTELLIGENCE METHOD AND SYSTEM

(71) Applicant: Tempus Labs, Inc., Chicago, IL (US)

(72) Inventors: Eric Lefkofsky, Glencoe, IL (US); Jonathan Ozeran, Chicago, IL (US)

(73) Assignee: Tempus Labs, Inc., Chicago, IL (US)

( * ) Notice: Subject to any disclaimer, the term of this patent is extended or adjusted under 35 U.S.C. 154(b) by 61 days.

This patent is subject to a terminal disclaimer.

(21) Appl. No.: 17/387,785

(22) Filed: Jul. 28, 2021

(65) Prior Publication Data

US 2021/0358499 A1 Nov. 18, 2021

Related U.S. Application Data

(63) Continuation of application No. 16/852,138, filed on Apr. 17, 2020, now Pat. No. 11,100,933.
(Continued)

(51) Int. Cl.
*G10L 15/22* (2006.01)
*G16H 10/60* (2018.01)
(Continued)

(52) U.S. Cl.
CPC ............ *G10L 15/22* (2013.01); *G06F 3/0481* (2013.01); *G06F 3/167* (2013.01); *G06F 16/634* (2019.01);
(Continued)

(58) Field of Classification Search
CPC ........ G16H 10/60; G16H 10/40; G16H 15/00; G16H 50/70; G16H 70/60
See application file for complete search history.

(56) References Cited

U.S. PATENT DOCUMENTS 8,949,725 B1 2/2015 Goncharuk
9,275,641 B1 3/2016 Gelfenbeyn
(Continued)

FOREIGN PATENT DOCUMENTS

WO 2014134089 A1 9/2014

OTHER PUBLICATIONS

Google. Dialogflow Concepts. Analytics. Version accessed Mar. 2, 2020. Available online at https://web.archive.org/web/20200302120655if_/https://cloud.google.com/dialogflow/docs/analytics.
(Continued)

*Primary Examiner* — Joseph D Burgess
(74) *Attorney, Agent, or Firm* — Quarles & Brady LLP

(57) ABSTRACT

A method and system of audibly broadcasting responses to a user based on user queries about a specific patient molecular report, the method comprising receiving an audible query from the user to a microphone coupled to a collaboration device, identifying at least one intent associated with the audible query, identifying at least one data operation associated with the at least one intent, associating each of the at least one data operations with a first set of data presented on the molecular report, executing each of the at least one data operations on a second set of data to generate response data, generating an audible response file associated with the response data and providing the audible response file for broadcasting via a speaker coupled to the collaboration device.

30 Claims, 38 Drawing Sheets

Related U.S. Application Data

(60) Provisional application No. 62/871,667, filed on Jul. 8, 2019, provisional application No. 62/855,646, filed on May 31, 2019, provisional application No. 62/835,339, filed on Apr. 17, 2019.

(51) Int. Cl.
| | |
|---|---|
| *G16H 50/20* | (2018.01) |
| *G16H 70/60* | (2018.01) |
| *G16H 50/50* | (2018.01) |
| *G16H 40/20* | (2018.01) |
| *G06F 16/632* | (2019.01) |
| *H04B 1/3827* | (2015.01) |
| *G16H 70/20* | (2018.01) |
| *G06F 3/0481* | (2022.01) |
| *G06F 3/16* | (2006.01) |

(52) U.S. Cl.
CPC ............ *G16H 10/60* (2018.01); *G16H 40/20* (2018.01); *G16H 50/20* (2018.01); *G16H 50/50* (2018.01); *G16H 70/20* (2018.01); *G16H 70/60* (2018.01); *H04B 1/3827* (2013.01); *G10L 2015/223* (2013.01)

(56) References Cited

U.S. PATENT DOCUMENTS

| | | | |
|---|---|---|---|
| 9,369,425 | B2 | 6/2016 | Gelfenbeyn |
| 9,380,017 | B2 | 6/2016 | Gelfenbeyn |
| 9,386,113 | B1 | 7/2016 | Goncharuk |
| 9,564,149 | B2 | 2/2017 | Gelfenbeyn |
| 9,865,264 | B2 | 1/2018 | Gelfenbeyn |
| 10,026,400 | B2 | 7/2018 | Gelfenbeyn |
| 10,102,854 | B2 | 10/2018 | Gelfenbeyn |
| 10,311,492 | B2 | 6/2019 | Gelfenbeyn |
| 10,395,772 | B1 | 8/2019 | Lucas |
| 10,432,742 | B2 | 10/2019 | Gelfenbeyn |
| 10,489,112 | B1 | 11/2019 | Gelfenbeyn |
| 10,490,186 | B2 | 11/2019 | Gelfenbeyn |
| 2013/0185099 | A1* | 7/2013 | Bucur ................. G16H 10/60 705/3 |
| 2014/0372126 | A1 | 12/2014 | Ady |
| 2016/0259775 | A1 | 9/2016 | Gelfenbeyn |
| 2017/0270212 | A1 | 9/2017 | Lavrenko |
| 2018/0082022 | A1 | 3/2018 | Francois |
| 2018/0307687 | A1 | 10/2018 | Natkin |
| 2020/0126663 | A1 | 4/2020 | Lucas |
| 2020/0135303 | A1 | 4/2020 | Barber |
| 2020/0211716 | A1 | 7/2020 | Lefkofsky |
| 2020/0258601 | A1 | 8/2020 | Lau |
| 2021/0090694 | A1 | 3/2021 | Colley |

OTHER PUBLICATIONS

Google. Dialogflow Concepts. Contexts. Follow-Up intents. Version accessed Aug. 27, 2019. Available online at https://web.archive.org/web/20190827061014/https://cloud.google.com/dialogflow/docs/contexts-follow-up-intents.

Google. Dialogflow Concepts. Contexts. Input and Output Contexts. Version accessed Feb. 29, 2020. Available online at https://web.archive.org/web/20200229160125/https://cloud.google.com/dialogflow/docs/contexts-input-output.

Google. Dialogflow Concepts. Data logging and enhanced speech models. Version accessed Mar. 6, 2020. Available online at https://web.archive.org/web/20200306063247if_/https://cloud.google.com/dialogflow/docs/data-logging.

Google. Dialogflow Concepts. Entities. Developer Entities. Version accessed Dec. 13, 2019. Available online at https://web.archive.org/web/20191213040940/https://cloud.google.com/dialogflow/docs/entities-developer.

Google. Dialogflow Concepts. Entities. Session Entities. Version accessed Jan. 7, 2020. Available online at https://web.archive.org/web/20200107223242/https://cloud.google.com/dialogflow/docs/entities-session.

Google. Dialogflow Concepts. Entities. System Entities. Version accessed Mar. 6, 2020. Available online at https://web.archive.org/web/20200306114528if_/https://cloud.google.com/dialogflow/docs/entities-system.

Google. Dialogflow Concepts. Events. Custom Events. Version accessed Dec. 28, 2019. Available online at https://web.archive.org/web/20191228010950/https://cloud.google.com/dialogflow/docs/events-custom.

Google. Dialogflow Concepts. Events. Platform Events. Version accessed Jan. 31, 2020. Available online at https://web.archive.org/web/20200131184448/https://cloud.google.com/dialogflow/docs/events-platform.

Google. Dialogflow Concepts. Fulfillment. Configure Fulfillment. Version accessed Sep. 18, 2019. Available online at https://web.archive.org/web/20190918064017/https://cloud.google.com/dialogflow/docs/fulfillment-configure.

Google. Dialogflow Concepts. Fulfillment. Webhook for slot filling. Version accessed Mar. 1, 2020. Available online at https://web.archive.org/web/20200301181030/https://cloud.google.com/dialogflow/docs/fulfillment-webhook-slot-filling.

Google. Dialogflow Concepts. History. Version accessed Aug. 10, 2019. Available online at https://web.archive.org/web/20190810153616/https://cloud.google.com/dialogflow/docs/history.

Google. Dialogflow Concepts. Integrations. Dialogflow web demo. Version accessed Mar. 4, 2020. Available online at https://web.archive.org/web/20200304161437/https://cloud.google.com/dialogflow/docs/integrations/web-demo.

Google. Dialogflow Concepts. Integrations. Actions on Google and Google Assistant. Version accessed Sep. 17, 2019. Available online at https://web.archive.org/web/20190917212125/https://cloud.google.com/dialogflow/docs/integrations/aog.

Google. Dialogflow Concepts. Integrations. Facebook Messenger. Version accessed Feb. 26, 2020. Available online at https://web.archive.org/web/20200226191222/https://cloud.google.com/dialogflow/docs/integrations/facebook.

Google. Dialogflow Concepts. Integrations. Hangouts chat. Version accessed Mar. 7, 2020. Available online at https://web.archive.org/web/20200307124238/https://cloud.google.com/dialogflow/docs/integrations/hangouts.

Google. Dialogflow Concepts. Integrations. Kik. Version accessed Mar. 12, 2020. Available online at https://web.archive.org/web/20200312144256/https://cloud.google.com/dialogflow/docs/integrations/kik.

Google. Dialogflow Concepts. Integrations. LINE. Version accessed Jan. 31, 2020. Available online at https://web.archive.org/web/20200131184448/https://cloud.google.com/dialogflow/docs/integrations/line.

Google. Dialogflow Concepts. Integrations. Skype. Version accessed Jan. 31, 2020. Available online at https://web.archive.org/web/20200131184448/https://cloud.google.com/dialogflow/docs/integrations/skype.

Google. Dialogflow Concepts. Integrations. Slack. Version accessed Mar. 1, 2020. Available online at https://web.archive.org/web/20200301170516/https://cloud.google.com/dialogflow/docs/integrations/slack.

Google. Dialogflow Concepts. Integrations. Spark. Version accessed Mar. 3, 2020. Available online at https://web.archive.org/web/20200303024847/https://cloud.google.com/dialogflow/docs/integrations/spark.

Google. Dialogflow Concepts. Integrations. Telegram. Version accessed Feb. 29, 2020. Available online at https://web.archive.org/web/20200229160121/https://cloud.google.com/dialogflow/docs/integrations/telegram.

Google. Dialogflow Concepts. Integrations. Twilio programmable chat. Version accessed Mar. 18, 2020. Available online at https://web.archive.org/web/20200318193840/https://cloud.google.com/dialogflow/docs/integrations/twilio-programmable-chat.

(56) References Cited

OTHER PUBLICATIONS

Google. Dialogflow Concepts. Integrations. Twilio. Version accessed Mar. 7, 2020. Available online at https://web.archive.org/web/20200307101814/https://cloud.google.com/dialogflow/docs/integrations/twilio.

Google. Dialogflow Concepts. Integrations. Twitter. Version accessed Feb. 29, 2020. Available online at https://web.archive.org/web/20200229012147/https://cloud.google.com/dialogflow/docs/integrations/twitter.

Google. Dialogflow Concepts. Integrations. Viber. Version accessed Feb. 16, 2020. Available online at https://web.archive.org/web/20200216092456/https://cloud.google.com/dialogflow/docs/integrations/viber.

Google. Dialogflow Concepts. Intents. Actions and parameters. Version accessed Sep. 18, 2019. Available online at https://web.archive.org/web/20190918203911/https://cloud.google.com/dialogflow/docs/intents-actions-parameters.

Google. Dialogflow Concepts. Intents. Create and manage intents. Version accessed Jul. 16, 2019. Available online at https://web.archive.org/web/20190716165232/https://cloud.google.com/dialogflow/docs/intents-manage.

Google. Dialogflow Concepts. Intents. Default intents. Version accessed Feb. 29, 2020. Available online at https://web.archive.org/web/20200229160123if_/https://cloud.google.com/dialogflow/docs/intents-default.

Google. Dialogflow Concepts. Intents. Intents Overview. Version accessed Nov. 12, 2019. Available online at https://web.archive.org/web/20191112202555/https://cloud.google.com/dialogflow/docs/intents-overview.

Google. Dialogflow Concepts. Intents. Responses. Version accessed Feb. 16, 2020. Available online at https://web.archive.org/web/20200216092457if_/https://cloud.google.com/dialogflow/docs/intents-responses.

Google. Dialogflow Concepts. Intents. Rich messages. Version accessed Jan. 31, 2020. Available online at https://web.archive.org/web/20200131184448if_/https://cloud.google.com/dialogflow/docs/intents-rich-messages.

Google. Dialogflow Concepts. Intents. Training phrases. Version accessed Mar. 5, 2020. Available online at https://web.archive.org/web/20200305224120if_/https://cloud.google.com/dialogflow/docs/intents-training-phrases.

Google. Dialogflow Concepts. Project Setup and Authentication Details. Version accessed Jul. 7, 2019. Available online at https://web.archive.org/web/20190707095720/https://cloud.google.com/dialogflow/docs/setup.

Google. Dialogflow Concepts. Version accessed Dec. 24, 2019. Available online at https://web.archive.org/web/20191224213648if_/https://cloud.google.com/dialogflow/docs/concepts.

Google. Dialogflow Documentation. Version accessed Jun. 19, 2019. Available online at https://web.archive.org/web/20190619204641/https://cloud google.com/dialogflow/docs/.

Google. Dialogflow Documentation. Version accessed on Jun. 19, 2019. Available online at https://web.archive.org/web/20190619204641/https://cloud.google.com/dialogflow/docs/.

Google. Dialogflow How-To Guides Detect Intent with Audio Input File. Version accessed Mar. 3, 2020. Available online at http://web.archive.org/web/20200303170522if_/https://cloud.google.com/dialogflow/docs/detect-intent-audio.

Google. Dialogflow How-To Guides Detect Intent with Audio Input Stream. Version accessed Mar. 5, 2020. Available online at http://web.archive.org/web/20200305152006if_/https://cloud.google.com/dialogflow/docs/detect-intent-stream.

Google. Dialogflow How-To Guides Detect Intent with Audio Output. Version accessed Mar. 5, 2020. Available online at http://web.archive.org/web/20200305091303if_/https://cloud.google.com/dialogflow/docs/detect-intent-tts.

Google. Dialogflow How-To Guides Detect Intent with Sentiment Analysis. Version accessed Feb. 27, 2020. Available online at http://web.archive.org/web/20200227054455if_/https://cloud.google.com/dialogflow/docs/sentiment.

Google. Dialogflow How-To Guides Knowledge Connectors. Version accessed Mar. 4, 2020. Available online at http://web.archive.org/web/20200304161433if_/https://cloud.google.com/dialogflow/docs/knowledge-connectors.

Google. Dialogflow How-To Guides Long-running Operations. Version accessed Mar. 7, 2020. Available online at http://web.archive.org/web/20200307022715if_/https://cloud.google.com/dialogflow/docs/long-running-operations.

Google. Dialogflow How-To Guides Manage Intents with the API. Version accessed Mar. 4, 2020. Available online at http://web.archive.org/web/20200304042804if_/https://cloud.google.com/dialogflow/docs/manage-intents.

Google. Dialogflow How-To Guides Migrating. Version accessed Mar. 7, 2020. Available online at http://web.archive.org/web/20200307004953if_/https://cloud.google.com/dialogflow/docs/migrating.

Google. Dialogflow How-To Guides Telephony Gateway. Version accessed Mar. 12, 2020. Available online at http://web.archive.org/web/20200414180107if_/https://cloud.google.com/dialogflow/docs/integrations/phone-gateway.

Google. Dialogflow How-To Guides. Version accessed on Jan. 31, 2020. Available online at https://web.archive.org/web/20200131184536if_/https://cloud.google.com/dialogflow/docs/how-to.

Google. Dialogflow Quickstarts. Version accessed on Jun. 19, 2019. Available online at https://web.archive.org/web/20190619204640if_/https://cloud.google.com/dialogflow/docs/quickstarts.

Google. Dialogflow Resources Pricing. Version accessed Nov. 15, 2019. Available online at http://web.archive.org/web/20191115060141/https://cloud.google.com/dialogflow/pricing.

Google. Dialogflow Resources Quotas and Limits. Version accessed Feb. 19, 2020. Available online at http://web.archive.org/web/20200219084538/https://cloud.google.com/dialogflow/quotas.

Google. Dialogflow Resources Release Notes. Version accessed Dec. 27, 2019. Available online at http://web.archive.org/web/20191227155622/https://cloud.google.com/dialogflow/docs/release-notes.

Google. Dialogflow Resources Service Level Agreement. Version accessed Feb. 27, 2020. Available online at http://web.archive.org/web/20200227073708if_/https://cloud.google.com/dialogflow/sla.

Google. Dialogflow Resources Terms for opt-in for Dialogflow data logging. Version accessed Jun. 30, 2020. Available online at http://web.archive.org/web/20200630143459if_/https://cloud.google.com/dialogflow/docs/data-logging-terms.

Google. Dialogflow Resources. Version accessed Mar. 5, 2020. Available online at https://web.archive.org/web/20200305224244if_/https://cloud.google.com/dialogflow/docs/resources.

Google. Dialogflow Support Getting Support. Version accessed Apr. 7, 2020. Available online at http://web.archive.org/web/20200407132356/https://cloud.google.com/dialogflow/docs/support/getting-support.

Google. Dialogflow Support. Version accessed Mar. 2, 2020. Available online at https://web.archive.org/web/20200302120657if_/https://cloud.google.com/dialogflow/docs/support.

Google. Dialogflow Tutorials and Samples Build an Agent from Scratch. Create an Intent with parameters. Version accessed Sep. 18, 2019. Available online at https://web.archive.org/web/20190918204229/https://cloud.google.com/dialogflow/docs/tutorials/build-an-agent/create-intent-with-parameters.

Google. Dialogflow Tutorials and Samples Build an Agent from Scratch. Create and Customize and Agent. Version accessed Mar. 8, 2020. Available online at https://web.archive.org/web/20200308182755if_/https://cloud.google.com/dialogflow/docs/tutorials/build-an-agent/create-customize-agent.

Google. Dialogflow Tutorials and Samples Build an Agent from Scratch. Version accessed Mar. 7, 2020. Available online at http://web.archive.org/web/20200307004950if_/https://cloud.google.com/dialogflow/docs/tutorials/build-an-agent.

Google. Dialogflow Tutorials and Samples Other Samples and Learning Material. Version accessed Mar. 2, 2020. Available online at http://web.archive.org/web/20200302014003if_/https://cloud.google.com/dialogflow/docs/tutorials/samples.

(56) References Cited

OTHER PUBLICATIONS

Google. Dialogflow Tutorials and Samples Use Data to Improve Agents. Version accessed Feb. 29, 2020. Available online at http://web.archive.org/web/20200229160127if_/https://cloud.google.com/dialogflow/docs/tutorials/data-to-improve-agents.
Google. Dialogflow Tutorials and Samples. Version accessed Mar. 5, 2020. Available online at https://web.archive.org/web/20200305224128if_/https://cloud.google.com/dialogflow/docs/tutorials.
Google. Google Cloud IOT webpage. Version accessed on Mar. 15, 2019. Available online at https://web.archive.org/web/20190315092712/https://cloud google.com/solutions/iot/.
Hologram. Hologram homepage. Version accessed Mar. 8, 2019. Available online at https://web.archive.org/web/20190308171535/https://www.hologram.io/.
International Searching Authority. International Search Report and Written Opinion for application PCT/US2020/028818, dated Jul. 17, 2020.
Liu, Xi., et al. "Benchmarking natural language understanding services for building conversational agents." arXiv preprint arXiv:1903.05566 (2019).
Microchip. CryptoAuthentication Device Summary Datasheet. ATECC608A. 2018. Available online at http://ww1.microchip.com/downloads/en/DeviceDoc/ATECC608A-CryptoAuthentication-Device-Summary-Data-Sheet-DS40001977B.pdf.
Murata. W-LAN+Bluetooth Combo Module Data Sheet. Last revised on Dec. 6, 2019. Available online at https://wireless.murata.com/datasheet?/RFM/data/type1dx.pdf.
Nordic. Nordic Thingy:52 User guide v1.0. Jun. 2, 2017. Available online at https://www.mouser.com/datasheet/2/297/Thingy_UG_v10-1155091.pdf.
Partovi, S. Life Sciences leadership: Transforming the pharma value chain. Presentation LFS201-L at AWS re: Invent 2019. Dec. 2019.
Passemard, A. Securing Cloud-Connected devices with Cloud IoT and Microchip. May 31, 2018. Available online at https://cloud.google.com/blog/products/gcp/securing-cloud-connected-devices-with-cloud-iot-and-microchip.
Qualcomm. QCS405 webpage. Version accessed May 11, 2019. Available online at https://web.archive.org/web/20190511033322/https://www.qualcomm.com/products/qcs405.
Qualcomm. Qualcomm Smart Audio 400 Platform Development Kit. Updated Dec. 2019. Available online at https://www.qualcomm.com/media/documents/files/smart-audio-400-platform-development-kit-product-brief.pdf.
Rasa. NLU About Page. Version accessed May 30, 2019. Available online at https://rasa.com/docs/rasa/nlu/about/.
Schnoebelen, T. Getting a chatbot to understand 100,000 intentions. Jul. 9, 2016. Available online at https://medium.com/@CrowdFlower/getting-a-chatbot-to-understand-100-000-intentions-f75a53c18ba0.
Sensory. Wake Word & Phrase Recognition Engine webpage. Version accessed Oct. 13, 2020. Available online at https://www.sensory.com/wake-word/.
Shenoy, A. et al. NLP Models Behind RASA Stack. International Journal of Engineering and Advanced Technology (IJEAT) ISSN: 2249-8958, vol. 8, Issue-5S, May 2019.
ST. STM32F427xx STM32F429xx Datasheet & Production Data. Jan. 2018.
Amazon. Alexa HIPAA-Eligible Skills. Version accessed Oct. 13, 2020. Available online at https://developer.amazon.com/en-US/alexa/alexa-skills-kit/get-deeper/custom-skills/healthcare-skills.
Amazon. Amazon IOT webpage. Version accessed on Mar. 15, 2019. Available online at https://web.archive.org/web/20190315041740/https://aws.amazon.com/iot/.
Amazon. WyPy 3.0 by Pycom Ltd page. Version accessed on Oct. 13, 2020. Available online at https://devices.amazonaws.com/detail/a3G0L00000AANtNUAX/WyPy-3.0.
AskHelix. Landing Page. Date accessed Nov. 9, 2018. Available online at https://web.archive.org/web/20181109113113/http://www.askhelix.io/.

Bocklisch, T., et al. "Rasa: Open source language understanding and dialogue management." 31st Conference on Neural Information Processing Systems (NIPS 2017), Long Beach, CA, USA.
Braun, D., et al. "Evaluating natural language understanding services for conversational question answering systems." Proceedings of the 18th Annual SIGdial Meeting on Discourse and Dialogue. 2017.
Cirrus Logic. Smart Codec with Low-Power Audio DSP. CS47L35 Manual. Sep. 2018. Available online at https://statics.cirrus.com/pubs/proDatasheet/CS47L35_F3.pdf.
Cypress. WICED Software webpage. Version Feb. 2019. Available online at https://web.archive.org/web/20190224173030/https://www.cypress.com/products/wiced-software.
Dialogflow. Slot Filling with API.AI using a Pizza Ordering Example. YouTube video. Posted Feb. 11, 2016. Available online at https://www.youtube.com/watch?v=F68HtCtJbGA.
Google. Dialogflow APIs & References. Audit logging. Version accessed Apr. 14, 2020. Available online at https://web.archive.org/web/20200414182921if_/https://cloud.google.com/dialogflow/docs/audit-logging.
Google. Dialogflow APIs & References. Client Libraries C#. Version accessed Apr. 14, 2020. Available online at https://web.archive.org/web/20200414190351if_/https://cloud.google.com/dialogflow/docs/reference/libraries/csharp.
Google. Dialogflow APIs & References. Client Libraries Go. Version accessed Apr. 14, 2020. Available online at https://web.archive.org/web/20200414171548if_/https://cloud.google.com/dialogflow/docs/reference/libraries/go.
Google. Dialogflow APIs & References. Client Libraries Java. Version accessed Apr. 14, 2020. Available online at https://web.archive.org/web/20200414171437if_/https://cloud.google.com/dialogflow/docs/reference/libraries/java.
Google. Dialogflow APIs & References. Client Libraries Node.js. Version accessed Apr. 14, 2020. Available online at https://web.archive.org/web/20200414190321/https://cloud.google.com/dialogflow/docs/reference/libraries/nodejs.
Google. Dialogflow APIs & References. Client Libraries Overview. Version accessed Nov. 14, 2019. Available online at https://web.archive.org/web/20191114113707/https://cloud.google.com/dialogflow/docs/reference/libraries/overview.
Google. Dialogflow APIs & References. Client Libraries PHP. Version accessed Apr. 14, 2020. Available online at https://web.archive.org/web/20200414174532if_/https://cloud.google.com/dialogflow/docs/reference/libraries/php.
Google. Dialogflow APIs & References. Client Libraries Python. Version accessed Apr. 14, 2020. Available online at https://web.archive.org/web/20200414180628if_/https://cloud.google.com/dialogflow/docs/reference/libraries/python.
Google. Dialogflow APIs & References. Client Libraries Ruby. Version accessed Apr. 14, 2020. Available online at https://web.archive.org/web/20190619204641/https://cloud.google.com/dialogflow/docs/reference/libraries/ruby.
Google. Dialogflow APIs & References. Common Types. Version accessed Apr. 14, 2020. Available online at https://web.archive.org/web/20200414174435if_/https://cloud.google.com/dialogflow/docs/reference/common-types.
Google. Dialogflow APIs & References. Languages. Version accessed Nov. 14, 2019. Available online at https://web.archive.org/web/20191114113615/https://cloud.google.com/dialogflow/docs/reference/language.
Google. Dialogflow APIs & References. Predefined follow-up intents. Version accessed Aug. 14, 2019. Available online at https://web.archive.org/web/20190814211447/https://cloud.google.com/dialogflow/docs/reference/follow-up-intent-expressions.
Google. Dialogflow APIs & References. REST API Reference. V2 Overview. Version accessed Apr. 14, 2020. Available online at https://web.archive.org/web/20200414164401/https://cloud.google.com/dialogflow/docs/reference/rest/v2-overview.
Google. Dialogflow APIs & References. REST API Reference. V2Beta1 overview. Version accessed Apr. 14, 2020. Available online at https://web.archive.org/web/20200414164315if_/https://cloud.google.com/dialogflow/docs/reference/rest/v2beta1-overview.

(56) References Cited

OTHER PUBLICATIONS

Google. Dialogflow APIs & References. RPC API Reference. Google.cloud.dialogflow.v2. Version accessed Aug. 27, 2019. Available online at https://web.archive.org/web/20190827071823/https://cloud.google.com/dialogflow/docs/reference/rpc/google.cloud.dialogflow.v2.
Google. Dialogflow APIs & References. RPC API Reference. Google.cloud.dialogflow.v2beta1. Version accessed Apr. 14, 2020. Available online at https://web.archive.org/web/20200414165826if_/https://cloud.google.com/dialogflow/docs/reference/rpc/google.cloud.dialogflow.v2beta1.
Google. Dialogflow APIs & References. RPC API Reference. Google.longrunning. Version accessed Apr. 14, 2020. Available online at https://web.archive.org/web/20200414171535if_/https://cloud.google.com/dialogflow/docs/reference/rpc/google.longrunning.
Google. Dialogflow APIs & References. RPC API Reference. Google.rpc. Version accessed Apr. 14, 2020. Available online at https://web.archive.org/web/20200414165125if_/https://cloud.google.com/dialogflow/docs/reference/rpc/google.rpc.
Google. Dialogflow APIs & References. RPC API Reference. Google.type. Version accessed Apr. 14, 2020. Available online at https://web.archive.org/web/20200414164446if_/https://cloud.google.com/dialogflow/docs/reference/rpc/google.type.
Google. Dialogflow APIs & References. RPC API Reference. Overview. Version accessed Apr. 14, 2020. Available online at https://web.archive.org/web/20200414180624if_/https://cloud.google.com/dialogflow/docs/reference/rpc.
Google. Dialogflow APIs & References. System Entities. Version accessed Oct. 25, 2019. Available online at https://web.archive.org/web/20191025061204/https://cloud.google.com/dialogflow/docs/reference/system-entities.
Google. Dialogflow APIs & References. Version accessed Mar. 18, 2020. Available online at https://web.archive.org/web/20200318060730/https://cloud.google.com/dialogflow/docs/reference.
Google. Dialogflow Concepts Access Control. Version accessed Oct. 1, 2019. Available online at http://web.archive.org/web/20191001175807/https://cloud.google.com/dialogflow/docs/access-control.
Google. Dialogflow Concepts Agent quality and monitoring. Version accessed Mar. 1, 2020. Available online at http://web.archive.org/web/20200301170518if_/https://cloud.google.com/dialogflow/docs/agents-quality.
Google. Dialogflow Concepts Agents. Version accessed Feb. 26, 2020. Available online at http://web.archive.org/web/20200226191216if_/https://cloud.google.com/dialogflow/docs/agents-overview.
Google. Dialogflow Concepts API interactions. Version accessed Jan. 31, 2020. Available online at http://web.archive.org/web/20200131184447if_/https://cloud.google.com/dialogflow/docs/api-overview.
Google. Dialogflow Concepts Best Practices. Version accessed Mar. 9, 2020. Available online at http://web.archive.org/web/20200309000826if_/https://cloud.google.com/dialogflow/docs/best-practices.
Google. Dialogflow Concepts Console overview. Version accessed Jan. 31, 2020. Available online at http://web.archive.org/web/20200131184448if_/https://cloud.google.com/dialogflow/docs/console.
Google. Dialogflow Concepts Contexts. Version accessed Nov. 29, 2019. Available online at http://web.archive.org/web/20191129174302/https://cloud.google.com/dialogflow/docs/contexts-overview.
Google. Dialogflow Concepts Entities. Version accessed Nov. 12, 2019. Available online at http://web.archive.org/web/20191112202601/https://cloud.google.com/dialogflow/docs/entities-overview.
Google. Dialogflow Concepts Events. Version accessed Mar. 5, 2020. Available online at http://web.archive.org/web/20200305214029if_/https://cloud.google.com/dialogflow/docs/events-overview.
Google. Dialogflow Concepts Fulfillment. Version accessed Dec. 20, 2019. Available online at http://web.archive.org/web/20191220112213/https://cloud.google.com/dialogflow/docs/fulfillment-overview.
Google. Dialogflow Concepts Integrations. Version accessed Nov. 15, 2019. Available online at http://web.archive.org/web/20191115060104/https://cloud.google.com/dialogflow/docs/integrations/.
Google. Dialogflow Concepts Training. Version accessed Mar. 18, 2020. Available online at http://web.archive.org/web/20200318060723if_/https://cloud.google.com/dialogflow/docs/training.
Google. Dialogflow Concepts Using multiple projects. Version accessed Mar. 3, 2020. Available online at http://web.archive.org/web/20200303024852if_/https://cloud.google.com/dialogflow/docs/multi-project.
Google. Dialogflow Concepts. Agents. Agent design. Version accessed Jan. 31, 2020. Available online at https://web.archive.org/web/20200131184448/https://cloud.google.com/dialogflow/docs/agents-design.
Google. Dialogflow Concepts. Agents. Agent settings. Version accessed Feb. 27, 2020. Available online at https://web.archive.org/web/20200227111102if_/https://cloud.google.com/dialogflow/docs/agents-settings.
Google. Dialogflow Concepts. Agents. Agent versions and Environments. Version accessed Mar. 6, 2020. Available online at https://web.archive.org/web/20200306114523if_/https://cloud.google.com/dialogflow/docs/agents-versions.
Google. Dialogflow Concepts. Agents. Create and manage agents. Version accessed Mar. 5, 2020. Available online at https://web.archive.org/web/20200305152002/https://cloud.google.com/dialogflow/docs/agents-manage.
Google. Dialogflow Concepts. Agents. Make your agent multilingual. Version accessed Feb. 26, 2020. Available online at https://web.archive.org/web/20200226191218/https://cloud.google.com/dialogflow/docs/agents-multilingual.
Google. Dialogflow Concepts. Agents. Prebuilt agents and small talk. Version accessed Mar. 5, 2020. Available online at https://web.archive.org/web/20200305224240if_/https://cloud.google.com/dialogflow/docs/agents-prebuilt.

* cited by examiner

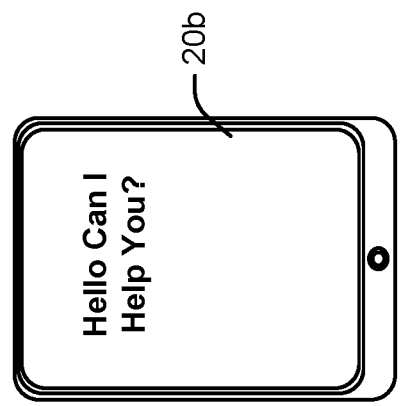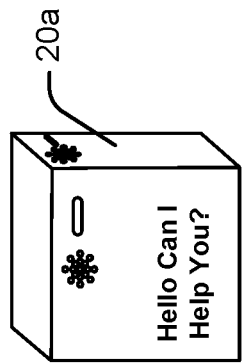
Fig. 14

Fig. 17B

GERMLINE VARIANT DETAILS

BRCA2 chr13:32900447 c.932C>A p.S311*

Clinical Significance: * Pathogenic

This patient has a heterozygous germline pathogenic variant in BRCA2, therefore, PARP inhibitor therapy is recommended. BRCA2 encodes a nuclear phosphoprotein which helps maintain DNA stability through homologous recombination based DNA double stranded break repair and involvement in DNA damage checkpoint control. Germline pathogenic variants in BRCA2 are associated with an increased risk of development of breast, ovarian and fallopian tube cancers in women. Men with pathogenic variants in BRCA2 are at an increased risk to develop breast and prostate cancer, and both men and women are at an increased risk to develop pancreatic cancer. Genetic counseling and appropriate cancer screening are recommended for this patient and any potentially affected family members.

CLINICAL HISTORY

2018
- Release from Family Center ICU
  1/6/2018

2017
- Biopsy: Lung
  MRI: Abdomen
  12/29/2017

- Admitted to Family Center ICU
  12/28/2017

- Started Palbociclib
  Ended Gemcitabine
  9/10/2017

- CT: Chest
  9/2/2017

- Started Gemcitabine
  8/21/2017

- Diagnosis: Pancreatic ductal adenocarcinoma T2 N0 M0
  CT: Chest
  Pancreaticoduodenectomy
  Family Center ICU
  Comorbidity: Diabetes
  8/16/2017

Fig. 17C

The BRCA mutation is...

COLLABORATIVE ARTIFICIAL INTELLIGENCE METHOD AND SYSTEM

CROSS-REFERENCE TO RELATED APPLICATIONS

This application is a continuation of U.S. patent application Ser. No. 16/852,138, filed Apr. 17, 2020, which is titled "COLLABORATIVE ARTIFICIAL INTELLIGENCE METHOD AND SYSTEM," which claims priority to U.S. provisional patent application No. 62/871,667, filed Jul. 8, 2019, which is titled "COLLABORATIVE ARTIFICIAL INTELLIGENCE METHOD AND SYSTEM," to U.S. provisional patent application No. 62/855,646, filed May 31, 2019, which is titled "COLLABORATIVE ARTIFICIAL INTELLIGENCE METHOD AND APPARATUS," and to U.S. provisional patent application No. 62/835,339, filed Apr. 17, 2019, which is titled "COLLABORATIVE ARTIFICIAL INTELLIGENCE METHOD AND APPARATUS."

APPLICATIONS INCORPORATED BY REFERENCE

Each of the following US patent applications is incorporated herein in its entirety by reference.

(1) U.S. patent application Ser. No. 16/657,804 which is titled "DATA BASED CANCER RESEARCH AND TREATMENT SYSTEMS AND METHODS," which was filed on Oct. 18, 2019;

(2) U.S. patent application Ser. No. 16/671,165 which is titled "USER INTERFACE, SYSTEM, AND METHOD FOR COHORT ANALYSIS," which was filed on Oct. 31, 2019;

(3) U.S. patent application Ser. No. 16/732,168 which is titled "A METHOD AND PROCESS FOR PREDICTING AND ANALYZING PATIENT COHORT RESPONSE, PROGRESSION, AND SURVIVAL," which was filed on Dec. 31, 2019.

STATEMENT REGARDING FEDERALLY SPONSORED RESEARCH OR DEVELOPMENT

Not applicable.

BACKGROUND OF THE DISCLOSURE

The field of this disclosure is systems for accessing and manipulating large complex data sets in ways that enable system users to develop new insights and conclusions with minimal user-interface friction hindering access and manipulation.

The present disclosure describes innovations that will be described in the context of an exemplary healthcare worker that collaborates with patients to diagnose ailment states, prescribe treatments, and administer those treatments to improve overall patient health. In addition, while many different types of healthcare workers (e.g., doctors, psychologists, physical therapists, nurses, administrators, researchers, insurance experts, pharmacists, etc.) in many different medical disciplines (e.g., cancer, Alzheimer's disease, Parkinson's disease, mental illnesses, cardiology, immunology, infectious disease, and diabetes) will benefit from the disclosed innovations, unless indicated otherwise, the innovations will be described in the context of an exemplary oncologist/researcher (hereinafter "oncologist") who collaborates with patients to diagnose cancer states (e.g., all physiological, habit, history, genetic and treatment efficacy factors), understand and evaluate existing data and guidelines for patients similar to their patient, prescribe treatments, administer those treatments, and observes patient outcomes, all to improve overall patient health, and/or who performs medical research in cancer.

Many professions require complex thought where people need to consider many factors when selecting solutions to encountered situations, hypothesize new factors and solutions and test new factors and solutions to make sure that they are effective. For instance, oncologists considering specific patient cancer states, optimally should consider many different factors when assessing the patient's cancer state as well as many factors when crafting and administering an optimized treatment plan. For example, these factors include the patient's family history, past medical conditions, current diagnosis, genomic/molecular profile of the patient's hereditary DNA and of the patient's tumor's DNA, current nationally recognized guidelines for standards of care within that cancer subtype, recently published research relating to that patient's condition, available clinical trials pertaining to that patient, available medications and other therapeutic interventions that may be a good option for the patient and data from similar patients. In addition, cancer and cancer treatment research are evolving rapidly so that researchers need to continually utilize data, new research and new treatment guidelines to think critically about new factors and treatments when diagnosing cancer states and optimized treatment plans.

In particular, it is no longer possible for an oncologist to be familiar with all new research in the field of cancer care. Similarly, it is extremely challenging for an oncologist to be able to manually analyze the medical records and outcomes of thousands or millions of cancer patients each time an oncologist wants to make a specific treatment recommendation regarding a particular patient being treated by that oncologist. As an initial matter, oncologists often do not even have access to health information from institutions other than their own. In the United States, implementation of the federal law known as the Health Insurance Portability and Accountability Act of 1996 ("HIPAA") places significant restrictions on the ability of one health care provider to access health records of another health care provider. In addition, health care systems face administrative, technical, and financial challenges in making their data available to a third party for aggregation with similar data from other health care systems. To the extent health care information from multiple patients seen at multiple providers has been aggregated into a single repository, there is a need for a system and method that structures that information using a common data dictionary or library of data dictionaries. Where multiple institutions are responsible for the development of a single, aggregated repository, there can be significant disagreement over the structure of the data dictionary or data dictionaries, the methods of accessing the data, the individuals or other providers permitted to access the data, the quantity of data available for access, and so forth. Moreover, the scope of the data that is available to be searched is overwhelming for any oncologist wishing to conduct a manual review. Every patient has health information that includes hundreds or thousands of data elements. When including sequencing information in the health information to be accessed and analyzed, such as from next-generation sequencing, the volume of health information that could be analyzed grows intensely. A single FASTQ or BAM file that is produced in the course of whole-exome sequencing, for instance, takes up gigabytes of storage, even though it includes sequencing for only the patient's exome, which is thought to be about 1-2% of the whole human genome.

In this regard, an oncologist may have a simple question—"what is the best medication for this particular patient?"—the answer to which requires an immense amount of health information, analytical software modules for analyzing that information, and a hardware framework that permits those modules to be executed in order to provide an answer. Almost all queries/ideas/concepts are works in progress that evolve over time as critical thinking is applied and additional related factors and factor relationships are recognized and/or better understood. All queries start as a hypothesis rooted in consideration of a set of interrelated raw material (e.g., data). The hypothesis is usually tested by asking questions related to the hypothesis and determining if the hypothesis is consistent and persists when considered in light of the raw material and answers to the questions. Consistent/persistent hypothesis become relied upon ideas (i.e., facts) and additional raw material for generating next iterations of the initial ideas as well as completely new ideas.

When considering a specific cancer state, an oncologist considers known factors (e.g., patient conditions, prior treatments, treatment efficacy, etc.), forms a hypothesis regarding optimized treatment, considers that hypothesis in light of prior data and prior research relating similar cancer states to treatment efficacies and, where the prior data indicates high efficacy regarding the treatment hypothesis, may prescribe the hypothesized treatment for a patient. Where data indicates poor treatment efficacy the oncologist reconsiders and generates a different hypothesis and continues the iterative testing and conclusion cycle until an efficacious treatment plan is identified. Cancer researchers perform similar iterative hypothesis, data testing and conclusion processes to derive new cancer research insights.

Tools have been and continue to be developed to help oncologists diagnose cancer states, select and administer optimized treatments and explore and consider new cancer state factors, new cancer states (e.g., diagnosis), new treatment factors, new treatments and new efficacy factors. For instance, massive cancer databases have been developed and are maintained for access and manipulation by oncologists to explore diagnosis and treatment options as well as new insights and treatment hypothesis. Computers enable access to and manipulation of cancer data and derivatives thereof.

Cancer data tends to be voluminous and multifaceted so that many useful representations include substantial quantities of detail and specific arrangements of data or data derivatives that are optimally visually represented. For this reason, oncological and research computer workstations typically include conventional interface devices like one or more large flat panel display screens for presenting data representations and a keyboard, mouse, or other mechanical input device for entering information, manipulating interface tools and presenting many different data representations. In many cases a workstation computer/processor runs electronic medical records (EMR) or medical research application programs (hereinafter "research applications") that present different data representations along with on screen cursor selectable control icons for selecting different data access and manipulation options.

While conventional computers and workstations operate well as data access and manipulation interfaces, they have several shortcomings. First, using a computer interface often requires an oncologist to click many times, on different interfaces, to find a specific piece of information. This is a cumbersome and time consuming process which often does not result in the oncologist achieving the desired result and receiving the answer to the question they are trying to ask.

Second, in many cases it is hard to capture hypothetical queries when they occur and the ideas are not followed up on in a timely fashion or are lost forever. Queries are not restricted to any specific time schedule and therefore often occur at inconvenient times when an oncologist is not logged into a workstation and using a research application usable to capture and test the idea. For instance, an oncologist may be at home when she becomes curious about some aspect of a patient's cancer state or some statistic related to one of her patients or when she first formulates a treatment hypothesis for a specific patient's cancer state. In this case, where the oncologist's workstation is at a remote medical facility, the oncologist cannot easily query a database or capture or test the hypothesis.

Also, in this case, even if the oncologist can use a laptop or other home computer to access a research application from home, the friction involved with engaging the application often has an impeding effect. In this regard, application access may require the oncologist to retrieve a laptop or physically travel to a stationary computer in her home, boot up the computer operating system, log onto the computer (e.g., enter user name and password), select and start a research application, navigate through several application screenshots to a desired database access tool suite and then enter a query or hypothesis defining information in order to initiate hypothesis testing. This application access friction is sufficient in many cases to dissuade immediate queries or hypothesis capture and testing, especially in cases where an oncologist simply assumes she will remember the query or hypothesis the next time she access her computer interface. As anyone who has a lot of ideas knows, ideas are fleeting and therefore ideas not immediately captured are often lost. More importantly, oncologists typically have limited amounts of time to spend on each patient case and need to have their questions and queries resolved immediately while they are evaluating information specific to that patient.

Third, in many cases a new query or hypothesis will occur to an oncologist while engaged in some other activity unrelated to oncological activities. Here, as with many people, immediate consideration and testing via a conventional research application is simply not considered. Again, no immediate capture can lead to lost ideas.

Fourth, in many cases oncological and research data activities will include a sequence of consecutive questions or requests (hereinafter "requests") that hone in on increasingly detailed data responses where the oncologist/researcher has to repeatedly enter additional input to define next level requests as intermediate results are not particularly interesting. In addition, while visual representations of data responses to oncological and research requests are optimal in many cases, in other cases visual representations tend to hamper user friendliness and can even be overwhelming. In these cases, while the visual representations are usable, the representations can require appreciable time and effort to consume presented information (e.g., reading results, mentally summarizing results, etc.). In short, conventional oncological interfaces are often clunky to use.

Moreover, today, oncologists and other professionals have no simple mechanism for making queries of large, complex databases and receiving answers in real time, without needing to interact with electronic health record systems or other cumbersome software solutions. In particular, there is a need for systems and methods that allow a provider to query a device using his or her voice, with questions relating to the optimal care of his or her patient, where the answers to those questions are generated from unique data sets that provide context and new information relative to the patient, including vast amounts of real world historical clinical information combined with other forms of medical data such as molecular data from omics sequencing and imaging data, as well as data derived from such data using analytics to determine which path is most optimal for that singular patient Thus, what is needed is an intuitive interface for complex databases that enables oncologists, researchers, and other professionals and database users to access and manipulate data in various ways to generate queries and test hypothesis or new ideas thereby thinking through those ideas in the context of different data sets with minimal access and manipulation friction. It would be advantageous if the interface were present at all times or at least portable so that it is available essentially all the time. It would also be advantageous if a system associated with the interface would memorialize user-interface interactions thereby enabling an oncologist or researcher to reconsider the interactions at a subsequent time to re-engage for the purpose of continuing a line of questions or hypothesis testing without losing prior thoughts.

It would also be advantageous to have a system that captures an oncologist's thoughts for several purposes such as developing better healthcare aid systems, generating automated records and documents and offering up services like appointment, test and procedure scheduling, prescription preparation, etc.

It would also be advantageous to have an interface available across several different form factors.

SUMMARY OF THE DISCLOSURE

It has been recognized that a relatively small and portable voice activated and audio responding interface device (hereinafter "collaboration device") can be provided enabling oncologists to conduct at least initial database access and manipulation activities. In at least some embodiments, a collaboration device includes a processor linked to each of a microphone, a speaker and a wireless transceiver (e.g., transmitter and receiver). The processor runs software for capturing voice signals generated by an oncologist. An automated speech recognition (ASR) system converts the voice signals to a text file which is then processed by a natural language processor (NLP) or other artificial intelligence module (e.g., a natural language understanding module) to generate a data operation (e.g., commands to perform some data access or manipulation process such as a query, a filter, a memorialization, a clearing of prior queries and filter results, note etc.).

In at least some embodiments the collaboration device is used within a collaboration system that includes a server that maintains and manipulates an industry specific data repository. The data operation is received by the collaboration server and used to access and/or manipulate data the database data thereby generating a data response. In at least some cases, the data response is returned to the collaboration device as an audio file which is broadcast to the oncologist as a result associated with the original query.

In some cases the voice signal to text file transcription is performed by the collaboration device processor while in other cases the voice signal is transmitted from the collaboration device to the collaboration server and the collaboration server does the transcription to a text file. In some cases the text file is converted to a data operation by the collaboration device processor and in other cases that conversion is performed by the collaboration server. In some cases the collaboration server maintains or has access to the industry specific database so that the server operates as an intermediary between the collaboration device and the industry specific database.

In at least some embodiments the collaboration device is a dedicated collaboration device that is provided solely as an interface to the collaboration server and industry specific database. In these cases, the collaboration interface device may be on all the time and may only run a single dedicated application program so that the device does not require any boot up time and can be activated essentially immediately via a single activation activity performed by an oncologist.

For instance, in some cases the collaboration device may have motion sensors (e.g., an accelerometer, a gyroscope, etc.) linked to the processor so that the simple act of picking up the device causes the processor to activate an application. In other cases the collaboration device processor may be programmed to "listen" for the phrase "Hey query" and once received, activate to capture a next voice signal utterance that operates as seed data for generating the text file. In other cases the processor may be programmed to listen for a different activation phrase, such as a brand name of the system or a combination of a brand name plus a command indication. For instance, if the brand name of the system is "One" then the activation phrase may be "One" or "Go One" or the like. In still other cases the collaboration device may simply listen for voice signal utterances that it can recognize as oncological queries and may then automatically use any recognized query as seed data for text generation.

In addition to providing audio responses to data operations, in at least some cases the system automatically records and stores data operations (e.g., data defining the operations) and responses as a collaboration record for subsequent access. The collaboration record may include one or the other or both of the original voice signal and broadcast response or the text file and a text response corresponding to the data response. Here, the stored collaboration record provides details regarding the oncologist's search and data operation activities that help automatically memorialize the hypothesis or idea the oncologist was considering. In a case where an oncologist asks a series of queries, those queries and data responses may be stored as a single line of questioning so that they together provide more detail for characterizing the oncologist's initial hypothesis or idea. At a subsequent time, the system may enable the oncologist to access the memorialized queries and data responses so that she can re-enter a flow state associated therewith and continue hypothesis testing and data manipulation using a workstation type interface or other computer device that includes a display screen and perhaps audio devices like speakers, a microphone, etc., more suitable for presenting more complex data sets and data representations.

In addition to simple data search queries, other voice signal data operation types are contemplated. For instance, the system may support filter operations where an oncologist voice signal message defines a sub-set of the industry specific database set. For example, the oncologist may voice the message "Access all medical records for male patients over 45 years of age that have had pancreatic cancer since 1990", causing the system to generate an associated subset of data that meet the specified criteria.

Importantly, some data responses to oncological queries will be "audio suitable" meaning that the response can be well understood and comprehended when broadcast as an audio message. In other cases a data response simply may not be well suited to be presented as an audio output. For instance, where a query includes the phrase "Who is the patient that I saw during my last office visit last Thursday?", an audio suitable response may be "Mary Brown." On the other hand, if a query is "List all the medications that have been prescribed for males over 45 years of age that have had pancreatic cancer since 1978" and the response includes a list of 225 medications, the list would not be audio suitable as it would take a long time to broadcast each list entry and comprehension of all list entries would be dubious at best.

In cases where a data response is optimally visually presented, the system may take alternate or additional steps to provide the response in an intelligible format to the user. The system may simply indicate as part of an audio response that response data would be more suitably presented in visual format and then present the audio response. If there is a proximate large display screen, such as a computer monitor or a television (TV) such as a smart TV, the system may pair with that display and present visual data with or without audio data. The system may simply indicate that no suitable audio response is available. In some embodiments, the system may pair with a computational device that includes a display, such as a smartphone, tablet computer, etc.

Thus, at least some inventive embodiments enable intuitive and rapid access to complex data sets essentially anywhere within a wireless communication zone so that an oncologist can initiate thought processes in real time when they occur. By answering questions when they occur, the system enables oncologists to dig deeper in the moment into data and continue the thought process through a progression of queries. Some embodiments memorialize an oncologist's queries and responses so that at subsequent times the oncologist can re-access that information and continue queries related thereto. In cases where visual and audio responses are available, the system may adapt to provide visual responses when visual capabilities are present or may simply store the visual responses as part of a collaboration record for subsequent access when an oncologist has access to a workstation or the like.

In at least some embodiments the disclosure includes a method for interacting with a database to access data therein, the method for use with a collaboration device including a speaker, a microphone and a processor, the method comprising the steps of associating separate sets of state-specific intents and supporting information with different clinical report types, the supporting information including at least one intent-specific data operation for each state-specific intent, receiving a voice query via the microphone seeking information, identifying a specific patient associated with the query, identifying a state-specific clinical report associated with the identified patient, attempting to select one of the state-specific intents associated with the identified state-specific clinical report as a match for the query, upon selection of one of the state-specific intents, performing the at least one data operation associated with the selected state-specific intent to generate a result, using the result to form a query response and broadcasting the query response via the speaker.

In some cases the method is for use with at least a first database that includes information in addition the clinical reports, the method further including, in response to the query, obtaining at least a subset of the information in addition to the clinical reports, the step of using the result to form a query response including using the result and the additional obtained information to form the query response.

In some cases the at least one data operation includes at least one data operation for accessing additional information from the database, the step of obtaining at least a subset includes obtaining data per the at least one data operation for accessing additional information from the database.

Some embodiments include a method for interacting with a database to access data therein, the method for use with a collaboration device including a speaker, a microphone and a processor, the method comprising the steps of associating separate sets of state-specific intents and supporting information with different clinical report types, the supporting information including at least one intent-specific primary data operation for each state-specific intent, receiving a voice query via the microphone seeking information, identifying a specific patient associated with the query, identifying a state-specific clinical report associated with the identified patient, attempting to select one of the state-specific intents associated with the identified state-specific clinical report as a match for the query, upon selection of one of the state-specific intents, performing the primary data operation associated with the selected state-specific intent to generate a result, performing a supplemental data operation on data from a database that includes data in addition to the clinical report data to generate additional information, using the result and the additional information to form a query response and broadcasting the query response via the speaker.

Some embodiments include a method of audibly broadcasting responses to a user based on user queries about a specific patient molecular report, the method comprising receiving an audible query from the user to a microphone coupled to a collaboration device, identifying at least one intent associated with the audible query, identifying at least one data operation associated with the at least one intent, associating each of the at least one data operations with a first set of data presented on the molecular report, executing each of the at least one data operations on a second set of data to generate response data, generating an audible response file associated with the response data and providing the audible response file for broadcasting via a speaker coupled to the collaboration device.

In at least some cases the audible query includes a question about a nucleotide profile associated with the patient. In at least some cases the nucleotide profile associated with the patient is a profile of the patient's cancer. In at least some cases the nucleotide profile associated with the patient is a profile of the patient's germline. In at least some cases the nucleotide profile is a DNA profile. In at least some cases the nucleotide profile is an RNA expression profile. In at least some cases the nucleotide profile is a mutation biomarker.

In at least some cases the mutation biomarker is a BRCA biomarker. In at least some cases the audible query includes a question about a therapy. In at least some cases the audible query includes a question about a gene. In at least some cases the audible query includes a question about a clinical data. In at least some cases the audible query includes a question about a next-generation sequencing panel. In at least some cases the audible query includes a question about a biomarker.

In at least some cases the audible query includes a question about an immune biomarker. In at least some cases the audible query includes a question about an antibody-based test. In at least some cases the audible query includes a question about a clinical trial. In at least some cases the audible query includes a question about an organoid assay. In at least some cases the audible query includes a question about a pathology image. In at least some cases the audible query includes a question about a disease type. In at least some cases the at least one intent is an intent related to a biomarker. In at least some cases the biomarker is a BRCA biomarker. In at least some cases the at least one intent is an intent related to a clinical condition. In at least some cases the at least one intent is an intent related to a clinical trial.

In at least some cases the at least one intent is related to a drug. In at least some cases the drug intent is related to a drug is chemotherapy. In at least some cases the drug intent is an intent related to a PARP inhibitor intent. In at least some cases the at least one intent is related to a gene. In at least some cases the at least one intent is related to immunology. In at least some cases the at least one intent is related to a knowledge database. In at least some cases the at least one intent is related to testing methods. In at least some cases the at least one intent is related to a gene panel. In at least some cases the at least one intent is related to a report. In at least some cases the at least one intent is related to an organoid process. In at least some cases the at least one intent is related to imaging.

In at least some cases the at least one intent is related to a pathogen. In at least some cases the at least one intent is related to a vaccine. In at least some cases the at least one data operation includes an operation to identify at least one treatment option. In at least some cases the at least one data operation includes an operation to identify knowledge about a therapy. In at least some cases the at least one data operation includes an operation to identify knowledge related to at least one drug (e.g., "What drugs are associated with high CD40 expression?"). In at least some cases the at least one data operation includes an operation to identify knowledge related to mutation testing (e.g., "Was Dwayne Holder's sample tested for a KMT2D mutation?"). In at least some cases the at least one data operation includes an operation to identify knowledge related to mutation presence (e.g., "Does Dwayne Holder have a KMT2C mutation?"). In at least some cases the at least one data operation includes an operation to identify knowledge related to tumor characterization (e.g. "Could Dwayne Holder's tumor be a BRCA2 driven tumor?"). In at least some cases the at least one data operation includes an operation to identify knowledge related to testing requirements (e.g., "What tumor percentage does Tempus require for TMB results?"). In at least some cases the at least one data operation includes an operation to query for definition information (e.g., "What is PDL1 expression?"). In at least some cases the at least one data operation includes an operation to query for expert information (e.g., "What is the clinical relevance of PDL1 expression?"; "What are the common risks associated with the Whipple procedure?"). In at least some cases the at least one data operation includes an operation to identify information related to recommended therapy (e.g., "Dwayne Holder is in the 88th percentile of PDL1 expression, is he a candidate for immunotherapy?"). In at least some cases the at least one data operation includes an operation to query for information relating to a patient (e.g., Dwayne Holder). In at least some cases the at least one data operation includes an operation to query for information relating to patients with one or more clinical characteristics similar to the patient (e.g., "What are the most common adverse events for patients similar to Dwayne Holder?").

In at least some cases the at least one data operation includes an operation to query for information relating to patient cohorts (e.g., "What are the most common adverse events for pancreatic cancer patients?"). In at least some cases the at least one data operation includes an operation to query for information relating to clinical trials (e.g., "Which clinical trials is Dwayne the best match for?").

In at least some cases the at least one data operation includes an operation to query about a characteristic relating to a genomic mutation. In at least some cases the characteristic is loss of heterozygosity. In at least some cases the characteristic reflects the source of the mutation. In at least some cases the source is germline. In at least some cases the source is somatic. In at least some cases the characteristic includes whether the mutation is a tumor driver. In at least some cases the first set of data comprises a patient name.

In at least some cases the first set of data comprises a patient age. In at least some cases the first set of data comprises a next-generation sequencing panel. In at least some cases the first set of data comprises a genomic variant. In at least some cases the first set of data comprises a somatic genomic variant. In at least some cases the first set of data comprises a germline genomic variant. In at least some cases the first set of data comprises a clinically actionable genomic variant. In at least some cases the first set of data comprises a loss of function variant. In at least some cases the first set of data comprises a gain of function variant.

In at least some cases the first set of data comprises an immunology marker. In at least some cases the first set of data comprises a tumor mutational burden. In at least some cases the first set of data comprises a microsatellite instability status. In at least some cases the first set of data comprises a diagnosis. In at least some cases the first set of data comprises a therapy. In at least some cases the first set of data comprises a therapy approved by the U.S. Food and Drug Administration. In at least some cases the first set of data comprises a drug therapy. In at least some cases the first set of data comprises a radiation therapy. In at least some cases the first set of data comprises a chemotherapy. In at least some cases the first set of data comprises a cancer vaccine therapy. In at least some cases the first set of data comprises an oncolytic virus therapy.

In at least some cases the first set of data comprises an immunotherapy. In at least some cases the first set of data comprises a pembrolizumab therapy. In at least some cases the first set of data comprises a CAR-T therapy. In at least some cases the first set of data comprises a proton therapy. In at least some cases the first set of data comprises an ultrasound therapy. In at least some cases the first set of data comprises a surgery. In at least some cases the first set of data comprises a hormone therapy. In at least some cases the first set of data comprises an off-label therapy. In at least some cases, the first set of data comprises a gene editing therapy. In at least some cases, the gene editing therapy can be clustered regularly interspaced short palindromic repeats (CRISPR) therapy.

In at least some cases the first set of data comprises an on-label therapy. In at least some cases the first set of data comprises a bone marrow transplant event. In at least some cases the first set of data comprises a cryoablation event. In at least some cases the first set of data comprises a radiofrequency ablation. In at least some cases the first set of data comprises a monoclonal antibody therapy. In at least some cases the first set of data comprises an angiogenesis inhibitor. In at least some cases the first set of data comprises a PARP inhibitor.

In at least some cases the first set of data comprises a targeted therapy. In at least some cases the first set of data comprises an indication of use. In at least some cases the first set of data comprises a clinical trial. In at least some cases the first set of data comprises a distance to a location conducting a clinical trial. In at least some cases the first set of data comprises a variant of unknown significance. In at least some cases the first set of data comprises a mutation effect.

In at least some cases the first set of data comprises a variant allele fraction. In at least some cases the first set of data comprises a low coverage region. In at least some cases the first set of data comprises a clinical history. In at least some cases the first set of data comprises a biopsy result. In at least some cases the first set of data comprises an imaging result. In at least some cases the first set of data comprises an MRI result.

In at least some cases the data comprises a CT result. In at least some cases the first set of data comprises a therapy prescription. In at least some cases the first set of data comprises a therapy administration. In at least some cases the first set of data comprises a cancer subtype diagnosis. In at least some cases the first set of data comprises an cancer subtype diagnosis by RNA class. In at least some cases the first set of data comprises a result of a therapy applied to an organoid grown from the patient's cells. In at least some cases the first set of data comprises a tumor quality measure. In at least some cases the first set of data comprises a tumor quality measure selected from at least one of the set of PD-L1, MMR, tumor infiltrating lymphocyte count, and tumor ploidy. In at least some cases the first set of data comprises a tumor quality measure derived from an image analysis of a pathology slide of the patient's tumor. In at least some cases the first set of data comprises a signaling pathway associated with a tumor of the patient.

In at least some cases the signaling pathway is a HER pathway. In at least some cases the signaling pathway is a MAPK pathway. In at least some cases the signaling pathway is a MDM2-TP53 pathway. In at least some cases the signaling pathway is a PI3K pathway. In at least some cases the signaling pathway is a mTOR pathway.

In at least some cases the at least one data operations includes an operation to query for a treatment option, the first set of data comprises a genomic variant, and the associating step comprises adjusting the operation to query for the treatment option based on the genomic variant. In at least some cases the at least one data operations includes an operation to query for a clinical history data, the first set of data comprises a therapy, and the associating step comprises adjusting the operation to query for the clinical history data element based on the therapy. In at least some cases the clinical history data is medication prescriptions, the therapy is pembrolizumab, and the associating step comprises adjusting the operation to query for the prescription of pembrolizumab.

In at least some cases the second set of data comprises clinical health information. In at least some cases the second set of data comprises genomic variant information. In at least some cases the second set of data comprises DNA sequencing information. In at least some cases the second set of data comprises RNA information. In at least some cases the second set of data comprises DNA sequencing information from short-read sequencing. In at least some cases the second set of data comprises DNA sequencing information from long-read sequencing. In at least some cases the second set of data comprises RNA transcriptome information. In at least some cases the second set of data comprises RNA full-transcriptome information. In at least some cases the second set of data is stored in a single data repository. In at least some cases the second set of data is stored in a plurality of data repositories.

In at least some cases the second set of data comprises clinical health information and genomic variant information. In at least some cases the second set of data comprises immunology marker information. In at least some cases the second set of data comprises microsatellite instability immunology marker information. In at least some cases the second set of data comprises tumor mutational burden immunology marker information. In at least some cases the second set of data comprises clinical health information comprising one or more of demographic information, diagnostic information, assessment results, laboratory results, prescribed or administered therapies, and outcomes information.

In at least some cases the second set of data comprises demographic information comprising one or more of patient age, patient date of birth, gender, race, ethnicity, institution of care, comorbidities, and smoking history. In at least some cases the second set of data comprises diagnosis information comprising one or more of tissue of origin, date of initial diagnosis, histology, histology grade, metastatic diagnosis, date of metastatic diagnosis, site or sites of metastasis, and staging information. In at least some cases the second set of data comprises staging information comprising one or more of TNM, ISS, DSS, FAB, RAI, and Binet. In at least some cases the second set of data comprises assessment information comprising one or more of performance status (including ECOG or Karnofsky status), performance status score, and date of performance status.

In at least some cases the second set of data comprises laboratory information comprising one or more of type of lab (e.g. CBS, CMP, PSA, CEA), lab results, lab units, date of lab service, date of molecular pathology test, assay type, assay result (e.g. positive, negative, equivocal, mutated, wild type), molecular pathology method (e.g. IHC, FISH, NGS), and molecular pathology provider. In at least some cases the second set of data comprises treatment information comprising one or more of drug name, drug start date, drug end date, drug dosage, drug units, drug number of cycles, surgical procedure type, date of surgical procedure, radiation site, radiation modality, radiation start date, radiation end date, radiation total dose delivered, and radiation total fractions delivered.

In at least some cases the second set of data comprises outcomes information comprising one or more of Response to Therapy (e.g. CR, PR, SD, PD), RECIST score, Date of Outcome, date of observation, date of progression, date of recurrence, adverse event to therapy, adverse event date of presentation, adverse event grade, date of death, date of last follow-up, and disease status at last follow up. In at least some cases the second set of data comprises information that has been de-identified in accordance with a de-identification method permitted by HIPAA.

In at least some cases the second set of data comprises information that has been de-identified in accordance with a safe harbor de-identification method permitted by HIPAA. In at least some cases the second set of data comprises information that has been de-identified in accordance with a statistical de-identification method permitted by HIPAA. In at least some cases the second set of data comprises clinical health information of patients diagnosed with a cancer condition.

In at least some cases the second set of data comprises clinical health information of patients diagnosed with a cardiovascular condition. In at least some cases the second set of data comprises clinical health information of patients diagnosed with a diabetes condition. In at least some cases the second set of data comprises clinical health information of patients diagnosed with an autoimmune condition. In at least some cases the second set of data comprises clinical health information of patients diagnosed with a lupus condition.

In at least some cases the second set of data comprises clinical health information of patients diagnosed with a psoriasis condition. In at least some cases the second set of data comprises clinical health information of patients diagnosed with a depression condition. In at least some cases the second set of data comprises clinical health information of patients diagnosed with a rare disease.

In at least some embodiments, a method of audibly broadcasting responses to a user based on user queries about a specific patient's molecular report is provided by the disclosure. The method can be used with a collaboration device that includes a processor and a microphone and a speaker linked to the processor. The method can include storing molecular reports for a plurality of patients in a system database, receiving an audible query from the user via the microphone, identifying at least one intent associated with the audible query, identifying at least one data operation associated with the at least one intent, accessing the specific patient's molecular report, executing at least one of the identified at least one data operations on a first set of data included in the specific patient's molecular report to generate a first set of response data, using the first set of response data to generate an audible response file, and broadcasting the audible response file via the speaker.

In at least some cases the method can further include identifying qualifying parameters in the audible query, the step of identifying at least one data operation including identifying the at least one data operation based on both the identified intent and the qualifying parameters.

In at least some cases at least one of the qualifying parameters can include a patient identity.

In at least some cases at least one of the qualifying parameters can include a patient's disease state.

In at least some cases at least one of the qualifying parameters can include a genetic mutation.

In at least some cases at least one of the qualifying parameters can include a procedure type.

In at least some cases the method can further include identifying qualifying parameters in the specific patient's molecular report, the step of identifying at least one data operation including identifying the at least one data operation based on both the identified intent and the qualifying parameters.

In at least some cases the method can further include the step of storing a general knowledge database that includes non-patient specific data about specific topics, wherein the step of identifying at least one data operation associated with the at least one intent includes identifying at least first and second data operations associated with the at least one intent, the first data operation associated with the specific patient's molecular report and the second data operation associated with the general knowledge database.

In at least some cases the second data operation associated with the general knowledge database can be executed first to generate second data operation results, the second data operation results can be used to define the first data operation and the first data operation associated with the specific patient's molecular report can be executed second to generate the first set of response data.

In at least some cases the first data operation associated with the specific patient's molecular report can be executed first to generate first data operation results, the first data operation results can be used to define the second data operation and the second data operation associated with the general knowledge database can be executed second to generate the first set of response data.

In at least some cases the step of identifying at least one intent can include determining that the audible query is associated with the specific patient, accessing the specific patient's molecular report, determining the specific patient's cancer state from the molecular report and then selecting an intent from a pool of cancer state related intents.

In at least some cases the method can further include the step of storing a general knowledge database that includes non-patient specific data about specific topics, the method further including the steps of, upon determining that the audible query is not associated with any specific patient, selecting an intent that is associated with the general knowledge database.

In at least some cases the collaboration device can include a portable wireless device that includes a wireless transceiver.

In at least some cases the collaboration device can be a handheld device.

In at least some cases the collaboration device can include at least one visual indicator, the processor linked to the visual indicator and controllable to change at least some aspect of the appearance of the visual indicator to indicate different states of the collaboration device.

In at least some cases the processor can be programmed to monitor microphone input to identify a "wake up" phrase, the processor monitoring for the audible query after the wake up phrase is detected.

In at least some cases a series of audible queries can be received via the microphone, and the at least one of the identified data operations can include identifying a subset of data that is usable with subsequent audio queries to identify intents associated with the subsequent queries.

In at least some cases the method can further include the steps of, based on at least one audible query received via the microphone and related data in a system database, identifying at least one activity that a collaboration device user may want to perform and initiating the at least one activity.

In at least some cases the step of initiating the at least one activity can include generating a second audible response file and broadcasting the second audible response file to the user seeking verification that the at least one activity should be performed and monitoring the microphone for an affirmative response and, upon receiving an affirmative response, initiating the at least one activity.

In at least some cases the at least one activity can include periodically capturing health information from electronic health records included in the system database.

In at least some cases the at least one activity can include checking status of an existing clinical or lab order.

In at least some cases the at least one activity can include ordering a new clinical or lab order.

In at least some cases the collaboration device can be one of a smartphone, a tablet computer, a laptop computer, a desktop computer, or an Amazon Echo.

In at least some cases the step of initiating the at least one activity can include automatically initiating the at least one activity without any initiating input from the user.

In at least some cases the method can further including storing and maintaining a general cancer knowledge database, persistently updating the specific patient's molecular report, automatically identifying at least one intent and associated data operation related to the general cancer knowledge database based on the specific patient's molecular report data, persistently executing the associated data operation on the general cancer knowledge database to generate a new set of response data not previously generated and, upon generating a new set of response data, using the new set of response data to generate another audible response file and broadcasting the another audible response file via the speaker.

In at least some cases the method can also be used with an electronic health records system that maintains health records associated with a plurality of patients including the specific patient, the method further including identifying at least another data operation associated with the at least one intent and executing the another data operation on the specific patient's health record to generate additional response data.

In at least some cases the step of using the first set of response data to generate an audible response file can include using the response data and the additional response data to generate the audible response file.

In at least some embodiments, a method of audibly broadcasting responses to a user based on user queries about a specific patient's molecular report, the method for use with a collaboration device that includes a processor and a microphone and a speaker linked to the processor is provided by the disclosure. The method includes storing a separate molecular report for each of a plurality of patients in a system database, storing a general cancer knowledge database that includes non-patient specific data about cancer topics, receiving an audible query from the user via the microphone, identifying at least one intent associated with the audible query, identifying at least a first data operation associated with the at least one intent and the specific patient's molecular report, identifying at least a second data operation associated with the at least one intent and the general cancer knowledge database, accessing the specific patient's molecular report and the general cancer knowledge database, executing the at least a first data operation on a first set of data included in the specific patient's molecular report to generate a first set of response data, executing the at least a second data operation of the general cancer knowledge database to generate a second set of response data, using at least one of the first and second sets of response data to generate an audible response file, and broadcasting the audible response file via the speaker.

In at least some embodiments, a method of audibly broadcasting responses to a user based on user queries about a specific patient's molecular report, the method for use with a collaboration device that includes a processor and a microphone and a speaker linked to the processor is provided by the disclosure. The method includes storing molecular reports for a plurality of patients in a system database, receiving an audible query from the user via the microphone, determining that the audible query is associated with the specific patient, accessing the specific patient's molecular report, determining the specific patient's cancer state from the molecular report, identifying at least one intent from a pool of intents related to the specific patient's cancer state and the audible query, identifying at least one data operation associated with the at least one intent, executing at least one of the identified at least one data operations on a first set of data included in the specific patient's molecular report to generate a first set of response data, using the first set of response data to generate an audible response file, and broadcasting the audible response file via the speaker.

In at least some embodiments, a method of audibly broadcasting responses to a user based on user queries about a patient, the method for use with a collaboration device that includes a processor and a microphone and a speaker linked to the processor is provided by the disclosure. The method includes storing health records for a plurality of patients in a system database and storing a general cancer knowledge database, receiving an audible query from the user via the microphone, identifying a specific patient associated with the audible query, accessing the health records for the specific patient, identifying cancer related data in the specific patient/s health records, identifying at least one intent related to the identified cancer related data, identifying at least one data operation related to the at least one intent, executing the at least one data operation on the general cancer knowledge database to generate a first set of response data, using the first set of response data to generate an audible response file, and broadcasting the audible response file via the speaker.

BRIEF DESCRIPTION OF THE SEVERAL VIEWS OF THE DRAWINGS

FIG. 14 shows two additional collaboration device configurations including a cube shaped configuration and a tablet type configuration;

FIGS. 17A-17C are schematics showing a first through third pages of a pancreatic clinical report that may be printed in hardcopy or accessed electronically via a workstation, pad or smart phone device, etc.;

DETAILED DESCRIPTION OF THE DISCLOSURE

Figure 1:
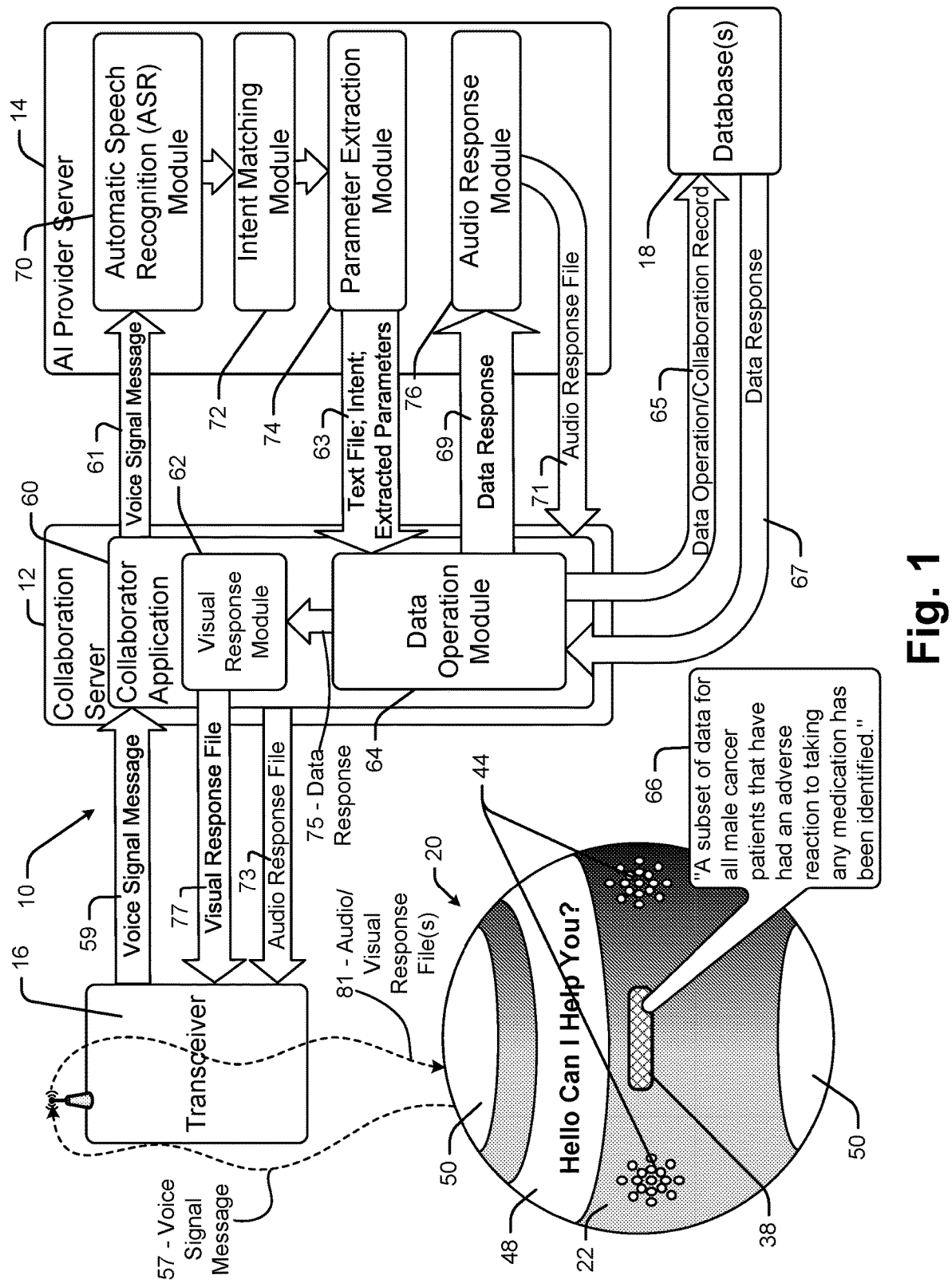
FIG. 1 is a schematic diagram illustrating a collaboration system that is consistent with at least some aspects of the present disclosure that includes a portable wireless collaboration device.

The various aspects of the subject disclosure are now described with reference to the drawings, wherein like reference numerals correspond to similar elements throughout the several views. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

In the following detailed description, reference is made to the accompanying drawings which form a part hereof, and in which is shown by way of illustration, specific embodiments in which the disclosure may be practiced. These embodiments are described in sufficient detail to enable those of ordinary skill in the art to practice the disclosure. It should be understood, however, that the detailed description and the specific examples, while indicating examples of embodiments of the disclosure, are given by way of illustration only and not by way of limitation. From this disclosure, various substitutions, modifications, additions rearrangements, or combinations thereof within the scope of the disclosure may be made and will become apparent to those of ordinary skill in the art.

In accordance with common practice, the various features illustrated in the drawings may not be drawn to scale. The illustrations presented herein are not meant to be actual views of any particular method, device, or system, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or method. In addition, like reference numerals may be used to denote like features throughout the specification and figures.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof. Some drawings may illustrate signals as a single signal for clarity of presentation and description. It will be understood by a person of ordinary skill in the art that the signal may represent a bus of signals, wherein the bus may have a variety of bit widths and the disclosure may be implemented on any number of data signals including a single data signal.

The various illustrative logical blocks, modules, circuits, and algorithm acts described in connection with embodiments disclosed herein may be implemented as electronic hardware, computer software, or combinations of both. To clearly illustrate this interchangeability of hardware and software, various illustrative components, blocks, modules, circuits, and acts are described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the embodiments of the disclosure described herein.

In addition, it is noted that the embodiments may be described in terms of a process that is depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process may correspond to a method, a function, a procedure, a subroutine, a subprogram, etc. Furthermore, the methods disclosed herein may be implemented in hardware, software, or both. If implemented in software, the functions may be stored or transmitted as one or more instructions or code on a computer-readable medium. Computer-readable media includes both computer storage media and communication media including any medium that facilitates transfer of a computer program from one place to another.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

As used herein, the terms "component," "system" and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components may reside within a process and/or thread of execution and a component may be localized on one computer and/or distributed between two or more computers or processors.

The word "exemplary" is used herein to mean serving as an example, instance, or illustration. Any aspect or design described herein as "exemplary" is not necessarily to be construed as preferred or advantageous over other aspects or designs.

Furthermore, the disclosed subject matter may be implemented as a system, method, apparatus, or article of manufacture using standard programming and/or engineering techniques to produce software, firmware, hardware, or any combination thereof to control a computer or processor based device to implement aspects detailed herein. The term "article of manufacture" (or alternatively, "computer program product") as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the claimed subject matter.

The term "genetic analyzer" is used herein to mean a device, system, and/or methods for determining the characteristics (including sequences) of nucleic acid molecules (including DNA, RNA, etc.) present in biological specimens (including tumors, biopsies, tumor organoids, blood samples, saliva samples, or other tissues or fluids).

The term "genetic profile" is used herein to mean a combination of one or more variants, RNA transcriptomes, or other informative genetic characteristics determined for a patient from next-generation sequencing. The next-generation sequencing may also be commonly referred to as "massively parallel sequencing."

The term "genetic sequence" is used herein to mean a recordation of a series of nucleotides present in a patient's RNA or DNA as determined from sequencing the patient's tissue or fluids.

The term "variant" is used herein to mean a difference in a genetic sequence or genetic profile when compared to a reference genetic sequence or expected genetic profile.

The term "expression level" is used herein to mean the number of copies of an RNA or protein molecule generated by a gene or other genetic locus, which may be defined by a chromosomal location or other genetic mapping indicator.

The term "gene product" is used herein to mean a molecule (including a protein or RNA molecule) generated by the manipulation (including transcription) of the gene or other genetic locus, which may be defined by a chromosomal location or other genetic mapping indicator.

Referring now to the drawings wherein like reference numerals correspond to similar elements throughout the several views and, more specifically, referring to FIG. 1, the present disclosure will be described in the context of an exemplary collaboration system 10 that is consistent with at least some aspects of the present disclosure. System 10 includes a collaboration server 12, an artificial intelligence (AI) server 14, a user interface collaboration device 20 and a service provider database 18. Referring again to FIG. 1, in the illustrated embodiment AI server 14 is shown as separate from collaboration server 12. Nevertheless, it should be appreciated that in at least some embodiments the functions the two servers may be performed via a single server. Similarly, while exemplary system 10 is described herein as one where specific process steps or functions are performed by server 12 and others are performed by server 14, in other cases division of the functions and steps between the two servers 12 and 14 may be different. Furthermore, in at least some embodiments some of the processes performed by the servers 12 and 14 may be performed by a processor located within collaboration device 20. For instance, in at least some cases, some or most of the processes related to speech recognition, intent matching, parameter extraction and audio response generation performed by AI server 14 may be performed by collaboration device 20. Having at least some of the processes performed by servers 12 and 14 performed on the collaboration device 20 can reduce latency of outputting a generated response by up to two seconds, and will be explained in further detail below.

Collaboration server 12 is linked to a wireless transceiver (e.g., transmitter and receiver) 16 enabling wireless two-way communication between collaboration device 20 and collaboration server 12. Transceiver 16 may be any type of wireless transceiver including, for instance, a cellular phone transceiver, a WIFI transceiver, a Bluetooth transceiver, a combination of different types of transceivers (e.g., including Bluetooth and cellular), etc. Server 12 runs software applications or modules to perform various processes and functions described throughout this specification. In particular, server 12 runs a collaboration application 60 which includes, among other things, a visual response module 62 and a data operation module 64. Server 12 receives user voice queries (hereinafter "voice messages") 59 captured by device 20, cooperates with AI server 14 to identify the meaning (e.g., intent and important parameters) of the voice messages, runs data operations on data in database 18 that is consistent with the voice messages to generate data responses, cooperates with AI server 14 to generate audio response files based on the data responses and, in at least some cases visual response files, and transmits the response files 73, 77 back to collaboration device 20. Device 20 in turn broadcasts 66 an audio response to the user and in cases where there is a visual response suitable for presentation via device 20, generates the visual response in some fashion (e.g., presents content on a device 20 display 48, illuminates a signaling light 50, etc.). The display 48 and/or signaling light 50 may be considered a visual indicator(s).

Figure 2:
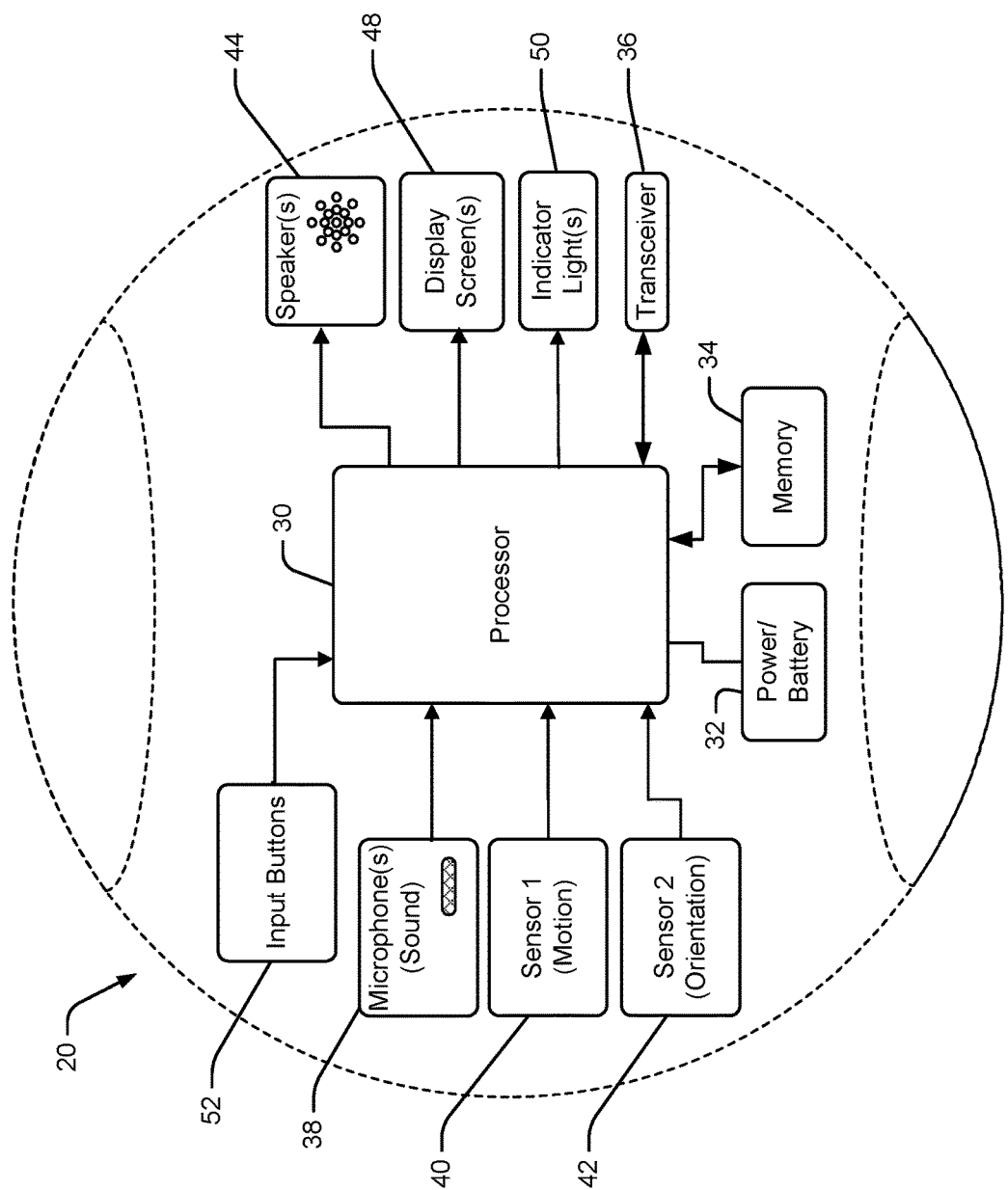
FIG. 2 is a schematic illustrating components of the exemplary collaboration device shown in FIG. 1.

Referring also to FIG. 2, collaboration device 20 includes an external housing 22, a device processor 30, a battery 32 or other power source, a device memory 34, a wireless transceiver 36, one or more microphones 38 and one or more speakers 44 or audio output devices, as well as some component or process that can be used to activate device 20 to initiate a user collaboration activity. External housing 22 includes an external surface that forms a sphere in the illustrated example where a diameter of the sphere is selected so that the device 20 can easily be held by hand by an oncologist. For instance, the diameter of device 20 in most cases will be between three fourths of an inch and five inches and in particularly advantageous embodiments the diameter will be between one and one quarter inch and two inches.

In other cases the external housing includes an external surface that forms a cube or other three-dimensional rectangular prism. In such cases, in particularly advantageous embodiments, the largest dimension of the three-dimensional shape (height, width, depth) will be between one and one quarter inch and two inches.

The system 10 may be implemented in other manners. For instance, the collaboration device 20 may be a smartphone, tablet, laptop, desktop, or other computing device, such as an Apple iPhone, a smartphone running the Android operating system, or an Amazon Echo. Some of the processes performed by the servers 12 and 14 may be performed through the use of an app or another program executed on a processor located within collaboration device 20.

The outside surface may be formed by several different components out of several different materials including opaque materials for some portions of the surface and transparent or translucent materials for other portions where light needs to pass from indicator lights mounted within the housing. The outside housing surface may form speaker and microphone apertures, a charging port opening (not illustrated), and other apertures or openings for different purposes. The housing forms an internal cavity and most of the other device components are mounted therein. While device 20 may include a single speaker and a single microphone, in an optimized assembly device 20 will include several speakers and microphones arrayed about the housing assembly so that oncologist voice signals can be picked up from all directions.

There are many different hardware configurations that may be used to provide the collaboration device processor 30. One particularly useful processor for purposes of the present device 30 is the Qualcomm QCS405 SoC (System-on-Chip) which supports many different types of connectivity including Bluetooth, ZigBee, 802.11ac, 802.11ax-ready, USBC2.0/3.0, and others. This solution includes an on device AI engine that enables on device AI algorithm execution so that, in at least some cases, the AI functionality described herein in relation to server 14 may be performed by processor 30. This SoC supports up to four microphones and supports high performance key word detection. Processor 30 is linked to each of battery 32, memory 34, transceiver 36, microphone 38, and speaker 44. In some embodiments, the battery 32 can be charged using a charging dock (not shown).

Once device 20 is activated and while it remains active, microphone 38 captures user voice messages 57 which are provided to processor 30. Processor 30 transmits 59 the voice messages via transceiver 36 to collaboration server 12 (see again FIG. 1). Audio response files are received 81 back by device 20 transceiver 36 and processor 30 broadcasts those response files via speaker 44. While not shown it is contemplated that device 20 may also include some type of haptic signaling component (e.g., a vibrator or the like) to indicate one or more device states.

The device 20, and more specifically, the memory 34, can include acoustics processes, light control processes, security processes, connectivity processes, and other suitable purposes. These processes can be stored as firmware on a portion of the memory 34 that is non-volatile, and in some embodiments, read-only. The firmware can include acoustics processes that can recognize a library of wake words or phrases the oncologist enunciates. For example, the library can include the phrases "Tempus One" or "Hey ONE." Having key phrases that the oncologist will repeatedly use stored directly on the memory 34 can reduce latency in processing commands the oncologist enunciates. The acoustics processes can also include silence detection processes, fallback audio response playback processes that audibly notify the oncologist of errors or time-outs that occur during data transmissions (e.g., of TCP packets or HTTP messages), speaker protection algorithms, digital signal processing (DSP) algorithms, and/or other suitable processes related to acoustics.

The firmware can include conversational flow processes for determining whether a follow-up question would require the use of a wake word phrase such as "Tempus ONE." For example, an initial question of "What were Dwayne Holder's results?" could be followed by "And how old was he?" without using the "Tempus ONE" wake word phrase or specifying the name of the patient again. The question "And how old was he?" may not be relevant unless the person in question has already been identified, in which case the follow-up question can be asked. The firmware can include battery status algorithms for determining charge levels and/or charge status of the battery 32. The firmware can include connectivity and security processes storing and/or maintaining crypto keys for a secure element, storing device identifiers, storing valid networks (e.g., WiFi networks), and other suitable processes. In some embodiments, the firmware can be updated over the air.

The firmware can also include lighting control processes for controlling the indicator lights 50. The lighting control processes can change the color and/or brightness of the indicator lights 50, as well as pulse the indicator lights 50 on and off.

The firmware processes can be used to control the indicator lights 50 and/or speakers 44 based on a state of the collaboration device 20. Some states are initiated by the oncologist. The oncologist can actuate one or more of the input buttons 52, enunciate commands, and/or move the collaboration device 20 (e.g., by setting the collaboration device 20 on the charging dock). Exemplary lighting and speaker controls based on the state of the collaboration device 20 are included in Table 1 below. Some oncologist interactions include "app" functionality, which will be explained in detail below.

TABLE 1

| CATEGORY | STATE | INDICATOR LIGHT EFFECT | INDICATOR LIGHT COLOR | SOUND | USER INPUT |
|---|---|---|---|---|---|
| POWER | Turn On | Chasing Clockwise 1x | White | Ascending Boot up | Push input button |
|  | Turn Off | Chasing Counterclock 1x | White | Descending Power Down | Push input button |
| CONNECTIVITY | WiFi Pairing | Pulse | Blue |  | Select WiFi Network (in app) |
|  | WiFi Connected | 3 Blips | Blue |  | Success! Notification (in app) |
|  | WiFi Not Connected | Pulse 3x | Red |  | Try Again/ See Troubleshooting |
| QUERY or COMMAND | Wake & Listen | Chasing Clockwise 1x | Blue |  | "Tempus One" |
|  | Query or Command | Solid | Blue |  | Ask question or Giving Command |
| QUERY RESPONSE | Thinking | Fast Pulse | Blue |  |  |
|  | Responding | Solid | Blue | "Answer . . . " |  |
|  | Query Unsuccessful | Solid | Blue | "I'm sorry, please ask again." |  |
| COMMANDS Precede with: "Tempus One, _____" | Volume Up/Down | Solid | White |  | . . . "Volume Up" "Volume Down" "Volume 1-10" |
|  | Stop |  |  |  | . . . "Stop" |
|  | Power Off |  |  |  | . . . "Turn off" "Power off" |
|  | Battery Status |  |  |  | . . . "Battery level" |
| BATTERY | Power On while battery is low | Blink 2x | Red | "Battery Low" |  |
|  | At end of Response while battery is low | Blink 2x | Red | "Battery Low" |  |
|  | Charging on the dock | Breathing pulse | Red (critical low)/White | Short chime when set down | Set on the charging dock |
|  | Fully charged while sitting on dock | Solid | White |  |  |
| ERROR | Any error/alert that needs app intervention | Pulse | Red |  | Consult App |

In at least some cases device 20 can be activated by a specifically uttered voice command. To this end, processor 30 may be on all the time and monitoring for a special triggering activation command like "Hey Query". Once the activation command is received, processor 30 may be activated to participate in a user collaboration session. Here, processor 30 may acknowledge the activation command by transmitting a response like "Hello, what can I help you with?" or a tone or other audio indication, and may then enter a "listening" state to capture a subsequent user voice message. When a subsequent voice message is captured, the collaboration session may proceed as described above.

In addition to or instead of being activated by an uttered activation command, device 20 may be activated by selection of a device activation button or touch sensor, when the device 20 is picked up or otherwise moved, etc. To this end, see the optional input buttons 52 and motion and orientation sensors 40 and 42 in FIG. 2. The motion sensors may include an accelerometer, a gyroscope, both an accelerometer and a gyroscope or some other type of motion sensor device.

In addition to being able to present audio responses to a user's queries, in at least some cases device 20 is equipped to present some type of visual response. For instance in a simple case, device 20 may include more or more indicator lights 50 where LED or other light sources can be activated or controlled to change colors to intricate different device 20 states. For instance, in at least some cases indicator lights 50 may be off or dimmed green when device 20 is inactive and waiting to be activated. Here, once device 20 is activated and while waiting or listening for a voice message, lights 50 may be activated bright green to indicate "go". As a user is speaking and the voice message is being captured by device 20, lights 50 may be activated blue green to indicate an audio message capture state. Once a query voice signal has ended, lights 50 may be illuminated yellow indicating a "thinking" or query processing state. As an audio response is being broadcast to the user, lights 50 may be illuminated orange to indicate an output state and once the audio response is complete, lights 50 may again be illuminated bright green to indicate that device is again waiting or listening for a next voice message to be uttered by the user.

In at least some cases any time device 20 is activated and waiting for a new or next voice message, device 20 may be programmed to wait in the active state for only a threshold duration (e.g., 30 seconds) and then assume an inactive state waiting to be re-activated via another activation utterance or other user input. In other cases, once device 20 is activated, it may remain activated for a longer duration (e.g., 10 minutes) and only enter the deactivated listening state prior to the end of the longer duration if a user utters a deactivation phrase (e.g., "End session", "End query" or "Hey query" followed by "End session") or otherwise affirmatively deactivates the device 20 (e.g., selects a deactivation input button 52).

Referring still to FIG. 2, in some cases, device 20 may include one or more flat or curved or otherwise contoured display screens 48 for presenting visual responses to user queries where the visual responses are suitable for consumption via a relatively small display screen. Here, for instance, short answers to user queries may be presented as text via display 48. As another instance, summary phrases related to data responses that include data that cannot easily be presented via a small display screen may be generated and presented via display 48. Other text phrases or graphics are contemplated for other purposes. For instance, in cases where a visual response is presented via some other display device (e.g., a display device that is paired or otherwise associated with collaboration device 20), a text message may be presented via display 48 indicating that additional information or a visual response is being presented via the associated display. As another instance, display 48 may be controlled to glow specific colors to indicate states as described above with respect to light devices 50 and may only present answers to queries in a textual format. Referring again to FIG. 1, AI server 14 runs software application programs and modules that perform various functions consistent with at least some aspects of the present disclosure. In at least some cases, AI server 14 includes an automatic speech recognition (ASR) module 70, an intent matching module 72, a parameter extraction module 74 and an audio response module 76.

ASR module 70 receives 61 user voice messages from collaboration application 60 and automatically converts the voice signals to text corresponding to the user's uttered voice messages essentially in real time. Thus, if an oncologist's voice signal message is "How many male patients 45 years or older have had pancreatic cancer?" or "What type of treatment should I prescribe this patient?", ASR module 70 generates matching text using speech recognition software. Speech recognition applications are well known in the art and include Dragon software by Nuance, Google Voice by Google, and Watson by IBM, as well as others. In some cases recognition applications support industry specific term/phrase lexicons where specific terms and phrases used within the industries are defined and recognizable. In some cases user specific lexicons are also supported for terms or phrases routinely used by specific oncologists. In each of these cases new terms and phrases can be added to the industry and user lexicons. The text files are provided to intent matching module 72.

Intent matching module 72 includes a natural language processor (NLP) that is programmed to determine an intent of the user's voice signal message. Here, for instance, the intent may be to identify a data subset in database 18. As another instance, the intent associated with the phrase "How many male patients 45 years or older have had pancreatic cancer?" may be to identify a number of patients. As another example, the intent associated with the phrase "What type of treatment should I prescribe patient John Doe?" may be to identify the treatment that the system determines will maximally extend the quality of life for the patient John Doe. Literally thousands of other intents may be discerned by matching module 72. Intents are described in greater detail hereafter.

Referring again to FIG. 1, parameter extraction module 74 extracts important parameters from the user's uttered voice message. For instance, extracted parameters from the phrase "How many male patients 45 years or older have had pancreatic cancer?" may include "pancreatic", "male" and "45 years". For each user voice message, AI server 14 provides 63 (*i*) the associated text file, (ii) the matching intent and (iii) the extracted parameters back to collaboration server 12 and more specifically to the data operation module 64.

Data operation module 64 accesses database 18 and creates 65 a collaboration record on the database to memorialize the collaboration session. The text file received from server 14 is stored in database 18 along with a date and time, oncologist identifying information, etc. Data operation module 64 converts the intent and extracted parameters into a data operation and then performs 65 the operation on data in database 18. For instance, in the case of the voice message "How many male patients 45 years or older have had pancreatic cancer?", operation module 64 structures a database query to search for a number (e.g., the intent) of male patients 45 or older that had pancreatic cancer (e.g., the extracted parameters). The data operation results in a data response including the number of male patients 45 or older that had pancreatic cancer.

As another example, in the case of the voice message "What type of medication should I prescribe for John Doe," operation module 64 structures a database query to search for a medication (e.g., the intent) of a cohort of patients who are clinically similar to the patient John Doe, where such medication resulted in an optimal outcome for the cohort. The determination of whether a cohort of patients is clinically similar may be achieved by querying the database 18 for patients with certain factors, such as age, cancer stage, prior treatments, variants, RNA expression, etc. that are the same and/or similar to those of John Doe. As a simple example, if John Doe has a PTEN genomic mutation, the database 18 may select for inclusion into the cohort all patients who also have a PTEN genomic mutation. As another example, if John Doe has metastatic prostate cancer but no longer responds to androgen suppression first line therapy, the database 18 may select for inclusion into the cohort all metastatic prostate cancer patients who no longer responded to androgen suppression first line therapy.

As another example, in the case of the voice message "What is the expected progression free survival for Jane Smith if I prescribe Keytruda," operation module 64 structures a database query to search for patients clinically similar to Jane Smith; selects from those patients a cohort who were prescribed Keytruda; analyzes the progression free survival of the selected cohort of patients; and returns the average progression free survival from the selected cohort.

As indicated above, the physician's voice message may relate to a question about a particular individual. The operation module 64 may further be arranged to access a patient data repository in order to identify clinical, genomic, or other health information of the patient. The patient data repository may take many forms, and may include an electronic health record, a health information exchange platform, a patient data warehouse, a research database, or the like. The patient data repository may include data stored in structured format, such as a relational database, JSON files, or other data storage arrangements known in the art. The operation module 64 may communicate with the patient data repository in various ways, such as through a data integration, may use various technologies, and may rely on various frameworks, such as Fast Healthcare Interoperability Resources (FHIR). The patient data repository may be owned, operated, and/or controlled by the physician, the physician's employer, a hospital, a physician practice, a clinical laboratory, a contract research organization, or another entity associated with the provision of health care. The patient data repository may include all of the patient's health information, or a subset of the patient's health information. For instance, the patient data repository may include structured data with patient demographic information (such as age, gender, etc.) a clinical description of the patient's cancer (for instance, a staging such as "stage 4" and a subtype such as "pancreatic cancer", etc.), a genomic description of the patient and/or the patient's cancer (for instance, nucleotide listings of certain introns or exons; somatic variants such as "BRAF mutation"; variant allele frequency; immunology markers such as microsatellite instability and tumor mutational burden; RNA overexpression or underexpression; a listing of pathways affected by a found variant; etc.), an imaging description of the patient's cancer (for instance, features derived from radiology or pathology images), an organoid-derived description of the patient's cancer (for instance, a listing of treatments that were effective in reducing or destroying organoid cells derived from the patient's tumor), and a list of prior and current medications, therapies, surgeries, procedures, or other treatments.

The operation module 64 may use various methods to identify how the particular patient being queried about is clinically similar to other individuals whose data is stored in the database 18. Examples of determining clinical similarity are described in U.S. patent application Ser. No. 16/671,165, filed Oct. 31, 2019, the contents of which are incorporated herein by reference in their entirety, for all purposes. Other examples of determining clinical similarity are described in U.S. patent application Ser. No. 16/732,168, filed Dec. 31, 2019, the contents of which are incorporated herein by reference in their entirety, for all purposes.

The determination of what medication resulted in an optimal outcome for an identified cohort of individuals may be determined by comparing the outcome information stored in database 18 for those individuals with the medications that were prescribed or administered to them; dividing the cohort into sub-cohorts; analyzing, for each sub-cohort, measures of outcome such as progression-free survival, overall survival, quality of survival, or so forth; and returning one or more measures that indicate the optimal outcome(s).

In another example, the data operation module 64 may select a first treatment from a list of treatments; examine the information from all patients in the database 18 who were provided that first treatment; divide the patient group into a first cohort of patients with a positive outcome and second cohort of patients without a positive outcome; compare the health characteristics (such as clinical, genomic, and/or imaging) of the queried patient to the health characteristics of the first cohort; compare the health characteristics of the queried patient to the health characteristics of the second cohort; and determine whether the queried patient's characteristics are closer to those of the first cohort or the second cohort. If the queried patient's characteristics are more clinically similar to the first cohort, then the data operation module 64 may prepare a data response indicating the first treatment. If the queried patient's characteristics are more clinically similar to the second cohort, then the data operation module 64 may not prepare a date response indicating the first treatment. The data operation module 64 may then select a second, third, fourth, etc. treatment from the list of treatments and repeat the process described above for each selected treatment, and may continue until all treatments in the list of treatments have been explored. A variety of algorithmic approaches using mathematical or statistical methods known in the art may be used on the relevant health characteristics to determine whether the queried patient characteristics are clinically similar to the first cohort or second cohort, including mean, median, principal component analysis, and the like.

In another example, the data operation module 64 may select all or a subset of records from patients in the database 18. From those records, the module 64 may then select records from a first cohort of patients with a genomic biomarker similar to the queried patient. The module 64 may then filter the first cohort for those patients who were prescribed a first treatment from a list of treatments. The module 64 may then examine the outcomes of the patients in the first cohort and subdivide the first cohort into two or more sub-cohorts based on outcome, with patients with similar outcomes divided into the same sub-cohorts. Each sub-cohort may be further divided like the first cohort into additional sub-cohorts, and so on and so on until there is no material outcomes difference within each sub-cohort. At this point in the method, there may be dozens or more of sub-cohorts. The data operations module 64 may then compare the queried patient's health characteristics with those in each sub-cohort, to identify the sub-cohort that is most clinically similar to the patient's health characteristics. The data operation module 64 may then select a second, third, fourth, etc. treatment from the list of treatments and repeat the process described above for each selected treatment, and may continue until all treatments in the list of treatments have been explored.

Data operation module 64 returns 67 the data response to AI server 14 and, more specifically to audio response module 76, which uses that data to generate an audio response file. For instance, where 576 male patients 45 years or older had pancreatic cancer in the dataset searched, response module 76 may generate the phrase "576 male patents 45 years or older have had pancreatic cancer." The audio response file is transmitted 71 back to collaboration application 60. The collaboration application stores the response file as well as a textual representation thereof in the collaboration record on database 18 for subsequent access. Collaboration application 60 also transmits 73 the audio response file via transceiver 16 to collaboration device 20 which then broadcasts that audio file to the user.

The AI modules 14 may be provided via many different software application programs. One particularly useful suite of software modules that may provide the AI functionality is the Qualcomm Smart Audio 400 Platform Development Kit that can be used with the Qualcomm SoC processor described above. Another useful suite is the Dialogflow program developed and maintained by Google. Dialogflow is an end-to-end, build-once deploy-everywhere development suite for creating conversational interfaces for websites and mobile applications. A system administrator can use Dialogflow interfaces to define a set of intents, training phrases, parameters, and responses to intents. An intent is a general intention (e.g., what a user wants)—by a user to access or manipulate database data in some specific way. For instance, one intent may be to generate a database data subset (e.g., patients that meet qualifying query parameters). As another instance, another intent may be to return a number (e.g., number of patients that meet qualifying parameters). Other intents may be a welcome intent (e.g., when a user first activates device 20), an adverse consequences intent (e.g., to return a list of or at least an indication of adverse consequences to a treatment regimen), a medications intent (e.g., to return a list or indication prior medications), a schedule event intent (e.g., to schedule an appointment, a test, a procedure, etc.), etc. It is anticipated that a typical system will include hundreds and in some cases thousands of intents.

For each intent, the administrator provides a relatively small set of seed or training phrases used to train the intent matching module to recognize an intent associated with a received voice message. The training phrases include phrases that a user might say when their objective or purpose associated with an utterance is consistent with the associated intent. For instance, for an intent to return a number of patients that meet qualifying parameters (e.g., age, ailment, condition, oncogene, mutation, residence, staging, treatment, adverse effects of medical YYY, outcomes, etc.), some exemplary training phrases may be "How many patients have pancreatic cancer?", "How many stage 3 breast cancer patients from Chicago are HER2 positive?", "What number of patients have shown adverse effects while taking medication XXX?", "How many ovarian cancer patients in the last 48 months have had a p85 PIK3CA mutation?", "What percentage of basal cell carcinoma patients in the last 18 months have had cryosurgery?", and "The number of people that smoke that also have lung cancer?" Dialogflow also supports follow up intents that may be serially associated with other intents and more specifically with a second or subsequent intent to be discerned in a series of questions after a first intent is identified. For instance, the first phrase "How many ovarian cancer patients in the last 48 months have had a p85 PIK3CA mutation?" could be followed by a second phrase "How many of those patients were seen in the last 12 months?" As another example, for an intent to return a suggested therapy for a specific patient, some exemplary training phrases may be "What type of medication should I prescribe for John Doe?", "What type of immunotherapy should this patient receive", "What is the expected progression free survival for Jane Smith if I prescribe Keytruda?"

Once a small set of training or seed phrases have been provided by an administrator, a machine learning module (e.g., an AI engine) uses those phrases to automatically train and generate many other similar phrases that may be associated with the intent. This automatic training process by which a large number of similar queries are generated and associated with a specific intent is referred to as "fanning" and the newly generated queries are referred to as "fanned queries". The machine learning module stores the complete set of training and derived phrases (hereinafter "intent phrases") with the intent for use during collaboration sessions. Subsequently as a user uses the system and utters a phrase that is similar to but not an exact match for one of the intent phrases, the intent matching module recognizes the user's intent despite the imperfect match and responds accordingly. In addition, when an utterance is similar to but not exactly the same as one of the intent phrases, the system automatically saves the utterance as an additional intent phrase associated with the intent and may train additional other intent phrases based thereon so that the intention matching module becomes more intelligent over time.

In most cases a system user's intent alone is insufficiently detailed to identify specific information the user is seeking or how to respond and the user has to utter or provide additional query parameters. Dialogflow enables an administrator to specify a set of parameter types to extract from received voice messages. For example, some parameters may include a date, a time, an age, an ailment, a condition, a medication, a treatment, a procedure, a physical condition, a mental condition, etc. For each parameter type, the administrator specifies exemplary parameter phrases or data combinations (hereinafter "parameter phrases") that a system user may utter to indicate the parameter and, again, the machine learning module uses the administrator specified parameter phrases to train a larger set of parameter phrases usable for recognizing instances of the parameter. During a collaboration session when a user query is received, after module 72 identifies intent, extraction module 76 uses the parameter phrases to extract parameter values from the user's voice message and the intent and extracted parameters together provide the raw material needed by data operation module 64 to formulate a data operation to perform on the database 18 data (see again FIG. 1).

Dialogflow allows an administrator to tag some parameters as required and to define feedback prompts to be presented to a user when a received voice message does not include a required parameter. Thus, for instance, if a specific intent requires a date and a query associated with that intent does not include a date parameter, the system may automatically present a feedback prompt to the user requesting a date (e.g., "What date range are you interested in?").

Dialogflow also guides the administrator to define intent responses. An intent response typically includes a text response that specifies one or more phrases, a data response or a formatted combination of text and data that can be used to respond to a user's query. For example, where the intent is to return a number of patients that meet qualifying parameters, a response phrase may be "The number of patients that have _____ is _____.", where the blanks represent data fields to be filled in with parameters from the voice message, data from the database, data derived from the database or options specified in conjunction with the response phrase.

Hereafter an intent and all of the information (e.g., parameters, fanned queries, data operations and answer phrases) related to the specific intent that is specified by the system will be referred to as an intent and supporting information at times in the interest of simplifying this explanation.

In at least some cases, the module 72 can identify at least one intent with a query. In at least some cases, the query can be an audible query. In at least some cases, the at least one intent can be an intent related to a clinical trial. In at least some cases, the at least one intent can be related to a drug. In at least some cases, the intent can be referred to as a drug intent if the intent is related to a drug. In at least some cases, the drug intent can be related to a drug such as chemotherapy. In at least some cases, the drug intent can be an intent related to a PARP inhibitor intent. In at least some cases, the at least one intent can be related to a gene. In at least some cases, the at least one intent can be related to immunology. In at least some cases, the at least one intent can be related to a knowledge database. In at least some cases, the at least one intent can be related to testing methods. In at least some cases, the at least one intent can be related to a gene panel. In at least some cases, the at least one intent can be related to a report. In at least some cases, the at least one intent can be related to an organoid process. In at least some cases, the at least one intent can be related to imaging. In at least some cases, the at least one intent can be related to a pathogen. In at least some cases, the at least one intent can be related to a vaccine.

In FIG. 1, response module 76 uses the response phrases to generate responses and, more specifically, audio response files that are provided back to collaboration server 12. Again, it is contemplated that a typical system may include hundreds or even thousands of response phrases, at least one response phrase format or structure for each intent supported by the system.

In the illustrated exemplary system 10, AI server 14 does not control database 18 and therefore transmits the intent and extracted parameters back to collaboration server 12 which runs data operation module 64. In the present case it is contemplated that many data responses may not be able to be presented to a user in an easily digestible audio response file. For instance, in some cases a data response may include a graphical presentation of comparative cancer data which simply cannot be audibly described in a way that is easy to aurally comprehend. In these cases, after data operation module 64 receives a data response from database 18, module 64 may pass that data on to visual response module 62 which generates a suitable visual response to the user's query which in turn transmits the visual response via transceiver 16 to device 20 for presentation.

In at least some cases summary audio responses may be formulated by the system 10 where appropriate and broadcast via device 20. For instance, in some cases a data response may simply include a list type subset of database data that is to form the basis for additional searching and data manipulation. For example, a sub-dataset may include data for all male cancer patients since 1998 that have had an adverse reaction to taking any medication. This sub-dataset may operate as data for a subsequent query limiting the cancer type to pancreatic or the treatment to treatment XXX or any other more detailed combination of parameters. In these cases where a database subset is limited, an appropriate audio response file may include a summary response such as, for instance, "A subset of data for all male cancer patients that have had an adverse reaction to taking any medication has been identified." (See 66 in FIG. 1.) This response phrase would be specified via the Dialogflow or other conversation defining software applications.

In at least some cases it is contemplated that the system may not be able to associate an oncologist's voice query (i.e., an audible query) with an intent or system supported parameters with a high level of confidence. In some cases it is contemplated that the AI server 14 may be able to assign confidence factors to each intent and extracted parameters and may be programmed to pose one or more probing queries back to an oncologist when intent or a parameter value confidence factor is below some threshold level. In some cases the probing feedback query may be tailored or customized to known structure or data content within the database 18 or intents and parameters supported by AI server 14 to help steer the oncologist toward system supported queries.

In cases where an intent and/or extracted parameters are not supported by the AI server or other system processes, it is contemplated that system 10 will generate a record of the unsupported queries for consideration by an administrator as well as for subsequent access by the oncologist. In these cases it is contemplated that the system will present unsupported queries and related information to an administrator during a system maintenance session so that the administrator can determine if new intents and/or parameters should be specified in Dialogflow or via some other query flow application. In a case where an administrator specifies a new intent and/or parameters, the system may update the collaboration record including the unsupported query to provide a data response to the query and to indicate that the query will now be supported and the oncologist may be notified via e-mail, text, or in some other fashion that the query will be supported during subsequent collaboration sessions.

In some cases, the database 18 may include an electronic health record database from a hospital or a hospital system. In other cases, the database 18 may include an electronic data warehouse with data that has been extracted from an EHR, transformed, and loaded into a multi-dimensional data format. In other cases, the database 18 may include data that has been collected from multiple hospitals, clinics, health systems, and other providers, either across the United States and/or internationally. The data in database 18 may include clinical data elements that reflect the health condition over time of multiple patients. Clinical data elements may include, but are not limited to, Demographics, Age/DOB, Gender, Race/Ethnicity, Institution, Relevant Comorbidities, Smoking History, Diagnosis, Site (Tissue of Origin), Date of Initial Diagnosis, Histology, Histologic Grade, Metastatic Diagnosis, Date of Metastatic Diagnosis, Site(s) of Metastasis, Stage (e.g., TNM, ISS, DSS, FAB, RAI, Binet), Assessments, Labs & Molecular Pathology, Type of Lab (e.g. CBS, CMP, PSA, CEA), Lab Results and Units, Date of Lab, Performance Status (e.g. ECOG, Karnofsky), Performance Status Score, Date of Performance Status, Date of Molecular Pathology Test, Gene/Biomarker/Assay, Gene/Biomarker/Assay Result (e.g. Positive, Negative, Equivocal, Mutated, Wild Type), Molecular Pathology Method (e.g., IHC, FISH, NGS), Molecular Pathology Provider, Additional Subtype-specific data elements (e.g. PSA for Prostate), Treatment, Drug Name, Drug Start Date, Drug End Date, Drug Dosage and Units, Drug Number of Cycles, Surgical Procedure Type, Date of Surgical Procedure, Radiation Site, Radiation Modality, Radiation Start Date, Radiation End Date, Radiation Total Dose Delivered, Radiation Total Fractions Delivered, Outcomes, Response to Therapy (e.g. CR, PR, SD, PD), RECIST, Date of Outcome/Observation, Date of Progression, Date of Recurrence, Adverse Event to Therapy, Adverse Event Date of Presentation, Adverse Event Grade, Date of Death, Date of Last Follow-up, and Disease Status at Last Follow Up. The information in database 18 may have data in a structured form, for instance through the use of a data dictionary or metadata repository, which is a repository of information about the information such as meaning, relationships to other data, origin, usage, and format. The information in database 18 may be in the form of original medical records, such as pathology reports, progress notes, DICOM images, medication lists, and the like.

The database 18 may further include other health data associated with each patient, such as next-generation sequencing (NGS) information generated from a patient's blood, saliva, or other normal specimen; NGS information generated from a patient's tumor specimen; imaging information, such as radiology images, pathology images, or extracted features thereof; other -omics information, such as metabolic information, epigenetic analysis, proteomics information, and so forth. Examples of NGS information may include DNA sequencing information and RNA sequencing information. Examples of imaging information may include radiotherapy imaging, such as planning CT, contours (rtstruct), radiation plan, dose distribution, cone beam CT, radiology, CTs, PETs and the like. The information in database 18 may include longitudinal information for patients, such as information about their medical state at the time of a diagnosis (such as a cancer diagnosis), six month after diagnosis, one year after diagnosis, eighteen months after diagnosis, two years after diagnosis, thirty months after diagnosis, three years after diagnosis, forty two months after diagnosis, four years after diagnosis, and so forth. The information in database 18 may include protected health information. The information in database 18 may include information that has been de-identified. For instance, the information in database 18 may be in a structured format which does not include (1) patient names; (2) all geographic subdivisions smaller than a state, including street address, city, county, precinct, ZIP code, and their equivalent geocodes, except for the initial three digits of the ZIP code if, according to the current publicly available data from the Bureau of the Census: (a) The geographic unit formed by combining all ZIP codes with the same three initial digits contains more than 20,000 people; and (b) The initial three digits of a ZIP code for all such geographic units containing 20,000 or fewer people is changed to 000; (3) All elements of dates (except year) for dates that are directly related to an individual, including birth date, admission date, discharge date, death date, and all ages over 89 and all elements of dates (including year) indicative of such age, except that such ages and elements may be aggregated into a single category of age 90 or older; (4) Telephone numbers; (5) Vehicle identifiers and serial numbers, including license plate numbers; (6) Fax numbers; (7) Device identifiers and serial numbers; (8) Email addresses; (9) Web Universal Resource Locators (URLs); (10) Social security numbers; (11) Internet Protocol (IP) addresses; (12) Medical record numbers; (13) Biometric identifiers, including finger and voice prints; (14) Health plan beneficiary numbers; (15) Full-face photographs and any comparable images; (16) Account numbers; (17) Certificate/license numbers; and (18) Any other unique identifying number, characteristic, or code. The number of records of information in the database 18 may reflect information from 10, 100, 1,000, 10,000, 100,000, 1,000,000, 10,000,000 or more patients. Other examples of the type of information in database 18 are described in U.S. patent application Ser. No. 16/657,804, filed Oct. 18, 2019, the contents of which are incorporated herein by reference in their entirety, for all purposes.

The collaboration device 20 can reduce the amount of private health information that may currently be included in emails sent to oncologists. The collaboration device 20 can delete any generated responses (visual or audio) from the memory 34 after the response is output through the speakers 44. Thus, the private health information may be eliminated from memories outside the database 18. The collaboration device 20 can be configured to recognize a "Can you repeat that" command that causes the collaboration device 20 to re-query the last question that the oncologist asked (e.g., from the collaboration server 12) and once again play back the response and remove it from the memory 34.

Figure 3:
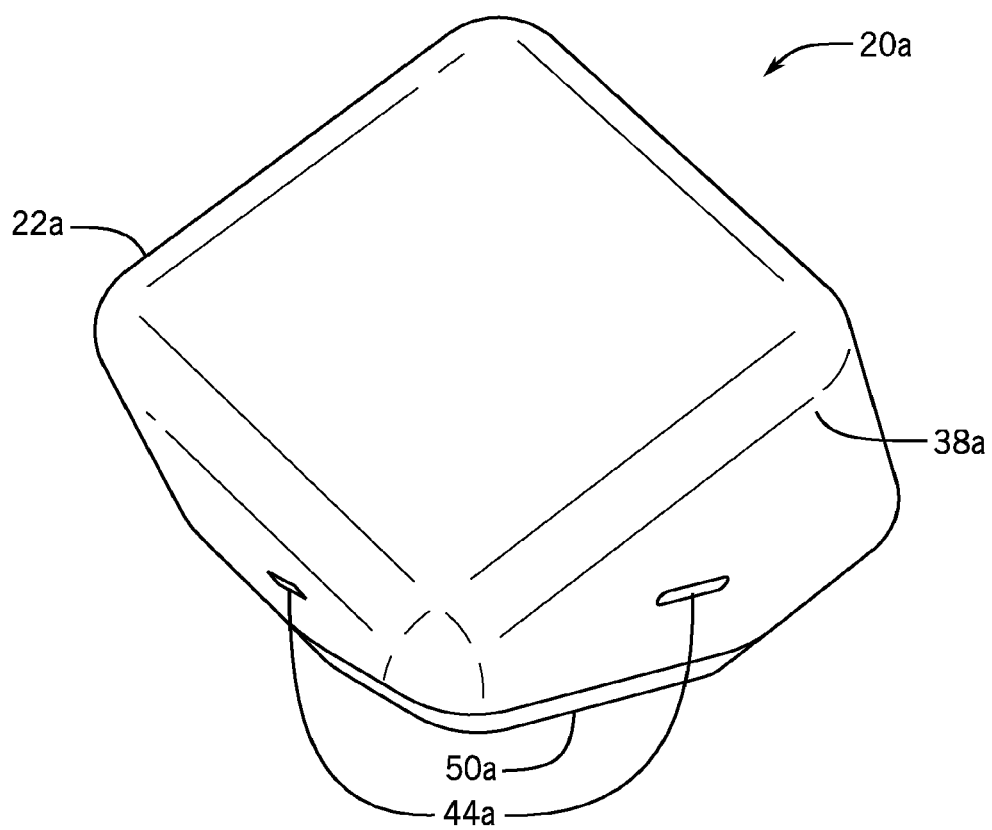
FIG. 3 is a schematic diagram of a second exemplary collaboration device.

Referring to FIG. 2 as well as FIG. 3, an embodiment of an exemplary second collaboration device 20*a* is shown. The collaboration device 20*a* can include a second external housing 22*a* that includes seven substantially flat faces. The collaboration device can include a second light device 50*a*, one or more second microphones 38*a* that can be positioned near small circular openings in the second external housing 22*a*, and second speakers 44*a* that can be positioned near substantially oval-shaped openings in the second external housing 22*a*. In some embodiments, the second external housing 22*a* can be metallic, and may include stainless steel and/or anodized steel. The second collaboration device 20*a* can be about one and a half inches wide, one and a half inches tall, and one and a half inches deep. In some embodiments, the second speakers 44*a* can be headphones coupled to the second collaboration device wirelessly (e.g., via Bluetooth) or via a wired connection (e.g., 3.5 mm jack audio cable.

Figure 4:
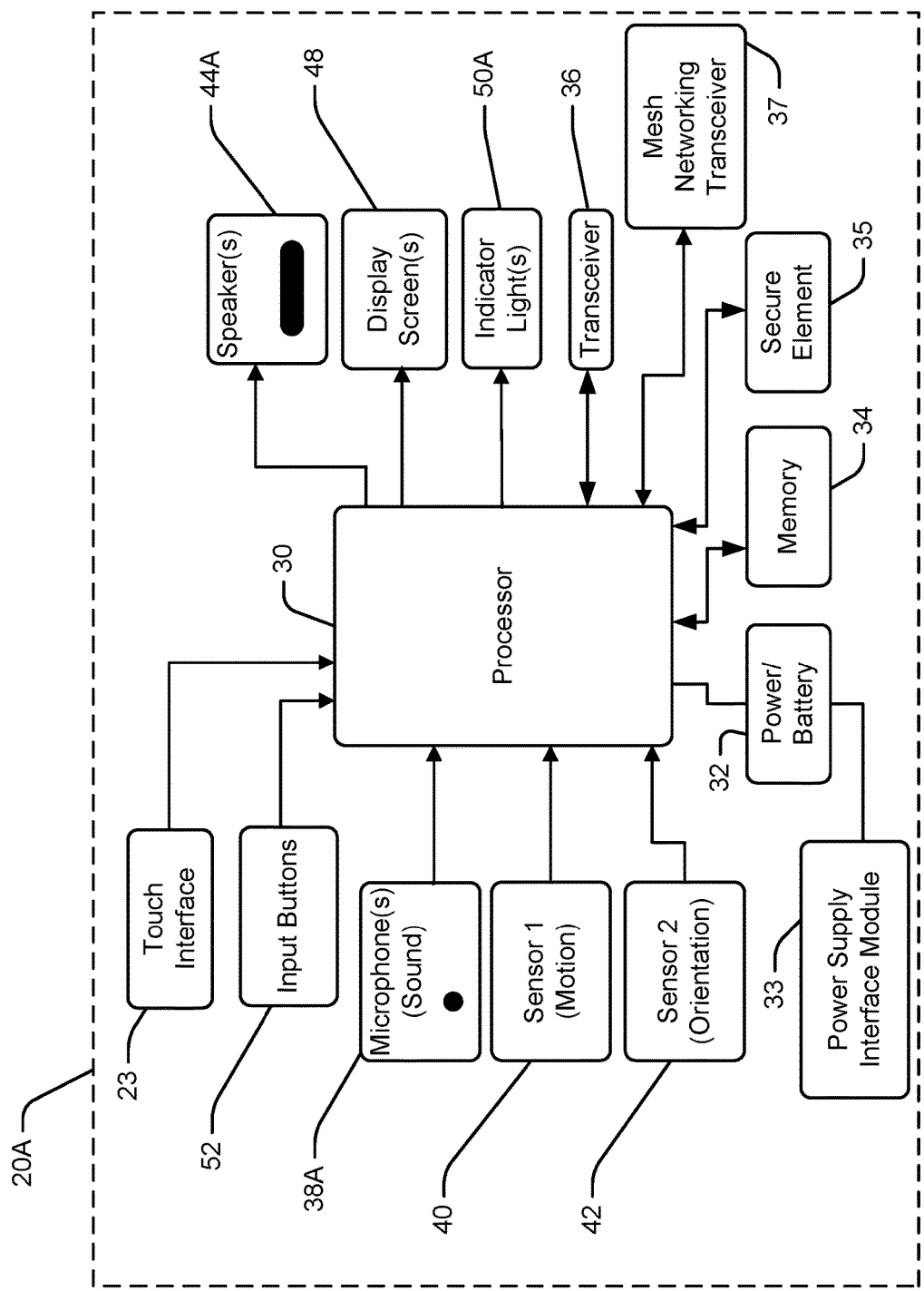
FIG. 4 is a schematic diagram illustrating components of the second exemplary collaboration device shown in FIG. 3.

Referring now to FIGS. 2 and 3 as well as FIG. 4, the second collaboration device 20*a* can include the processor 30 linked to each of battery 32, memory 34, transceiver 36, input buttons 52, display screens 48, and sensors 40, 42 as in the collaboration device 20 described above. The processor 30 can also be linked to the second light device 50*a*, the second microphones 38*a*, and the second speakers 44*a*. The transceiver 36 may be configured to communicate using a 5G cellular network protocol.

The second collaboration device 20*a* can include a touch interface 23 that can receive inputs from the oncologist. The touch interface 23 can be linked to the processor 30. The touch interface 23 can include second external housing 22*a* and sensors (not shown) such as force sensors coupled to the second external housing 22*a*. The sensors can sense deflections of the second external housing 22*a* and output a corresponding signal to the processor 30. In some embodiments, the sensors can include New Degree Technology force sensor film. The second external housing 22*a* can be marked (e.g., engraved) at appropriate locations to identify different sensing areas that may correspond to different virtual buttons (e.g., "power," "ok," "mute," etc.) to the oncologist.

In some embodiments, the touch interface 23 can include one or more touch sensors arranged to receive inputs from the oncologist. The one or more touch sensors may include one or more capacitive touch sensors configured to output signals to the processor 30. In some embodiments, the touch sensors can be positioned under the one or more display screens 48. The processor 30 can prompt the user to provide inputs (e.g., by displaying instructions and/or prompts on the one or more display screens 48 and/or emitting audible instructions at the speakers 44A) and receive signals associated with the oncologist from the one or more touch sensors. The processor 30 may authenticate the oncologist based on the signals by determining if the signals match a predetermined fingerprint profile associated with the oncologist. The processor 30 may determine a selection (e.g., a menu option, a power on/off command, a mute command, etc.) based on the signals.

The second collaboration device 20*a* can also include a power supply interface module 33 coupled to the battery 32 in order to supply power to the battery 32. The power supply interface 33 can include any appropriate hardware for regulating the power supplied to the battery. The power supply interface module 33 can include a hardwired interface (not shown) for connecting to a complementary interface coupled to an external power source. The hardwired interface can include copper or gold contact pins and may be magnetic. Alternatively, the power supply interface module 33 can include one or more transformers (not shown) for receiving power wirelessly. The one or more transformers may include a pot core transformer configured to receive power transmitted at approximately 300 MHz, higher than other wireless charging systems that use standards such as the Qi wireless power transfer standard. Certain wireless charging systems may use coils to implement wireless charging. These wireless charging systems, which may be compatible with the Qi standard, may not be used in the second collaboration device 20*a* due to the small size of the collaboration device 20*a*.In embodiments where the second external housing 22*a* is metallic, care must be taken to ensure the wireless charging does not result in the second external housing 22*a* heating up. The pot core transformer may funnel transmitted energy to the battery 32 to prevent energy from being dispersed in the second external housing 22*a* better than coil transformers.

The second collaboration device 20*a* can include a mesh networking transceiver 37 linked to the processor 30. The mesh networking transceiver 37 may be a WiFi transceiver, a Z-Wave transceiver, a Zigbee transceiver, a combination of different types of transceivers (e.g., including Z-Wave and Zigbee), etc. In particular, the mesh networking transceiver 37 can communicate on a frequency other than one or more of the frequencies used by the transceiver 36 to communicate with the transceiver 16 as shown in FIG. 1.

While the transceiver 36 can be used to communicate with transceivers included in other collaboration devices, the mesh networking transceiver 37 can reduce potential transmission traffic on the communication frequency used by the transceiver 36 to communicate with the transceiver 16. For example, the transceiver 36 can be used to communicate with the transceiver 16 on a 2.4 GHz frequency (e.g., using a WiFi or Bluetooth protocol) and the mesh networking transceiver 37 can be used to communicate with another mesh networking transceiver 37 located in another collaboration device 20*a* on a 900 MHz frequency (e.g., using a Z-Wave protocol).

The transceiver 36 and/or the mesh networking transceiver 37 can be configured to transmit and receive information using ultra wideband (UWB) protocol. UWB may be useful for detecting a real-time location of the second collaboration device 20*a* and/or tracking how the oncologist is operating the second collaboration device 20*a*.

The second collaboration device 20*a* can include a secure element 35 linked to the processor 30. The secure element 35 can perform authentication and encryption tasks such as key storage. The secure element can include an ATECC608A microchip from Microchip Technology Inc.

It is understood that at least a portion of the components included in the second collaboration device 20*a*, such as the touch interface 23, second light device 50*a*, the second microphones 38*a*, and the second speakers 44*a*, the mesh networking transceiver 37, the secure element 35, and the power supply interface module 33, can be included in the collaboration device 20, and may be linked to the processor 30 and/or battery 32. In some embodiments, the processor 30 can be a SoC such as the Qualcomm QCS405 SoC described above. The SoC can be used to implement edge computing as well as machine learning processes locally in the second collaboration device.

Figure 5:
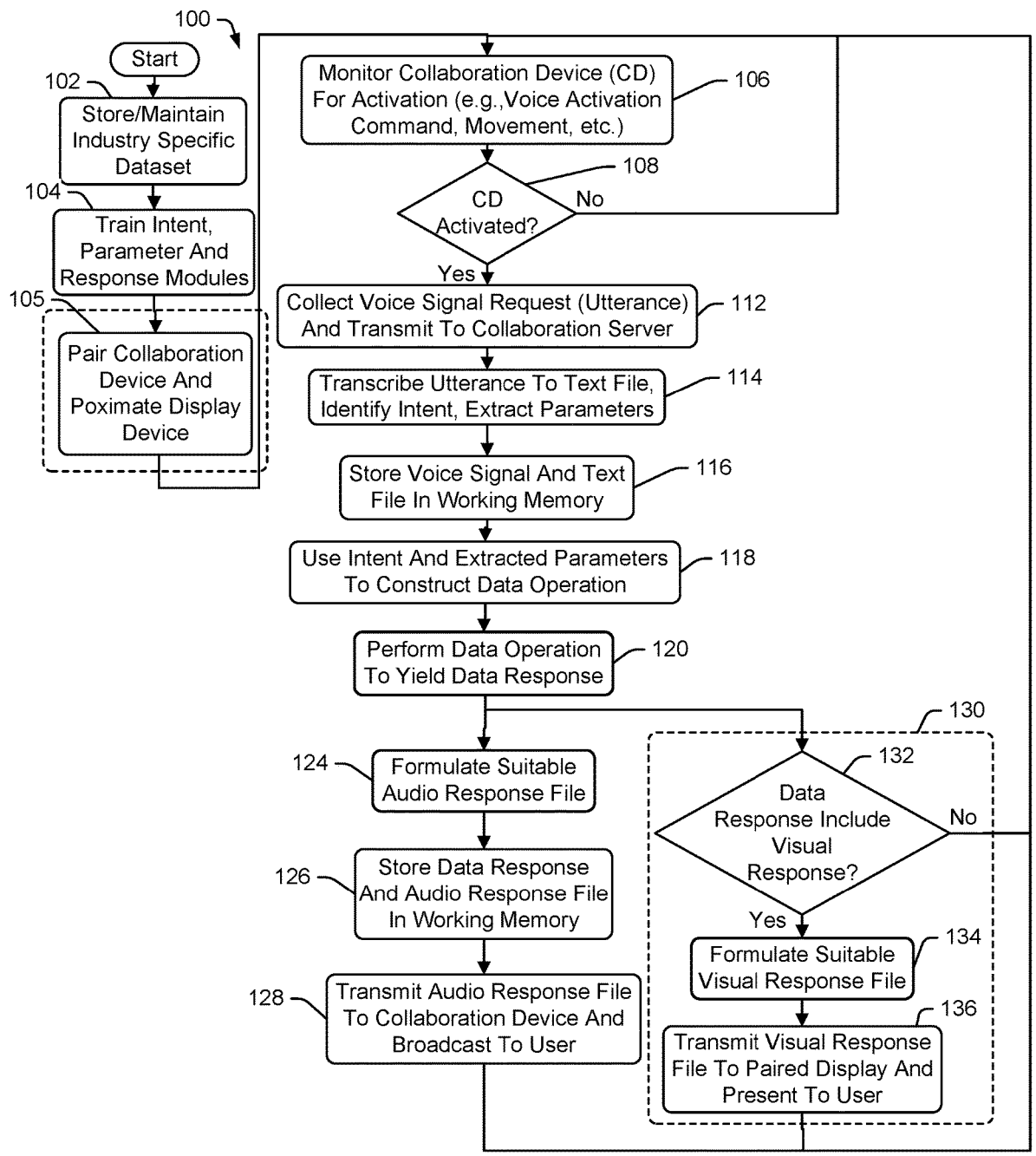
FIG. 5 is a flow chart illustrating a collaboration process that is consistent with at least some aspects of the present disclosure.

Referring now to FIG. 5, a process 100 for facilitating a collaborative session that is consistent with at least some aspects of the present disclosure and that may be implemented via the FIGS. 1 and 2 system is illustrated. Process 100 will initially be described in the context of a system where the only interface device used by an oncologist is the collaboration device 20 (e.g., the system does not include a supplemental or additional large display screen or other emissive surface for presenting additional visual data response representations to a user). In this type of system the portions of process 100 shown surrounded by dashed lines would not be present.

Referring to FIGS. 1, 2, and 5, at process block 102 an industry specific dataset is stored and maintained in database 18. At block 104, the intent matching, parameter extracting and audio response modules 72, 74 and 76, respectively, are trained using Dialogflow or some other conversation defining application as described above. In addition, at block 104 the visual response module 62 is programmed to receive data responses from module 64 where the responses provide seed data for configuring graphical or other visual representations of the response information.

Referring still to FIGS. 1 and 5, in a system only including interface device 20, control passes from block 104 to block 106 where collaboration device 20 monitors for activation (e.g., voice activation, movement, selection of an activation button, etc.). Once collaboration device 20 is activated at block 108, control passes to block 112 where a voice signal is captured by device 20 and the voice signal is transmitted 57 to collaboration server 12. At block 114, the captured voice signal is transmitted 61 to AI server 14 where ASR module 70 transcribes the voice signal to text, intent matching module 72 examines the text file to determine the oncologist's intent, and parameter extraction module 74 extracts key parameter values from the transcribed text. The text file, intent and extracted parameters are passed back 63 to collaboration server 12 and more specifically to data operation module 64.

At block 116, data operation module 64 instantiates a new collaboration record on database 18 and stores 65 the text file in the collaboration record. Operation module 64 also uses the intent and extracted parameters and associated values to construct a data operation at block 118 and that operation is performed at block 120 which yields a data response. At process block 124, operation module 64 provides 69 the data response to AI audio response module 76 which in turn generates an audio response file. The audio response file is sent back 71 to collaboration application and sent 73, 81 to collaboration device 20 at process block 126. The audio response file and related text is stored at block 126 as part of the collaboration record. The audio response file is broadcast 66 via device 20 speakers 44 for the oncologist to hear at block 128 after which control passes back up to block 106 wherein the process continues to cycle indefinitely.

Where a collaboration session persists for multiple rounds of oncologist queries and system responses, each of an oncologist's voice message and associated text and response file and associated text is stored in the collaboration record so that a series of back and forth voice and response messages are captured for subsequent access and consideration.

In at least some embodiments the system also supports a visual output capability in addition to the audio file broadcasting capability to impart process status or state information as well as at least some level of response data in response to user queries. For instance, in FIG. 1, as an oncologist's voice signal is captured by device 20 and AI server 14 generates transcribed text, server 12 may transmit that text file back to device 20 to be presented in real time via display 48 as a feedback mechanism so that an oncologist can ensure that the query was accurately perceived. Here, in some cases, the feedback text may persist until replaced by a visual data response where appropriate (e.g., persists for a few seconds in most scenarios) or may persist for a set duration (e.g., 5-7 seconds). In other cases the feedback text may only be replaced via a next feedback text phrase so that the oncologist has more time to assess accuracy of the perceived utterance.

As another instance, referring still to FIG. 1, where a data response is suitable for visual representation or even optimal if visually represented via device display 48, the data response or a portion thereof may be provided to visual response module 62 as shown at 63. In these cases, module 62 uses the data response to create a visual response file which is transmitted (see 77 and 81) to device 20 to drive display 48. In some cases the visual response presented may include a textual representation of the audio response file. In other cases the visual response may include reminders, alerts, notifications or other user instructions of any type. Where visual files are generated and presented to a user, collaboration server 12 may store all visual representations as part of the ongoing collaboration record for subsequent access.

Figure 6:
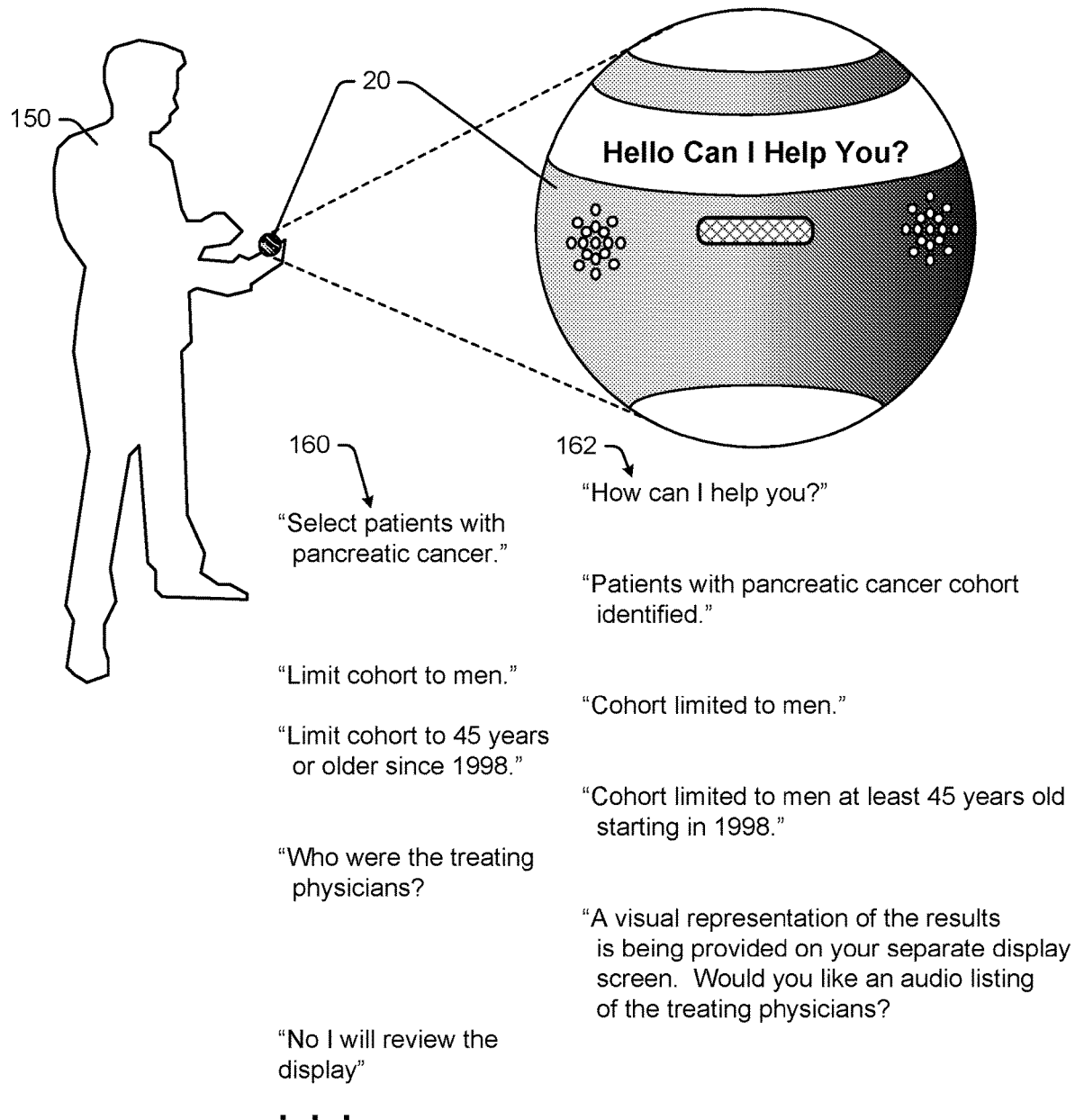
FIG. 6 is a schematic illustrating a collaboration device user having a conversation with the system of claim 1.

Referring now to FIG. 6, an exemplary collaboration conversation between an oncologist 150 and collaboration device 20 is illustrated where oncologist voice messages are shown in a left hand column 160 and interleaved audio responses broadcast by device 20 are shown in a right hand column 162. Once device 20 is activated, device 20 responds with the phrase "How can I help you?" to prompt the oncologist 150 to enunciate a first substantive query of the database 18. Oncologist 150 responds with a first query to "Select patients with pancreatic cancer." Here, consistent with the description above, AI server 14 (FIG. 1) identifies intent and query parameters that are used to construct a data operation which yields a data response and ultimately the audio response "Patients with pancreatic cancer cohort identified." Oncologist 150 then enunciates a second query "Limit cohort to men." causing the system to construct and perform another data operation to yield another audible response. This back and forth "conversation" continues until oncologist 150 ends the session.

In cases where collaboration application 60 stores collaboration records on database 18, the system will enable an oncologist to access those records subsequently to refresh memory, initiate a more detailed line of query aided by additional output affordances such as a large workstation display screen, etc. To this end, see FIG. 7 that shows input and output devices at a workstation inducing a large flat panel display screen 170, a keyboard 172 and a mouse input device 174. Mouse 174 controls an on screen pointing icon 176 for selecting on screen virtual icons and tools as well known in the interface arts. A screen shot on display 170 shows a collaborator window 180 that includes a list of oncologist-system collaborations for a specific oncologist that are selectable to access complete collaboration records. The list includes two columns including a date column 182 indicating the date of a corresponding collaboration session and a collaboration column 184 that includes a first query corresponding toe each collaboration represented in the list. A first entry in column 184 corresponds to the collaboration session illustrated in FIG. 6 and is shown selected via icon 176 and highlighted to indicate selection.

Figure 8:
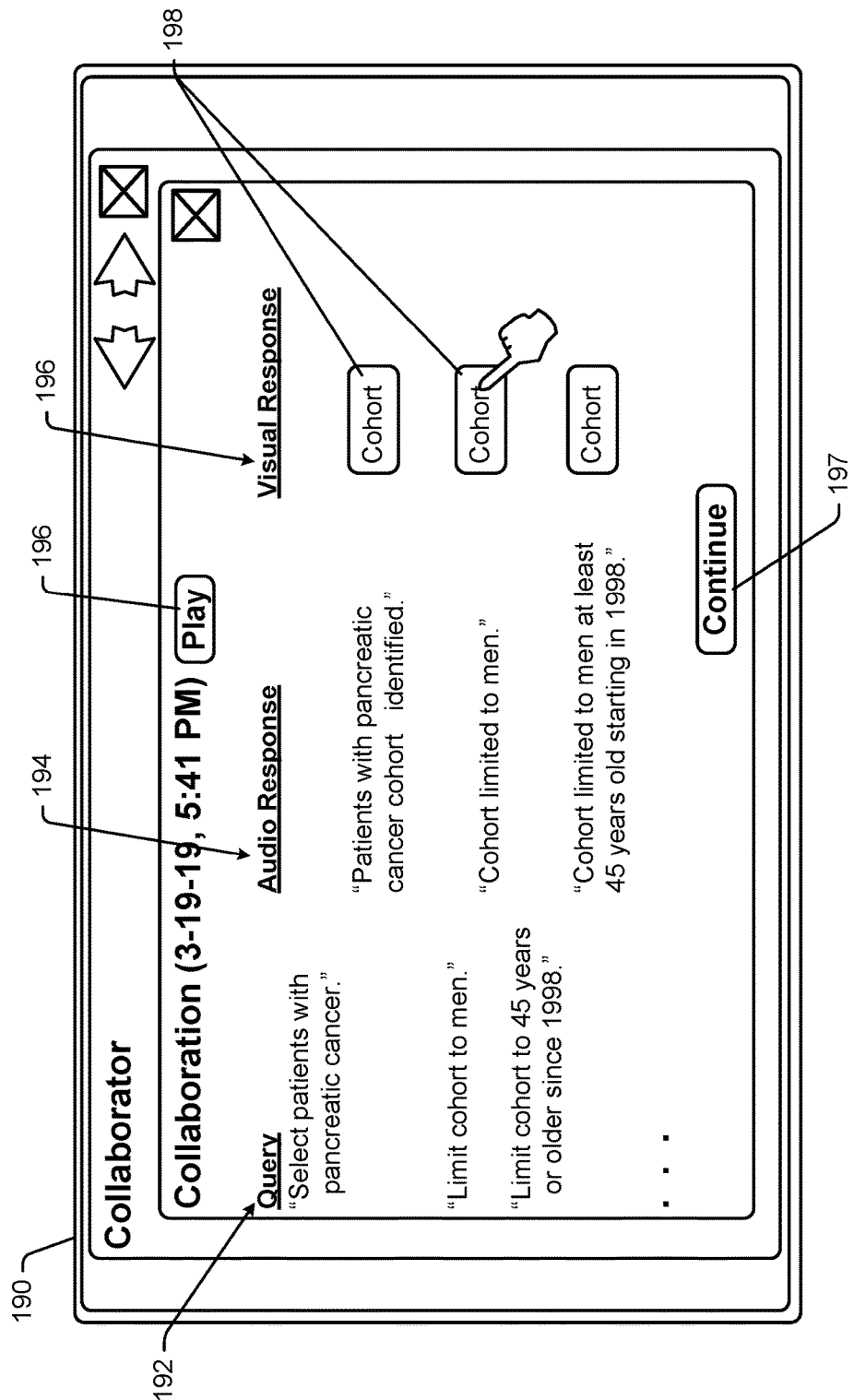
FIG. 8 is similar to FIG. 7, albeit illustrating another screen shot.

When the first entry in column 184 is selected, the screen shot 190 shown in FIG. 8 may be presented that includes the full collaboration record in text with oncologist queries in a first column 192 and the audio system responses represented as text in a second column 194. The example in FIG. 8 corresponds to the conversation in FIG. 6. Here, while the conversation is presented as text, it is contemplated that the oncologist may play an audio recording of the conversation back as a memory aid and to that end, a "Play" icon 196 is provided that is selectable to replay collaboration audio.

Figure 9:
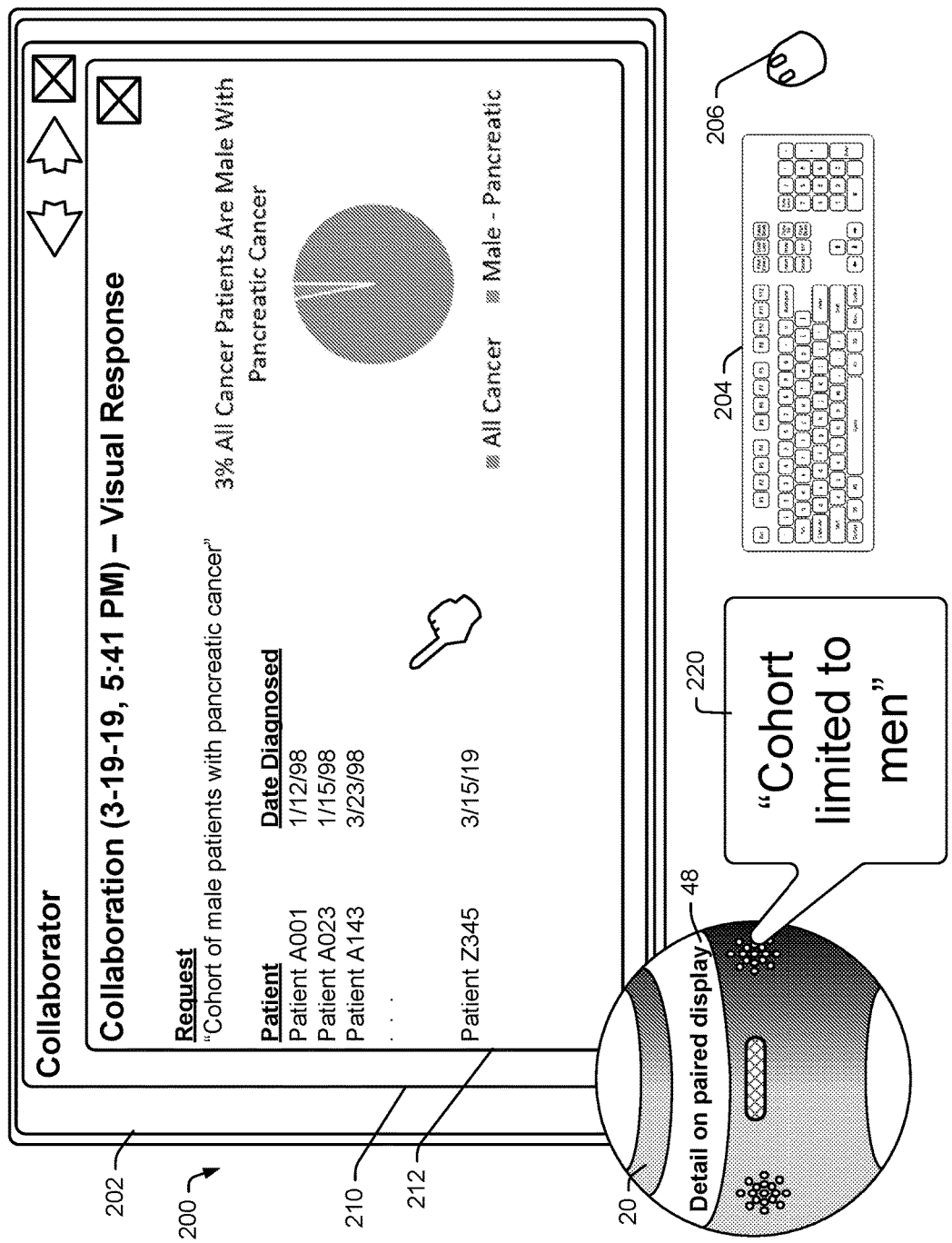
FIG. 9 is a schematic illustrating a portable audible collaboration device being used in conjunction with a workstation including a display.

While collaboration device 20 is advantageous because of its relatively small size and portability, in at least some cases data response presentation is either more suitable via visual representations than audio or audio representations would optimally be supplemented via visual representations on a scale larger than afforded by device display 20. To this end, it is contemplated that portable collaboration device 20 may be supplemented as an output device via a proximate large flat panel display screen when a larger visual representation of response data is optimal. Referring now to FIG. 9, an input/output configuration 200 that may be substituted for the collaboration device 20 in FIG. 1 is illustrated. In FIG. 9, the input/output configuration includes a portable collaboration device 20, a proximate large flat panel display screen 202 and input keyboard and mouse devices 204 and 206, respectively.

Referring still to FIG. 9, in at least some cases device 20 may be programmed to wirelessly "pair" with any Bluetooth or other wireless protocol enabled display screen that is in the general vicinity of device 20 when some pairing event occurs. Here, a pairing event may simply include any time device 20 is proximate a pairable display 202 regardless of whether or not device 20 has been activated to listen for a user's voice signal. In other cases, device 20 may only pair with display once device 20 becomes active (e.g., the pairing event would be activation of device 20). In still other cases, pairing may only occur once device 20 receives a video response file that requires large display 202 for content presentation (e.g., the pairing event would be reception of a video file including data optimally presented on a large display screen).

Regardless of the pairing event, pairing may be automatic upon occurrence of the event or may require some affirmative activity by the user to pair. For instance, affirmative activity may include device 20 broadcasting a voice query to the user requesting authorization to pair with display 202 and a user voicing a "Yes" response in return.

Once device 20 is paired with display 202, an application program run by a display processor may take over the entire display desktop image and present a large collaboration interface via the entire display screen. In an alternative, the application may open a collaborator window 210 as shown in FIG. 9 in which to present visual response files. In FIG. 9, an exemplary visual response representation is shown at 212.

In at least some cases a collaborator window 210 or desktop image may be presented automatically via display 202 when a pairing event occurs. In other cases, even if device 20 pairs with a display 202, collaboration window 210 may not be provided until some secondary triggering event occurs like, for instance, device 20 is activated or a visual response file to be displayed on display 202 is received. In still other cases window 210 may only be presented after a user takes affirmative action to pair device 20 and display 202.

In at least some embodiments, even when device 20 is paired with display 202, response files may only be presented to a user via device 20 at times. For instance, in many cases collaboration server 12 will only generate an audio response file and in that case the audio file would only be broadcast via device 20 with no visual representation on display 202. Here, some user queries may result in response via only device 20, other queries may result in response via only display 152022 and still other queries may result in combined responses via each of device 20 and display 202.

As described above, in at least some embodiments all collaboration system communication with display 202 may be through device 20 so that server 12 does not communicate directly with display 202. In other cases it is contemplated that display 202 will have its own Internet of Things (IoT) address and therefore that server 12 could communicate visual response files directly to display 202. In this case, pairing would require location based association of device 20 and display 202 and storing that association information in a database by server 12 so that audio and visual response file transmission to device 20 and display 202 can be coordinated.

Figure 7:
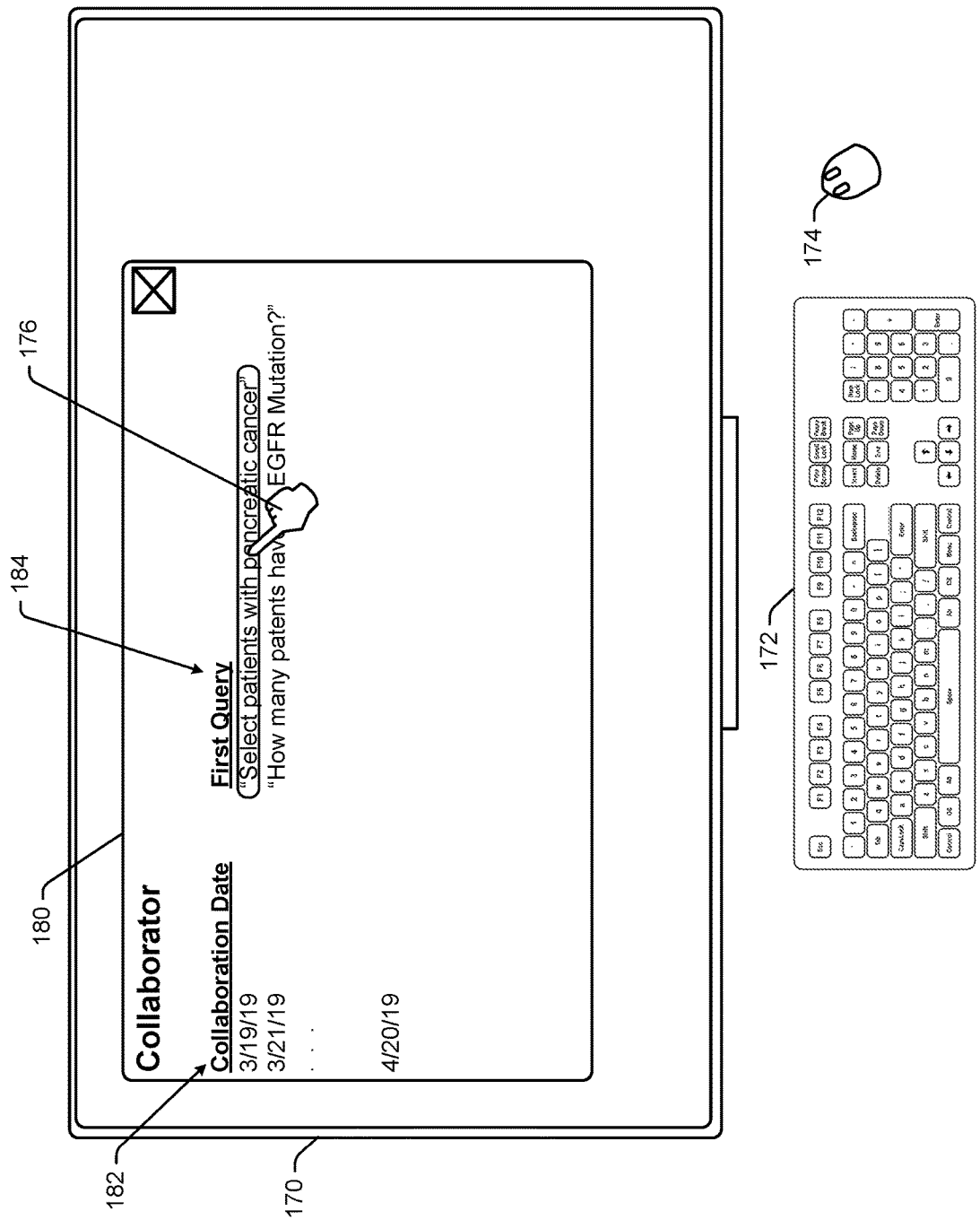
FIG. 7 is a schematic illustrating a workstation usable to access stored collaboration session data.

In at least some cases it is contemplated that when a visual response file is presented on a paired large display 202, a coordinated visual response may be presented via collaboration device display 48 that refers the oncologist to the larger display 202. Similarly, an audio broadcast by device 20 may direct the oncologist to the larger display 202 or include some type of summary message related to the large display 202 visual representation. In FIG. 7, the illustrated audio broadcast 220 summarizes the visual content on large display 202 and device display 48 directs the oncologist to refer to the larger paired display 202 for more detailed information.

In still other cases, when response files would optimally be presented via a large format display while portable collaboration device 20 is remote from a large display so that it cannot pair, the system may notify the oncologist that a better response can be obtained by pairing device 20 with a supplemental large display. Here the notification may be presented via device display 48 or audibly via speakers 44. The notification may be in addition to broadcasting an audio response file with abbreviated response data.

Figure 10:
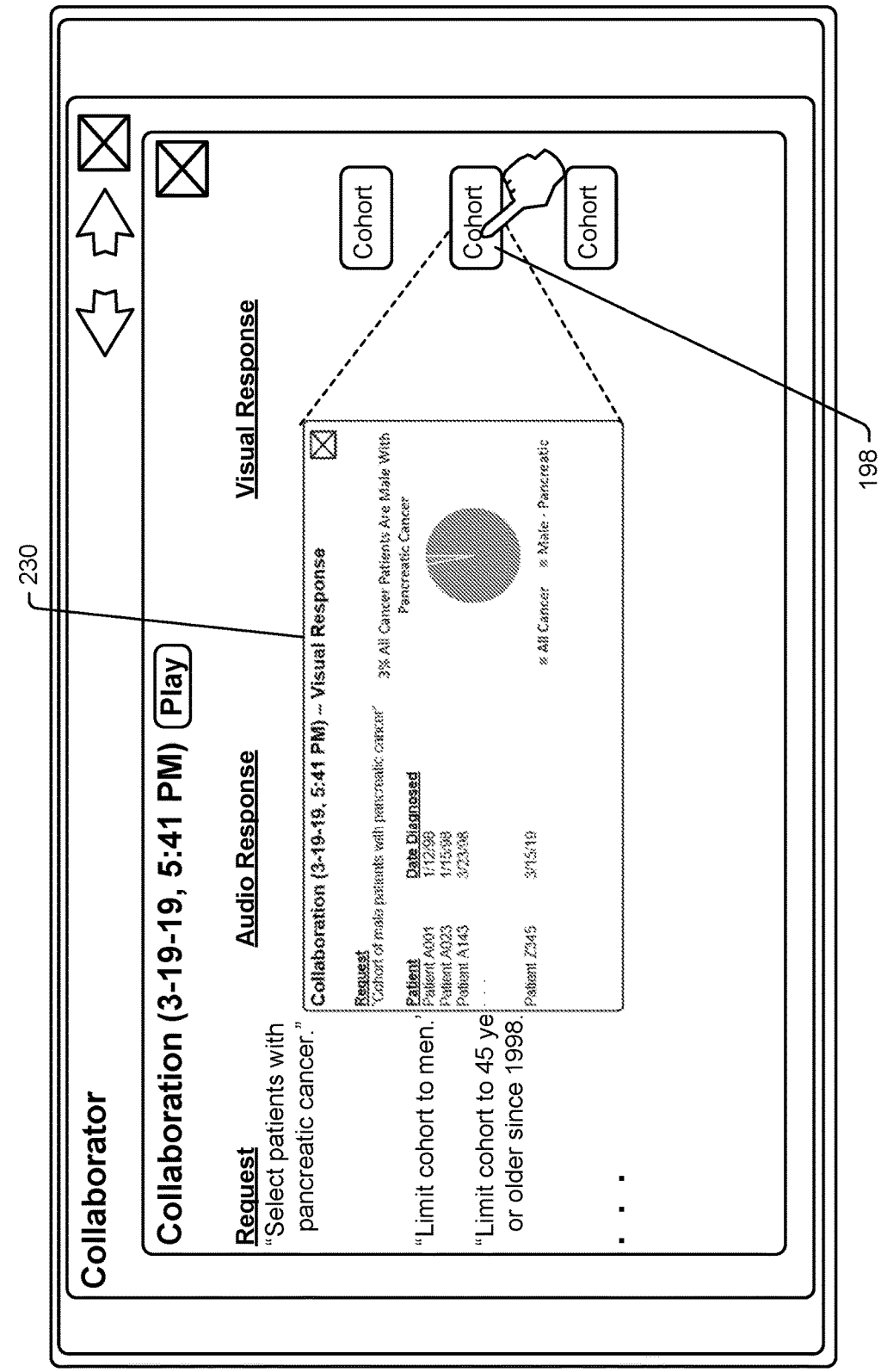
FIG. 10 is a schematic illustrating another screen shot that is similar to the FIG. 8 view.

When system 10 presents visual data via a display screen 202 during a collaboration session, in at least some embodiments all the presented visual files are stored in the collaboration record for subsequent access. To this end see, for instance, FIG. 8 where a third record column 196 include visual response data 198 that corresponds to each of the audio responses in column 194. Here, each visual response is accessible to see information presented visually during an associated collaboration session. FIG. 10 shows one of the visual response icons selected which causes a sub-window 230 to open up and present the visual content that was presented during a prior session.

In at least some cases it is contemplated that system 10 will generate data responses suitable for generating both audio and visual response files which are stored in a collaboration record without presenting any visual information during a collaboration. Here, during a collaboration session all communication is via device 20 despite generation of useful visual response files. The visual information may then be accessed subsequently via an interface akin to the one shown in FIGS. 8 and 10.

Figure 11:
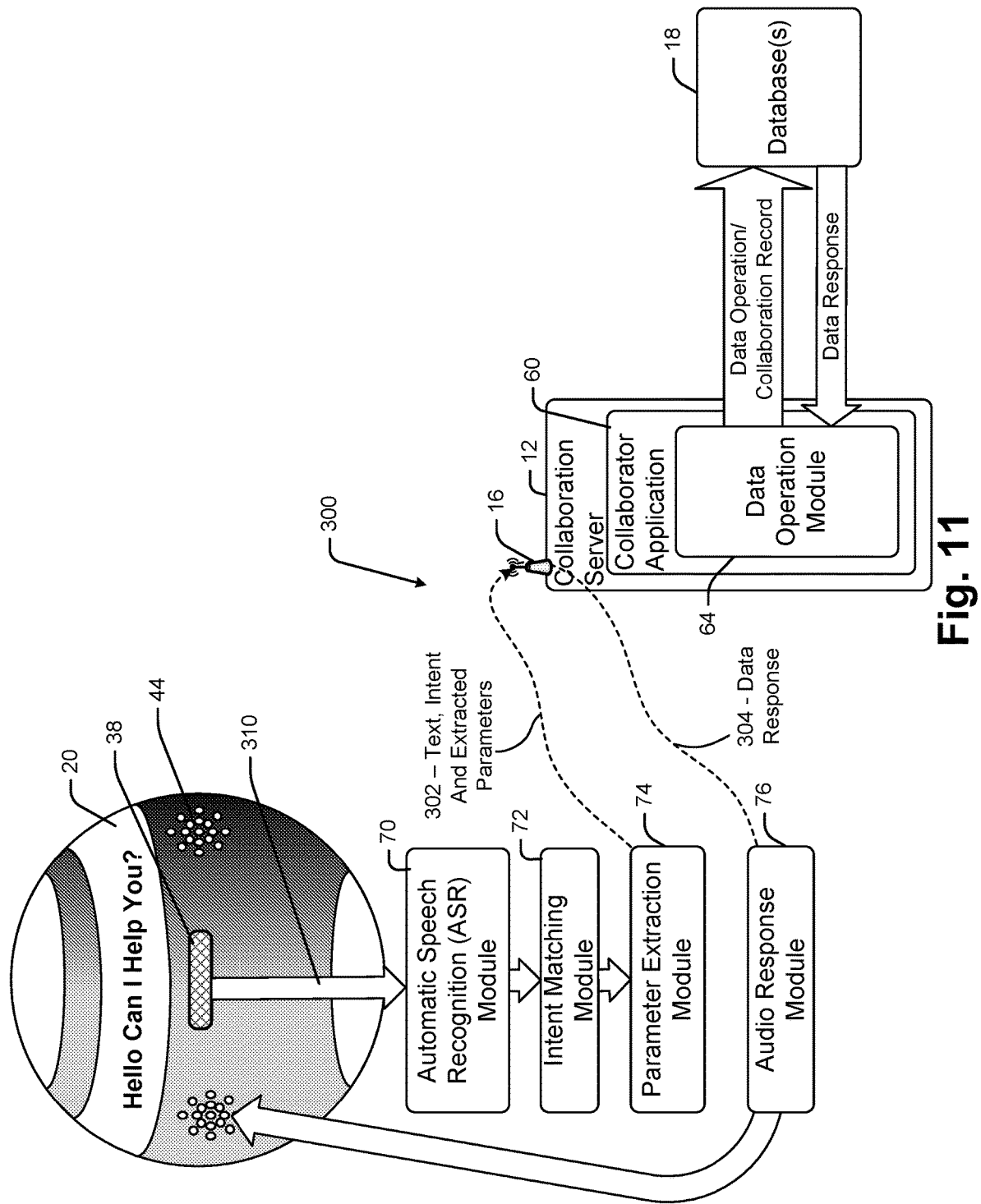
FIG. 11 is a schematic illustrating a second collaboration system that is consistent with at least some aspects of the present disclosure, albeit where a portable collaboration device runs AI applications to generate seed data for data operations and also converts data responses to audio response files to be broadcast via the collaboration device.

Referring now to FIG. 11, a second exemplary system 300 that is consistent with at least some aspects of the present disclosure is illustrated. Here, unlike the FIG. 1 system where AI processes are performed by an independent AI server 14, the AI processes are performed by portable collaboration device 20 which passes information on to collaboration server 12 for fulfillment or performance of data operations. As illustrated, the ASR, intent matching and parameter extraction modules 70, 72 and 74, respectively, are all included in device 20. An oncologist's voice signal captured by device 20 is provided 310 to ASR engine 70 which generates test provided to intent matching module 72. Module 72 identifies the oncologist's intent and then module 74 extracts parameters from the voice signal and each of the text, intent and extracted parameters is wirelessly transmitted 302 via transceiver 16 to collaboration server 12. Server 12 operates in the same manner described above to create and build a collaboration record based on oncologist voice messages and system responses and also to use the intent and parameters to formulate data operations to be performed on database 18 to generate data needed to answer oncologist queries. The data responses are transmitted 304 back to device 20 where audio response module 76 generates an audio file to drive speakers 44 and present the audio response.

Figure 12:
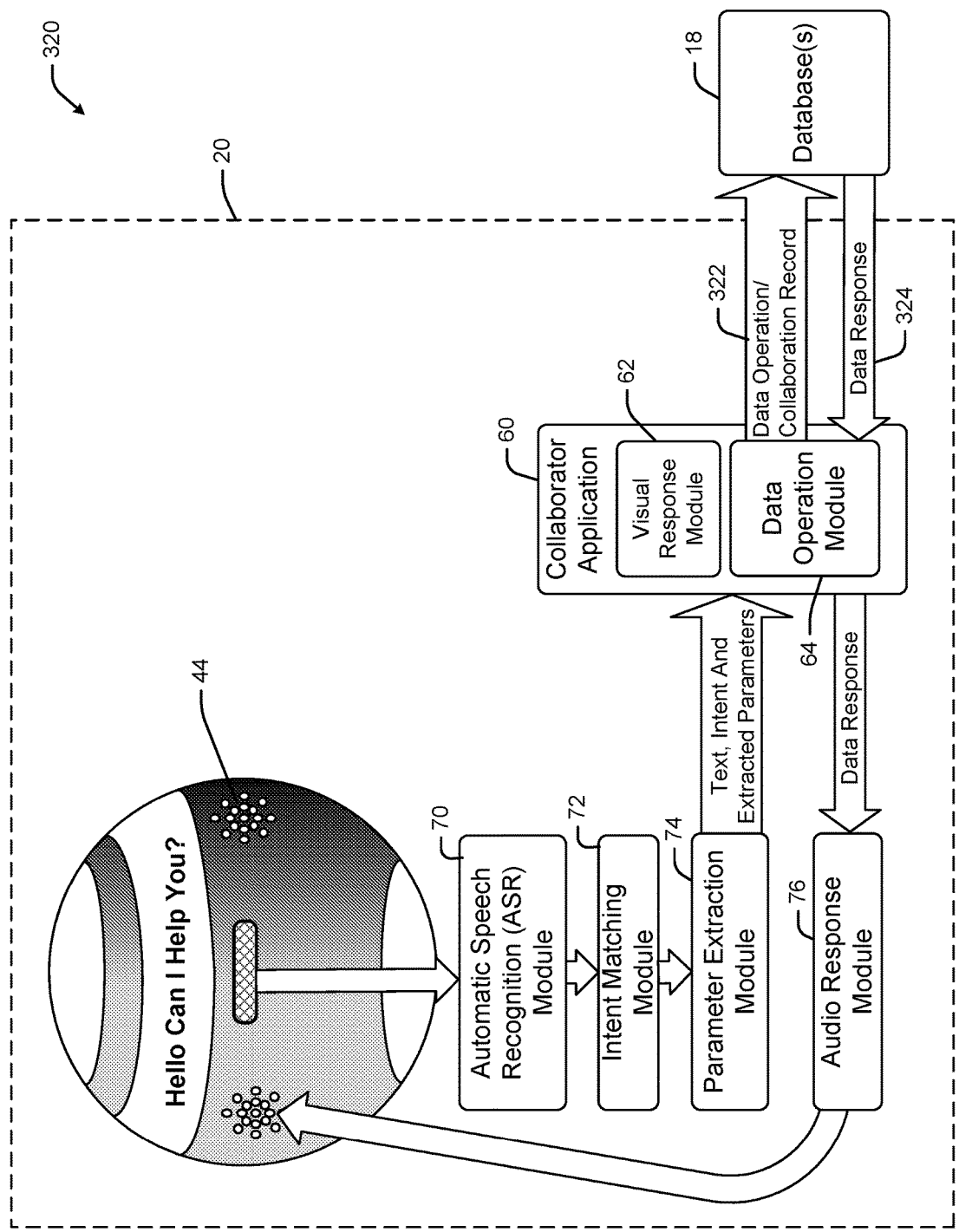
FIG. 12 is a schematic illustrating a third collaboration system that is consistent with at least some aspects of the present disclosure.

Referring now to FIG. 12, a third exemplary system 320 that is consistent with at least some aspects of the present disclosure is illustrated. Similar to the second exemplary system 300 shown in FIG. 11, the AI processes performed by the independent AI server 14 are performed by portable collaboration device 20. Unlike the second exemplary system 300, the processes performed by the independent collaboration server 12 are performed by portable collaboration device 20. The collaboration device is linked to the database 18 in order to send data operations 322 to the database 320 and receive data response 324 from the database 18. The collaboration device 20, and more specifically the audio response module 76, then generates an audio file to drive speakers 44 and present the audio response as described above.

Referring to both FIGS. 9 and 12, having at least a portion of processes performed by the AI provider server 14 and the collaboration server 12 implemented locally in the collaboration device 20 can reduce latency of generating audio response by up to two seconds. In some embodiments, at least a portion of the modules 62, 64, 70, 72, 74, 76 and/or the collaborator application 60 can be stored in the collaboration server 12 or the AI provider server 14 and periodically updated and pushed to the collaboration device 20. In other words, the collaboration server 12 or the AI provider server 14 can store the most current versions of the modules 62, 64, 70, 72, 74, 76 and/or the collaborator application 60 and periodically (e.g., once per day or week) update the processes stored on the collaboration device 20 to include the processes of the most current modules 62, 64, 70, 72, 74, 76 and/or the collaborator application 60 stored on the collaboration server 12 or the AI provider server 14. In this way, the processes executed by the collaboration device 20 can be continually updated while reducing the latency of generating audio responses based on input from the oncologist.

Figure 13:
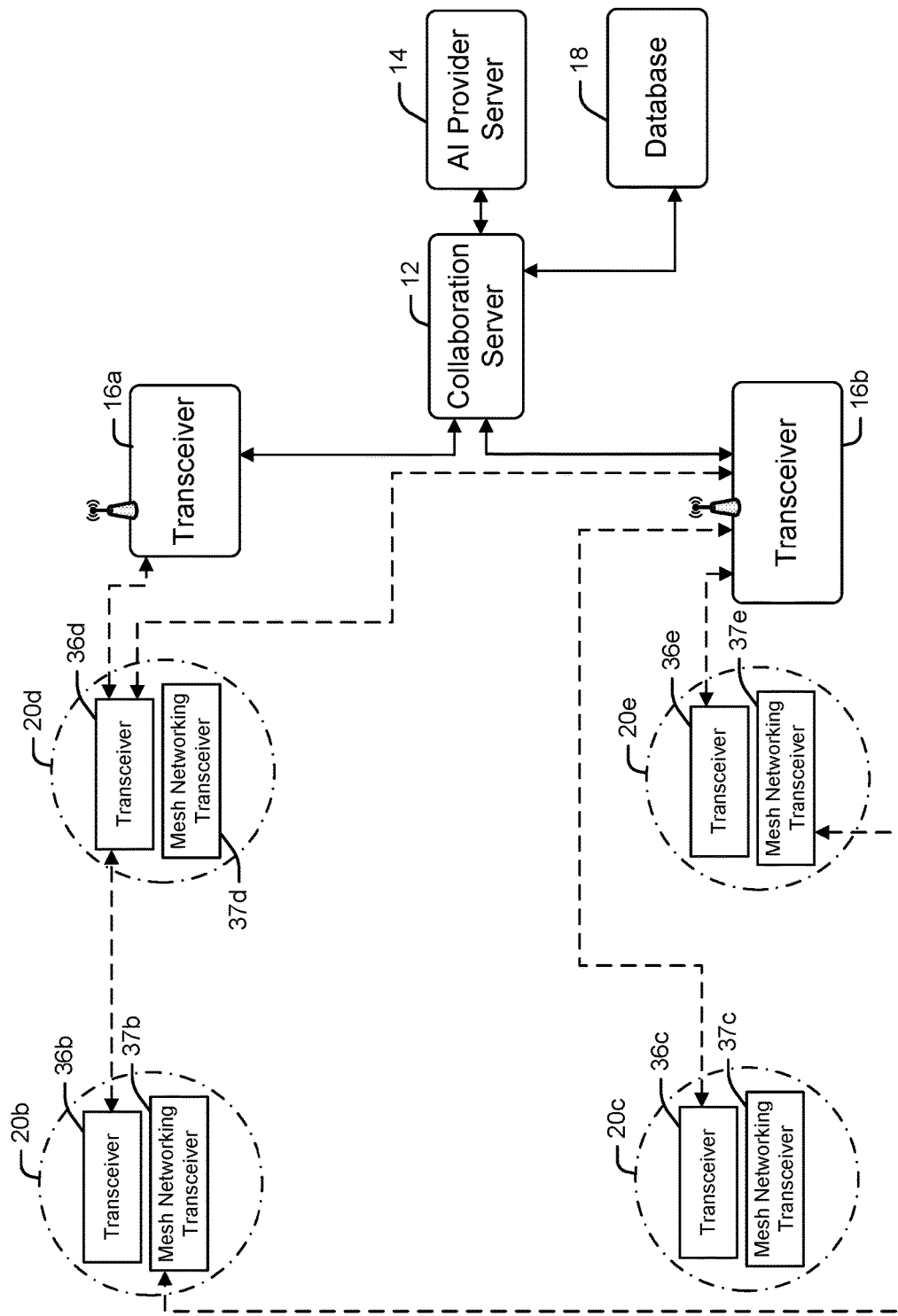
FIG. 13 is a schematic illustrating a number of collaboration devices that can communicate using mesh networking with each other and/or with at least one of a first transceiver and a second transceiver.

Referring to FIG. 13, a number of collaboration devices 20*b-e* can communicate using a mesh networking technique with each other and/or with at least one of a first transceiver 16*a* and a second transceiver 16*b*. The number of collaboration devices 20*b-e* can include a third exemplary collaboration device 20*b*, a fourth exemplary collaboration device 20*c*, a fifth exemplary collaboration device 20*d*, and a sixth exemplary collaboration device 20*b*. Each of the collaboration devices 20*b-e* can include at least a portion of the components of the collaboration device 20 or the second collaboration device 20*a* described above. In some embodiments, each of the collaboration devices 20*b-e* can be the collaboration device 20 or the second collaboration device 20*a*. While four collaboration devices 20*b-e* are shown, it is understood that more than four collaboration devices can be used. Each of the first transceiver 16*a* and the second transceiver 16*b* can be the transceiver 16 described above.

The number of collaboration devices 20*b-e* can each include a corresponding transceiver 36*b-e*, each of which can be substantially the same as the transceiver 36 described above. Each of the number collaboration devices 20b-e may be linked to the first transceiver 16a and/or the second transceiver 16b in order to transmit voice and message signals to the first transceiver 16a and/or the second transceiver 16b using the corresponding transceiver 36b-e included in one of the collaboration devices 20b-e. For example, the fourth collaboration device 20c can be linked to the second transceiver 16b, the fifth collaboration device 20d can be linked to the first transceiver 16a and the second transceiver 16b, and the sixth collaboration device 20e can be linked to the second transceiver 16b.

The first transceiver 16a and the second transceiver 16b can be linked to the collaboration server 12 to transmit voice signal messages to the collaboration server 12 and receive visual response files and audio response files transmitted from the collaboration server 12 as described above. The collaboration server 12 can be linked to the AI provider server 14 to transmit voice signal messages and data responses to the AI provider server 14 and receive the text files, the matching intent, and the extracted parameters associated with the voice signal messages as well as the audio response files associated with data responses transmitted from the AI provider server 14. The collaboration server 12 can be linked to the database 18 in order to create collaboration records and perform data operations in the database 18, as well as receive data response transmitted from the database 18.

Each of the number of collaboration devices 20b-e can communicate directly with at least one other collaboration devices 20b-e to form a mesh network. The number of collaboration devices 20b-e can communicate with each other using a communication protocol supported by the corresponding transceivers 36b-e, for example WiFi protocol, UWB protocol, and/or Zigbee protocol. Each of the number of collaboration devices 20b-e can also include a corresponding mesh networking transceiver 37b-e, each of which can be substantially the same as the mesh networking transceiver 37 described above.

The number of collaboration devices 20b-e can communicate directly with each other using the corresponding mesh networking transceivers 37b-e, which may reduce transmission traffic on the communication frequency used by the corresponding transceivers 36b-e. The direct connectivity between the collaboration devices 20b-e can be helpful if one of the number of collaboration devices 20b-e cannot communicate with any of the first transceiver 16a or the second transceiver 16b. For example, if the third collaboration device 20b cannot communicate with the transceivers 16a-b, the third collaboration device 20b can route communications through the fifth collaboration device 20d that is linked to the first transceiver 16a in order to transmit voice signal messages and receive transmitted audio and/or visual response files as described herein. Thus, all of the collaboration devices 20b-e can be linked to the collaboration server 12.

The location of each of the number of collaboration devices 20b-e can be determined in order to potentially prevent loss or theft of the number of collaboration devices 20b-e. A monitoring process that may be included on a server in communication with the first transceiver 16a and the second transceiver 16b (e.g., the collaboration server 12) can monitor the location of the collaboration devices 20b-e. The monitoring process can cause heartbeat messages to be transmitted from the transceivers 16a-b to the collaboration devices 20b-e and can receive heartbeat messages transmitted from the collaboration devices 20b-e to the transceivers 16a-b. The monitoring process can then determine the location of each of the collaboration devices 20b-e based on the heartbeat messages.

In some embodiments, each of the number of collaboration devices 20b-e can transmit heartbeat messages at predetermined intervals (e.g., every ten minutes) to the first transceiver 16a and the second transceiver 16b, which may retransmit the heartbeat messages to another device such as the collaboration server 12. In this way, other devices and/or processes such as the collaboration server 12 can track and/or triangulate the location of a given collaboration device (e.g., the fifth collaboration device 20d). In some embodiments, the first transceiver 16a and the second transceiver 16b can be associated with wireless access point MAC addresses that may be associated with GPS coordinates. The monitoring process can then estimate the location of the collaboration devices 20b-e based on the GPS coordinates, which are (indirectly) associated with the transceivers 16a-b. The monitoring process can determine that a given collaboration device (e.g., the third collaboration device 20e) transmitted heartbeat messages to both transceivers 16a-b, and estimate the location of the given collaboration device based on the GPS locations associated with the transceivers 16a-b. The GPS coordinates and/or MAC addresses can be stored in the collaboration server 12.

If the heartbeat message transmitted by one of the number of collaboration devices 20b-e is not received by both the first transceiver 16a and the second transceiver 16b, the monitoring process may determine that the device is lost and notify a system administrator and/or monitoring process that the device is lost. The first transceiver 16a and the second transceiver 16b may also transmit heartbeat messages to the number of collaboration devices 20b-e in order to verify the device has not been potentially lost or stolen. In some embodiments, if one of the number of collaboration devices 20b-e such as the fifth collaboration device 20d does not receive the heartbeat messages from the transceivers 16a-b at the predetermined interval, the fifth collaboration device 20d may enter a restricted mode that restricts processes that can be executed by the fifth collaboration device 20d and/or lock the fifth collaboration device 20d to help prevent potential tampering with sensitive data.

Alternatively or in addition to using the transceivers 16a-b to track locations of the number of collaboration devices 20b-e, the collaboration devices 20b-e themselves can be used to track each other. More specifically, the one or more collaboration devices 20b-e can track another one of the collaboration devices 20b-e using one or more of the direct connections between collaboration devices 20b-e. One of the collaboration devices 20b-e may communicate directly with another one of the collaboration devices 20b-e using UWB protocol. For example, the third collaboration device 20b can be linked to the fifth collaboration device 20d and the sixth collaboration device 20e. The third collaboration device 20b can send heartbeat messages to the fifth collaboration device 20d and the sixth collaboration device 20e, and in response, the fifth collaboration device 20d and the sixth collaboration device 20e can send heartbeat messages back to the third collaboration device 20b. If the third collaboration device 20b does not receive heartbeat messages back from the fifth collaboration device 20d and the sixth collaboration device 20e, the third collaboration device 20b may enter a restricted mode that restricts processes that can be executed by the third collaboration device 20b and/or lock the third collaboration device 20b to help prevent potential tampering with sensitive data. Additionally, the fifth collaboration device 20d and/or the sixth collaboration device 20*e* may send a notification that the third collaboration device 20*b* has been potentially lost or stolen to at least one of the transceivers 16*a-b*. The transceivers 16*a-b* may transmit the notification(s) to the collaboration server 12 for further processing.

In some embodiments, at least a portion of the processes stored on and executed by the AI server 14 and/or the collaboration server 12 can be stored locally on the collaboration devices 20*b-e*. In these embodiments, the processes stored on and executed by the AI server 14 and the collaboration server 12 can be continually updated, for example, by an external program or internally by the collaboration server 12 and/or the AI server 14. As the processes are updated, the collaboration server 12 and/or the AI server can update the corresponding process stored on the collaboration devices 20*b-e*. The processes, which can include speech recognition, intent prediction, analysis, and/or routing processes, can be updated based on data generated by the collaboration devices 20*b-e*.

For example, the third collaboration device 20*b* and the fourth collaboration device 20*c* may receive voice signal messages with different phrases (e.g., phrases with different word choices) that correspond to the same intent. The AI server 14 can then learn that the different phrases match the same intent and update the associated module (e.g., the intent matching module 72 shown in FIG. 1) accordingly. Some of the collaboration devices 20*b-e* can be located within the same institution (e.g., the third collaboration device 20*b*, the fifth collaboration device 20*d*, and the sixth collaboration device 20*e*), and others can be located in another institution (e.g., the fourth collaboration device 20*c*). In this way, the AI server 14 and/or the collaboration server 12 can be updated based on feedback from multiple oncologists from multiple institutions.

Additionally or alternatively, the processes stored on and executed by the AI server 14 and/or the collaboration server 12 can be updated based on external processes. For example, an administrator can add intents to the AI provider server 14. The AI provided server can then upload updated processes to the collaboration devices 20*b-e*.

After an audible collaboration session, it is often difficult to get back into the same dialog flow at a later time as it is difficult to remember the back and forth communication that comprises the dialog. For this reason, in at least some cases a system will enable a user to reinsert herself into a flow using a display screen like the one shown in FIG. 8. Thus, in FIG. 8, a "Continue" button 197 is presented which is selectable to place the overall system 10 in the state that existed at the end of the session. Here, the "state" means that all the context associated with the line of questioning at the end of the session is reinstated (e.g., subsets of data, qualifying parameters, etc.), so that the oncologist can pick up where she left off if that is desired).

One problem oncologists and doctors in general have is that they need to enter notes into patient records every time they encounter and treat patients. At least some studies have indicated that a typical oncologist spends upwards of 1.5 hours every day memorializing events and thoughts in patent notes. Some oncologists craft record or document notes during patient visits while others wait until they have a break or until they are "off work" to craft notes. Where an oncologist crafts a note while with a patient, the doctor's attention is split between the note and the patient which is not ideal. Where an oncologist crafts a note subsequent to a patient visit, thoughts, observations and findings are often misremembered or captured with less detail.

To address this problem, in at least some cases portable collaboration device 20 may be programmed to "listen" to an oncologist-patient care episode and record at least portions of oncologist and patient dialog essentially in real time as a "raw transcription". In addition, a system processor may be programmed to process the raw transcription data through OCR and NLP algorithms to identify words, phrases and other content with the captured raw voice signals. In at least some cases it is contemplated that a processor may be trained using Dialogflow or some other AI software program to recognize an oncologist's intent from captured words and phrases as well as various parameters needed to instantiate different types of structured notes, records or other documents that are consistent with one or more of the oncologist's intents. In addition, it is contemplated that the processor may be able to take into account other patient visit circumstances when discerning oncologist intent as well as identifying important parameters for specific structured notes, records or documents.

For instance, while speaking with a patient that has pancreatic cancer, the processor may use an oncologist's appointment schedule to automatically identify a patient as well as to access the patient's medical records to be used as context for voice messages captured during a patient visit. As the oncologist and patient speak, the processor may be programmed to discern the oncologist's voice and the patient's voice. Here, over time the processor would train to the oncologist's voice and be able to recognize the oncologist's voice based on tone, pitch, voice quality, etc. and would be programmed to assume that other voice signals not fitting the oncologists belong to the patient.

In at least some cases the oncologist could intentionally indicate a structured note type for the system to generate. For instance, in a simple case, the system may be programmed to generate five different structured note types where each type includes a different subset of 15 different parameters. Here, during Dialogflow training, an administrator may provide five different phrases for each of the five different note types where each phrase is associated with an intent to generate an associated note type. The processor would train on the five phrases for each note type and come up with many other phrases to associate with the note type intent. In addition, during training, the 15 parameter subsets for each note type would be specified. Moreover, a structured note type would be created and stored in a structured note database for use in instantiating specific instances of the note type for specific patient visits. Furthermore, feedback queries for at least required parameters may be developed and stored as in the case of the Dialogflow system described above.

During an oncologist-patient visit, when the oncologist wants the system to generate a specific note type, the oncologist may simply activate device 20 by uttering "Go One" and then a phrase like "Create an instance of the first note type". The processor, recognizing the intent to create an instance of the first note type then listens during the dialog to pick out required parameters to instantiate the instance of the note type. In at least some cases if the system cannot identify some parameter(s) required for the note instance, device 20 may be programmed to query the oncologist for the missing parameter(s). Feedback queries may be generated during a patient visit, immediately after the visit while facts and information about the visit are fresh in the oncologist's mind or at some other scheduled time like a break, a scheduled office hour, etc.

In other cases instead of requiring a physician to voice a specific note type to be created, the system may listen to the oncologist-patient dialog and identify an oncologist's intent from the ongoing dialog without some specific request.

Any of a raw transcription, note, record or other document generated by the system during or associated with a patient visit may be stored in a patient's EMR or any other suitable database. The AI can learn over time from oncologist utterances and become smarter as described above. In addition, a structured note may be presented to an oncologist for consideration prior to or after storage so that the oncologist can confirm the information in the structured record. In cases where an oncologist changes information captured by the system, any change may be provided back to a system processor and used to further train the processor AI to more effectively capture intent and/or parameters in the future.

In at least some cases another document type that the system may automatically generate is a billing document. Again, here, a system processor may "listen" to what an oncologist is saying during a patient visit and may discern an intent that has a billing ramification. At that point the processor may start to listen for other parameters to instantiate a complete billing record or document. In some cases a billing record may be automatically sent to a billing system or may be presented in some fashion to the oncologist to confirm the accuracy of the billing record prior to forwarding.

In still other cases another document type the system may automatically generate while listening to an oncologist is a schedule appointment. Here, again, a processor may be able to discern oncologist intent to schedule an appointment from many different utterances and may then simply listen for other parameters needed to instantiate a complete event scheduling action.

In particularly advantageous systems, a processor may be programmed to listen to an oncologist and automatically identify several simultaneous intents to generate several different types of notes, records or documents, and may monitor oncologist utterances to identify all parameters required for each of the simultaneous intents. For instance, where the processor determines that a billable activity or event is occurring and that an oncologist wants a structured patient visit note generated at the same time, where each of a structured bill and the structured note requires a separate subset of 15 different parameters, the processor would listen to oncologist utterances for all of the parameters to instantiate each of a bill record and a patient visit note. Again, where the system fails to capture required parameters, the processor may generate and broadcast or present (e.g., visually on a display) queries to the oncologist to fill out the required information at an appropriate time.

In some cases it is contemplated that an oncologist may indicate automatic document preferences for each patient visit where the system then automatically assumes an intent associated with each preferred document type and simply listens to the oncologist-patient dialog to identify parameters required to instantiate instances of each of the preferred document types for each patient visit. Thus, for instance, one oncologist may want the system to generate a structured patent visit note and a structured bill record as well as to tee up next visit scheduling options for each patient visit the oncologist participates in. Here, at the beginning of each scheduled patient visit session, the system immediately identifies three intents, a patient visit note intent, a bill record intent and a scheduling activity intent. The system accesses a structured record for each of the intents and proceeds to capture all required parameters for the intents. For the scheduling activity intent, the system may identify specific activities to be scheduled based on captured parameters and then at some appropriate time (e.g., last 5 minutes of the scheduled patient visit), may present one or more scheduling options for the specific activity to the oncologist and patient. Here, the oncologist and patent may accept to reject any suggested activity to schedule or the time(s) suggested for the activity.

In still other cases, after a system processor identifies an intent based on oncologist-patient dialog, the processor may be programmed to broadcast a query confirming the intent. For instance, where the system identifies an intent to generate a patient visit note, the processor may be programmed to broadcast the query "Would you like to have a patient visit note generated for this visit?" Here, an affirmative response would cause the processor to identify a structured note format and proceed to collect note format parameters to instantiate the note.

In at least some embodiments a collaboration device 20 may listen in on all utterances by an oncologist and many oncologists may use devices 20 to capture their utterances and raw voice messages. For instance, the system may capture all of an oncologist's utterances during patient visits, while participating in tumor boards, during office hours, and in other circumstances when the oncologist is discussing any aspect of cancer care. Here, a system processor or server may be programmed to recognize all utterances by an associated oncologist and distinguish those from utterances of others (e.g., patients, other healthcare workers, other researchers, etc.). The processor may store all or at least a subset of the oncologist's raw voice messages/utterances and may process those utterances to identify text, words and phrases, contexts and ultimately impressions of the oncologist. For instance, one impression may be that for a pancreatic cancer patient that initially responded well to medication AAA where the medication is no longer effective, medication BBB should be employed as a next line of attack.

While the system may identify and automatically use discerned impressions in some cases, in other cases the system may be programmed to immediately present perceived impressions to an oncologist and allow the oncologist to confirm or reject the impression. Rejected impressions may be discarded or may be recorded to memorialize the rejection, the rejection itself being an indicator of the oncologist's impressions in general and therefore useful in future analysis. Confirmed impressions would be stored in a system database for subsequent use. In other cases impressions may only be periodically presented to an oncologist for confirmation or rejection.

Oncological impressions may be used as seed data for AI machine learning algorithms so that, over time, the algorithms learn from the impressions and populate databases with new data representing thoughts of the oncologist. The system may be programmed to associate different intents with different thoughts and subsequently, when an oncologist voice utterance is received, associate the utterance with the intent, identify parameters related to the intent and then obtain the oncologist's prior impressions or thoughts and provide a response that is consistent with the prior thought or impression.

In at least some cases where the system collects impressions from many different oncologists, the system may combine impressions and thoughts from multiple oncologists so that all oncologists that use the system have access to responses informed by at least a subset of the impressions and thoughts from an entire group. Here, once the database of impressions evolves, when an oncologist utters a question to her collaboration device 20, the system would again identify an intent as well as required parameters to search the database for answers and may identify one or more impressions of interest to answer the question.

In at least some cases it is contemplated that the system will track efficacy of cancer or other treatments automatically to be used as a quality metric related to oncological impressions. Here, efficacious treatments would be assigned high confidence or other types of factors while low efficacy treatments based on relative efficacy of other treatments for comparable cancer states. Then, when an oncologist queries the system, the system would identify intent and required parameters to generate a structured data query and would return information related to only the most efficacious impressions.

In still other cases, the system may rank specific oncologists based on one or more factors and then present query responses based on or that represent the impressions of only the "top" oncologists. For instance, oncologists may be ranked based on peer reputation, based on treatment efficacy of their patients on a risk adjusted basis or using other methods (e.g., differently weighted combinations of factors). Here, responses would be limited to data related to only top oncologists.

In still other cases it is contemplated that queries may be limited to data and impressions for only specific oncologists. For instance, a first oncologist may desire the impression of a second specific oncologist on a specific cancer state. Here, the first oncologist may limit a query to the second oncologist by specific name. For example, where the first oncologist has been collaborating with device 20 to access information related to a first patient, the first oncologist may simply utter "What would Sue White say?". In this case, a processor capturing the query would recognize the intent for another oncologist's impression, identify Sue White as a defining parameter and then access impressions associated with Sue White and regarding other contextual parameters previously captured and recognized by the system during prior dialog (e.g., patient name, cancer state factors, etc.). The response broadcast or presented to the first oncologist would be limited to data and information associated with Sue White.

In many cases, especially as a system is learning during use, the system will make mistakes and may return information that is not what has been asked for. In some cases it will be clear from a response that the query identified by the system was not what an oncologist intended while in other cases a wrong response may not be facially recognizable from the response. In cases where a response is recognized as wrong reflecting an inaccurately identified query, one issue is that an oncologist has to reutter the query with better enunciation. In at least some cases it is contemplated that if an oncologist rejects a response, the system may automatically attempt to identify a different query that the oncologist intended and a different suitable response. For instance if, upon hearing a response, an oncologist utters "No" or some other rejecting phrase, the system would recognize that response, formulate a different query based on the intent and parameters and then issue a different response.

In some cases in addition to recognizing a wrong response, the response will be usable to comprehend an error in the query identified by the system that led to the wrong response. For instance, if an oncologist asks for some cancer state characteristic of Tom Green and the system returns a response "Tom Brown's characteristic is XXX", the answer is usable to identify that the perceived question was wrong. In this case, to eliminate the need for the oncologist to revoice an entire query, the system may be programmed to allow a partial query where intent and parameters associated with the prior incorrectly perceived query are used along with additional information in the partial query to recognize a different data operation to be performed. Thus, in the above example, the oncologist may respond "No, I meant Tom Green." Here the system would use prior query information including intent (e.g., the characteristic sought) as well as the new parameter "Tom Green" to access the characteristic for Tom Green. The idea here is that the system retains context during a dialog so that oncologists do not have to continually re-voice complex queries that are misperceived by the system and instead can simply provide a subset of information in a next query selected to clear up any misperceptions.

In at least some cases, as indicated above, an answer to a query may not include any telltale signs that the query was misperceived by the system. In some cases it is contemplated that the system will be programmed to provide a confirmation broadcast or other message to an oncologist for each or at least a subset of queries that are uttered so that the oncologist can confirm or reject the perceived query. Confirmation leads to a data operation while rejection would cause the system to either identify a different query or ask for restatement of the query. In still other cases an oncologist may be able to ask the system to broadcast the question (e.g., data operation) that the system perceived for confirmation.

While the invention may be susceptible to various modifications and alternative forms, specific embodiments have been shown by way of example in the drawings and have been described in detail herein. However, it should be understood that the invention is not intended to be limited to the particular forms disclosed. For example, while a sphere shaped collaboration devices is described above, the portable device may take many different forms. For instance, referring to FIG. 14, a second exemplary collaboration device 20a may include a cube shaped device including one or more emissive external surfaces for providing visual content. As another instance, a third collaboration device may include a tablet type device 20b or any other portable device with components suitable to perform the functions described above.

Figure 15:
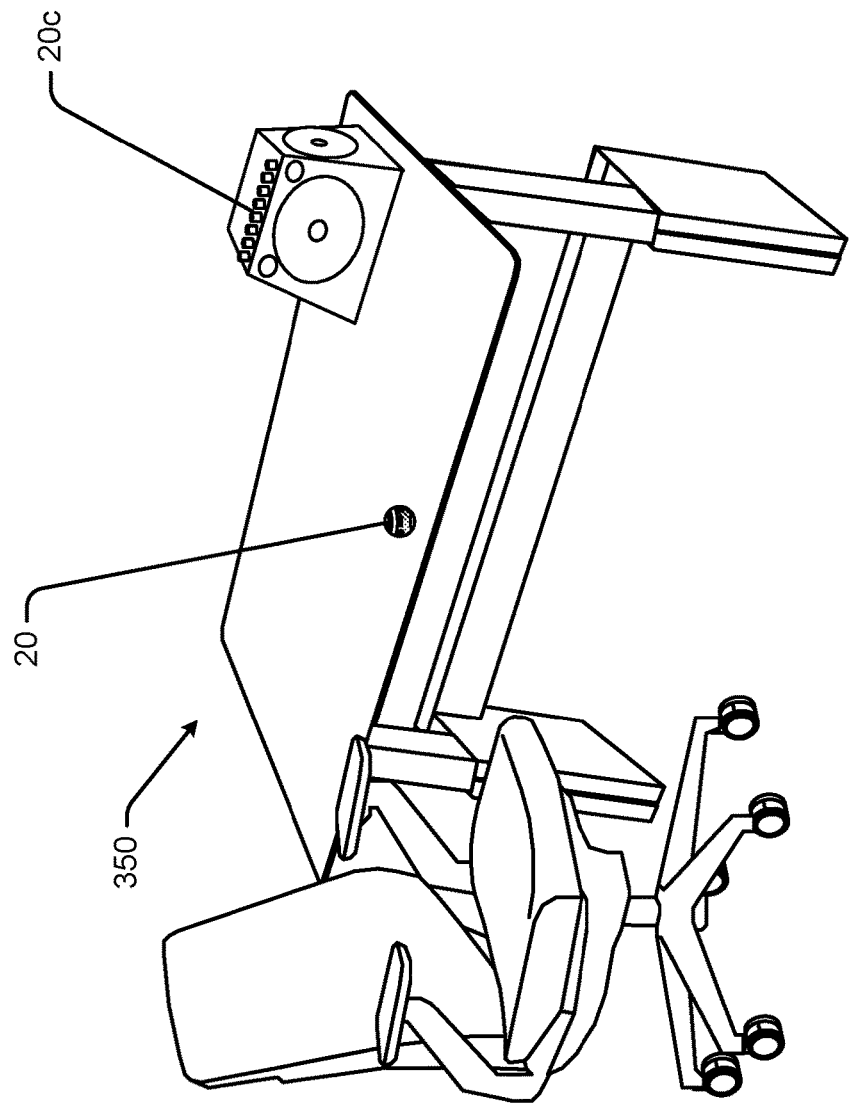
FIG. 15 is a schematic illustrating a workstation that includes various types of input/output collaboration devices.

In still other cases, a portable collaboration device may be one interface device in a larger interface ecosystem that includes other interface devices where an oncologist has the ability to move seamlessly between system interface devices during collaborative sessions. For instance, an ecosystem may include other interface devices and in particular, one or more stationary interface devices with better interface affordances like better microphones, larger speaker components, etc. In this regard, see for instance FIG. 15, which shows another exemplary interface device 20c that is substantially larger than interface device 20 and that is provided for stationary use at a workstation 350. Exemplary interface 20c includes a larger housing structure that forms a cavity for receiving various components as described above with respect to FIG. 2. Here the speakers are larger and presumably would be higher quality than the speakers in device 20. In this case, device 20c is intended to be used at its location on a worktop work surface, on a conference table in a conference room, etc.

In at least some exemplary contemplated systems, devices 20 and 20c may operate in conjunction with each other where collaboration sessions can be handed over from one of the devices 20 to the other 20c to optimize for given circumstances. For instance, if an oncologist is roaming while collaborating via device 20 and enters a space (e.g., arrives at a workstation) that includes a better afforded stationary device 20c, devices 20 and 20c may wirelessly communicate to recognize each other and to coordinate transfer of the collaboration session from device 20 to device 20c. Here, the collaboration session would continue, albeit using the stationary device 20c. Similarly if an oncologist is using device 20c to collaborate and gets up to leave the station, the collaboration session may automatically or with user request or confirmation, be switched over to device 20 so that the collaboration can persist.

Figure 16:
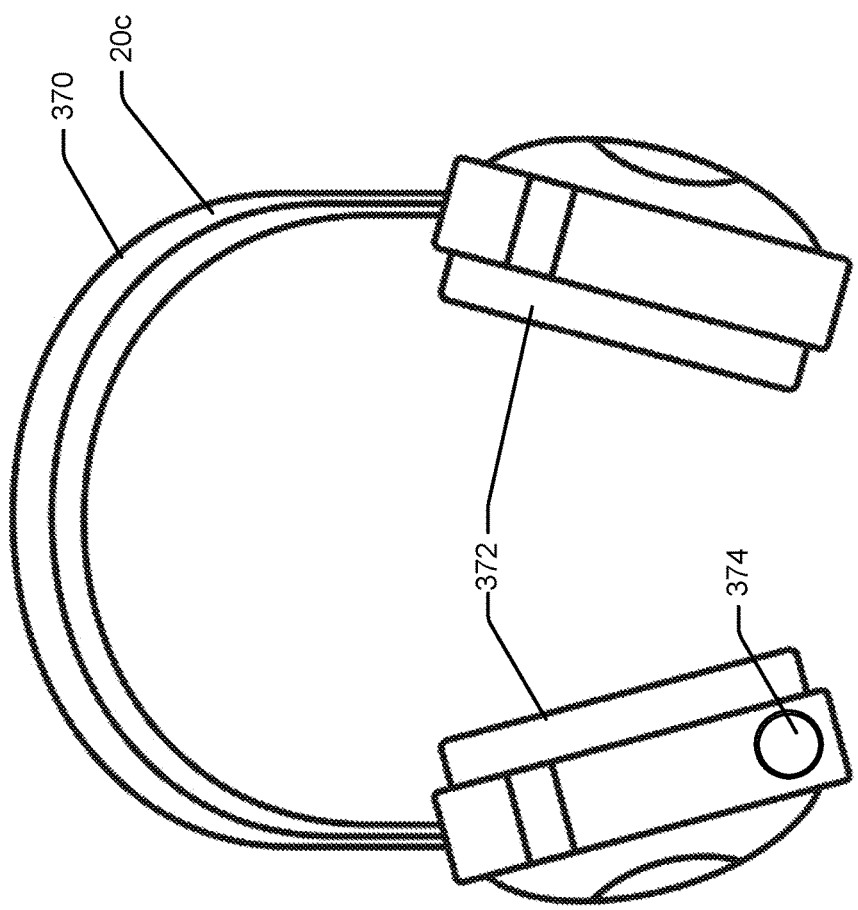
FIG. 16 illustrates a headset that may operate as yet another type of input/output audio interface that is consistent with at least some aspects of the present disclosure.

In still other cases a headphone, smart glasses with speakers and a microphone, etc., may be used as a collaboration device in the disclosed system. In this regard see the exemplary headphone assembly 370 in FIG. 16 that includes ear speakers 372 and a built in microphone 374.

While described in the context of a dedicated collaboration device, aspects of the present invention may also be implemented using any type of computer interface device with microphones and speakers to enable a user-system conversation, regardless of whether or not the device is dedicated only to collaboration or not. For instance, a user's laptop computer may be used as a collaboration device running a collaboration program, an existing voice activated smart speaker may be used as a collaboration device, etc.

While technology or new technology based tools are great when they work well for its intended purposes, when technology or a tool does not work as expected by a user, the user often quickly becomes frustrated and, in many cases simply dismisses the technology or tool reverting back to resources to complete various tasks. This tendency to quickly dismiss imperfect new technology is exacerbated in cases where a user is extremely busy and therefore time constrained. Oncologists tend to be extremely busy people and therefore typically have little tolerance for ineffective or inefficient technology and tools.

One problem with dialog systems like those described herein is that a system that only supports a fraction of queries that oncologists may pose will more often than not fail to identify a correct intent for received queries. Here, in response, the system will either generate an answer to a wrong intent, simply indicate that the system does not currently have an answer for the query posed. These types of imperfect answers would cause frustration and in many cases, ultimately cause oncologists to dismiss these types of collaboration systems entirely.

In at least some embodiments it is contemplated that for a given dataset or record type, an essentially fulsome set of intents/parameters, related database queries and responses will be defined using Dialogflow or some other dialog specifying software so that the system will be able to effectively answer almost any query posed that is related to the dataset. Where new datasets, databases and record types are linked to the system, additional intents and related information may be specified for those datasets, databases and record types. For instance, in at least some cases the system may be programmed to support hundreds of thousands of different intents that include literally any foreseeable intent that may be intended by an oncologist. A team of system administrators/programmers works behind the scenes to identify additional possible intents and to supplement the system with new intents/parameters, related database queries and responses. Additional intents may be based on the existing datasets and record types and/or developed in response to new data types, new information and/or new oncological insights that evolve over time.

In cases where a system supports a massive number (e.g. tens or hundreds of thousands) of different intents, distinguishing one intent from another is complicated as the larger the number of supported intents naturally means that the differences between any intent and a set of similar but different intents will be difficult to discern. The task of correctly identifying an intent is exacerbated in a Dialogflow type system where an AI engine using a query "fanning" process to generate and associate literally hundreds or even thousands of similar queries with a specific intent during system training so that the possibility of fanned queries for two or more different intents overlapping becomes appreciable.

At least some embodiments of the disclosed system will use one or any combination of several techniques to discern an intended intent from other system supported intents. A first technique is based on the system operating during a collaboration session to distinguish different "dialog paths" that occur during the session and information related to a specific dialog path is used to inform subsequent intents during the same dialog path. For example, if a doctor asks device 20 to "give me the results of my patient, Dwayne Holder's, sequencing report" and then asks a subsequent question "what are the best clinical trial options", the system determines that these questions are in a dialog path and answers the clinical trial question based on the clinical trial recommendations that have been provided on Dwayne Holder's clinical report (e.g., the system recommends clinical trials on sequencing reports and the system access all the data in each of those reports). In at least some embodiments only one dialog path is actively followed at a time. Nevertheless, in some cases the system maintains a memory cache of past dialog paths for an oncologist to inform future questions and answers.

A second technique for discerning an intended intent in a system that supports a massive number of intents has the system creating "entities" around key concepts related to an oncologist's query and associated system response(s). For example, Drugs, Drug Regimen, Clinical Trial, Patient Name, Pharmaceutical Company, Mutation, Variant, Adverse Event, Drug Warning, Biomarker, Cancer Type, etc. are all examples of entities supported by an exemplary system. While a small number of entities are identified here it should be appreciated that a typical system may support hundreds of different entities.

In at least some cases the system may be programmed to connect entities in a query or that are identified within a query path to form an entity set which is then usable to narrow down the list of potential answers which may be the best answers to a specific query. For instance, where a query path is associated with patient Dwayne Holder and drug XXX, those patient and drug entities may form a set that limits the most likely intents associated with subsequent queries. The system may also be programmed to leverages entities to evaluate whether a doctor's questions are still part of the same dialog path or if a new question is related to a new topic that is associated with a new dialog path.

A third technique for discerning an intended intent in a system that supports a massive number of intents is referred to generally as "personalization". Here, the idea is that many specific oncologists routinely follow similar dialog paths and voice similar queries with persistent syntax and word choices and therefore, once the system identifies a specific oncologist's persistent query characteristics and correctly associates those with specific intents, subsequent queries with similar characteristics can be associated with the same intents, albeit qualified by different sets of query parameters.

In at least some cases the system builds real time profiles of each oncologist or other system user based on the oncologist's past query characteristics (e.g., word choice, syntax, etc.), query paths followed, prior system provided responses to those queries, oncologist responses to the responses (e.g., does oncologist's response indicate that the system answer and therefore discerned intent was correct), and overall system use. For example, when an oncologist logs into the system, the system may automatically link to a list of the patients that the oncologist has sent to a sequencing service provider, the results that exist in those patients' sequencing reports and the key therapies and clinical trials that have been recommended for those specific patients. These linked lists support the decision making process that the system leverages to determine which question the oncologist is trying to ask (e.g., the oncologist's intent). For example, if an oncologist logs in and recently met with patient named Dwayne Holder, even if the system receives distorted audio that, when converted to text reads like: "what are the results for my quotient Lane Bolder," the system may be programmed to recognize that this oncologist recently met with Dwayne Holder, whose name is similar to Lane Bolder, and would proceed to generate answers based on that recognition.

In particularly advantageous systems all three of the techniques described above are used either serially or in parallel or some combination thereof to discern oncologist query intent. Thus, for instance, the system may use entities to narrow down an oncologist's intent when voicing a specific query, may further narrow down the possible intent based on a current query path and then may select a most likely intent based on a personalization functionality associated with the speaking oncologist.

In at least some cases it is contemplated that the system may provide tools during a system training session to avoid subsequent intent confusion. For instance, assume a system is already programmed to support 100,000 different intents when an administrator specifies a 100,001st intent and three associated seed or training queries to drive an AI engine query fanning process. Here, during the fanning process a system processor may be programmed to compare fanned queries for the 100,001st intent to other queries that are associated with other intents to identify duplicate queries or substantially identical queries. In at least some cases the system may be programmed to automatically avoid a case where fanned queries for two or more intents are identical or substantially identical.

In other cases, when the system recognizes that first and second queries associated with first and second intents are substantially identical, the system may present a warning to the administrator enabling the administrator to assess the situation and how to handle the confusing situation. In some cases substantially identical fanned queries may mean that the system already supports the newly specified intent in which case the administrator may simply forego enabling the new intent. In other cases the administrator may select one of the prior and new intent to be associated with the query in question and in other cases the administrator may allow the fanned query to be associated with two intents. In still other cases the administrator considering the two intents may decide that additional information is required for identifying one or the other or both of the prior and new intents and may further specify the factors to consider when identifying one or the other or both of those intents.

Where a query is associate with two intents, in operation when an oncologist voices the query, the system may identify both intents and generate a response query that is broadcast to the oncologist so that the oncologist can consider which intent was meant. In other cases it may be that both intents are consistent with the oncologist's voiced query and therefore answers to both queries may be generated and sequentially broadcast to the oncologist for consideration.

While the goal of the collaboration system is to handle any question that can be answered using data in system datasets or databases, in at least some cases despite the intent discerning techniques described above, the system may simply be unable to unambiguously identify one intent and/or required parameters associated with an intent among the many intents supported by the system. For instance, in some cases it is contemplated that the system may not be able to identify any intent associated with a query or may identify two or more intents associated with a query. In these cases the system may be programmed to facilitate a triage process to hone in on a specific intent for the query. In this regard, in at least some cases the system may be programmed to generate and broadcast a response query back to the oncologist indicating that the system could not determine the user's intent and requesting that the oncologist restate the query.

In other cases where the system identifies two or more intents that may be associated with the query, the system may broadcast a query to the oncologist like "Did you mean _____?, where the blank is filled in with the first intent and perhaps related parameters gleaned from the initial query. The system may ask about a second or other intents if the oncologist indicates that the first intent was not what was meant.

In cases where the system cannot discern a specific intent from a query or follow-up answers from an oncologist, the system may automatically broadcast a message to the oncologist indicating that the system could not understand the query and indicating that a system administrator will be considering the query and intent so that the system can be trained to handle the oncologist's query. Queries that cannot be associated with specific intents are then presented to an administrator who can consider the query in context (e.g., within a dialog path) and can either associate the query with a specific system supported intent or specify a new intent and related (e.g., required and optional) parameters to be associated with the query. Here, where a new intent is specified, the administrator may specify a small set of additional seed queries for the intent and the system AI engine may facilitate a fanning process to again generate hundreds of additional queries to associate with the new intent. The administrator then specifies one or more data operations on for the new intent as well as an audible response file for generating audible responses for the intent. Upon publishing the new intent, parameters, data operations and response file to the system for use, an e-mail or other notification may be automatically generated and sent to the oncologist that posed the initially unrecognizable query and, in some cases, a suitable answer to that query.

In cases where the system is able to associate a perceived query with a single system supported intent and then performs a data operation to access data needed to formulate an audible answer, in at least some cases the databases and/or records searched will not yield results to drive an answer. For instance, in a case where an oncologist voices a query about a specific patient by name and no information exists in the system databases for that patient, the data operation will not return any data to answer the query. In this case, the system may be programmed to broadcast a message indicating that "There is no data in the system for the patient you identified."

In other cases the system may, in addition to generating data that is directly responsive to a query, generate additional data (hereafter "supplemental data") to supplement the responsive data. Supplemental data can take essentially any type of form that can be supported by data in the system databases and may include, for instance, qualifying statements or phrases that apply to an associated directly applicable response phrase, additional data of interest, clinical trials that may be related to the query, conclusions based on data, and data that supports answer statements.

Here, it is contemplated that supplemental data can be driven by conditional or supplemental data operations or operations that are triggered by the results of a primary data operation, and associated answer phrases and sentences. For instance, a primary data operation that yields data directly responsive to a first query intent may be associated with the first intent and the data from that operation may be used to formulate a directly responsive answer phrase that is directly responsive to an oncologist's query that pairs with the first intent. In addition, a second or supplemental data operation may also be associated with the first intent and may yield data results used to formulate a supplemental answer phrase of some type (e.g., a qualifying statement, additional data of interest in addition to the data that is directly associated with the initial query, clinical trials of interest, conclusions and supporting data, etc.) which, while not directly responsive to the first query, adds additional information of interest to the directly responsive answer phrase. Here, when the primary data operation yields results those results may be used to generate the directly responsive phrase that is responsive to the query. Similarly, when the supplemental data operation associated with the first intent yields results, those results may be used to generate a second or supplemental response phrase. In this case, the directly responsive and supplemental phrases may be broadcast sequentially to the oncologist to hear.

In the above case, if only the primary data operation yields a result and associated directly responsive answer phrase (e.g., the supplemental data operation fails to yield any data that can be used to generate a supplemental response phrase), the system would only generate the directly responsive phrase. Thus, in these cases, the system response to a query may include either a directly responsive phrase alone or a sequence including the directly responsive phrase followed by the supplemental phrase.

In some cases three, four, five or more supplemental data operations and answer phrases may be associated with a single intent in the system. Here, once the intent is identified, every one of the data operations (e.g., primary and each supplemental) may be performed in an attempt to yield results that can be used to generate and broadcast a fulsome system response. Where only a subset of the supplemental data operations generate results, only phrases associated with those results would be generated and sequentially broadcast. Thus, for instance, in a case where a primary and first through fifth supplemental data operations are associated with an intent, if the data operations yield results for the primary, second and fifth supplemental operations, the answer would include three sequential answer phrases, a first for the primary operation results and second and third for the second and fifth supplemental operation results.

A supplemental qualifying statement may be based on an inability to effectively provide a complete answer to a query. For instance, where a primary data operation returns fifty different effective medications for a specific cancer state, instead of broadcasting all 50 medications audibly, the system may simply identify the 3 most effective medications and broadcast those as options along with a qualifying statement that "There are 47 other effective medications, you can say E-mail the full list of medications to have the full list sent to you now."

Another type of supplemental qualifying statement may be generated by a supplemental data operation that assesses the weight of evidence that supports primary data operation results. For instance, where only two prior patients with a specific cancer state responded positively to a YYY treatment, while a directly responsive query answer may indicate "There is evidence that at least some patients with the cancer state respond positively to YYY treatment", a supplemental response may be "Note however that only 2 patients responded positively to YYY treatment." In this case, the supplemental data operation would identify the number of positively responding patients, compare that to some statistically significant number associated with a higher level of confidence and, when the number is less than the statistically significant number, the operation would generate the supplemental response as a qualifying statement. As another instance, where a primary data operation response is "Chemotherapy is recommended for pancreatic cancer in the adjuvant setting", a qualifying supplemental phrase maybe "However, the role of radiation is still under review in clinical studies." This supplemental phrase would be generated based on results from a supplemental data operation associated with the query intent.

Other types of qualifying statements are contemplated.

Additional data of interest can be any data, subset of data, compilation of data or derivative of system data. For instance, where an oncologist asks for status of a specific patient symptom, the additional data may include statuses of additional typical symptoms given a specific patient's current cancer state.

Supplemental responses may include detailed information related to clinical trials identified in response to a primary data operation. For instance, here, a directly responsive phrase to a query may be "There are two clinical trials that may be of interest to Dwayne Holder." and a supplemental response may be "The first clinical trial is 23 miles from your office and the second trial is 35 miles from your office." Many other supplemental data operations regarding clinical trials are contemplated.

In at least some cases at least some databases will include specialized clinical reports or other report types that are developed for specific purposes where data is gleaned from EMRs and other system databases and used to instantiate specific instances of the reports for specific patients and cancer states. Here, in at least some cases an instantiated report will be generated and stored in persistent form (e.g., dated and unchanging) and in other cases an instantiated report will be stored but dynamic so that the system will routinely update the report as a patient's cancer state progresses over time. Where a report is stored in persistent form, multiple instances of the report may be stored persistently so that a historical record of the report can be developed over time. Where a report is stored dynamically, historical values for report fields may be stored so that time based instances of the report can be subsequently generated that reflect report information at any point during the course of a patient's treatment.

One advantage to using a fully formatted clinical report of a specific type (e.g., for pancreatic cancer, for breast cancer, for melanoma, etc.) is that an oncologist that routinely uses instantiated instances of specific report types quickly becomes familiar with types of information available in the reports as well as where in the reports the information resides. Once report familiarity matures, if specific information related to a specific patient's cancer state is sought, the oncologist will know if that information is located in the patient's clinical report and, once the report is accessed, where to locate the specific information.

Another advantage associated with a clinical report is that the report operates as a summary of EMR data and can include additional results of complex data operations on EMR data so that an oncologist does not have to recreate or process those operations manually. Thus, the report can include clinically important EMR data and also data and other information derived from the raw EMR data. The collaboration device 20 may provide information to the oncologist that is not available on the clinical report such as Tempus Insights, actionable mutations, etc.

Figure 17A:
Figure 17B:
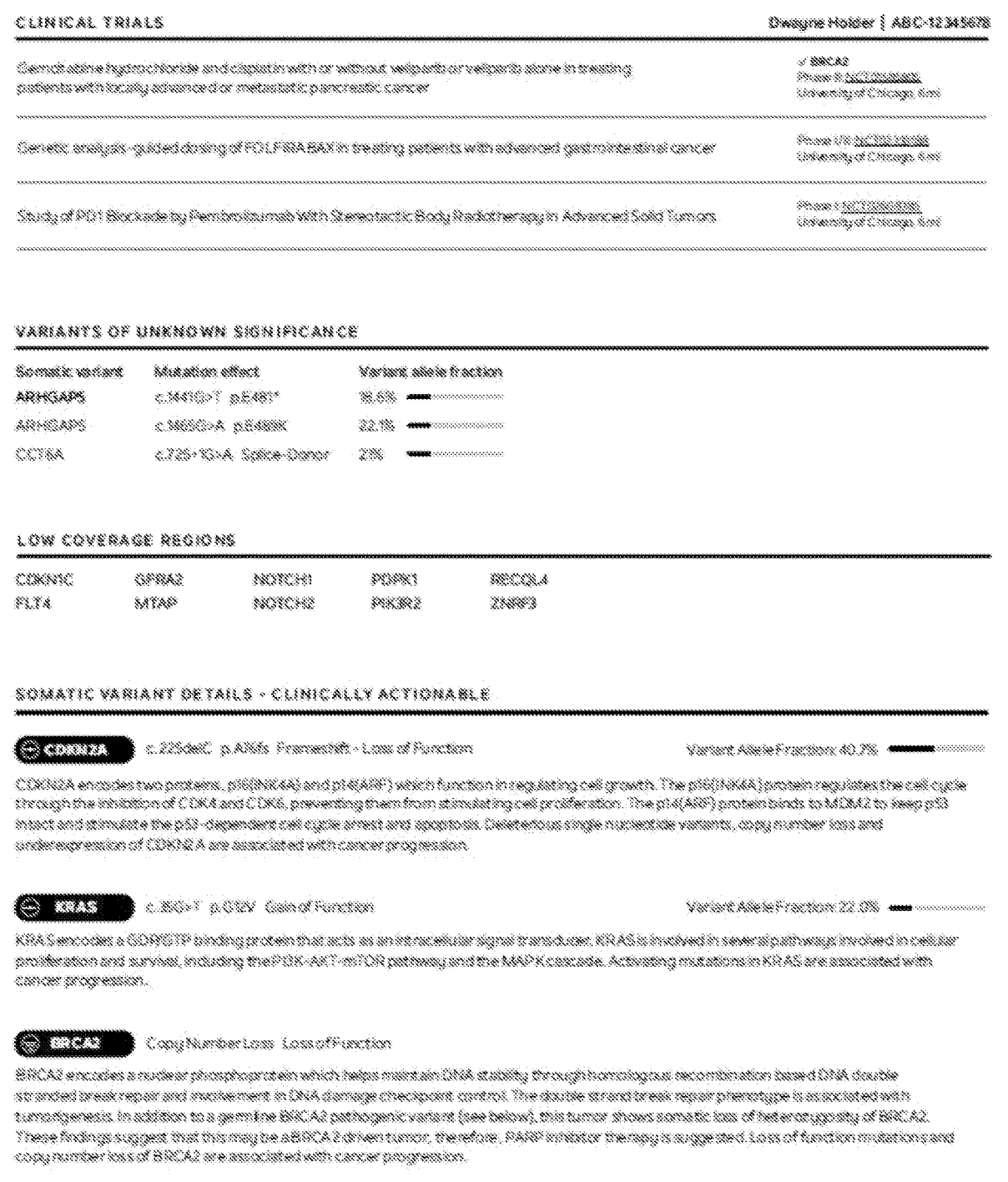

Referring now to FIGS. 17A through 17C, three pages of an exemplary clinical report related to patient Dwayne Holder who is afflicted with pancreatic cancer are shown. The report includes all important clinical information related to the patient's cancer state including report sections clearly marked as genomic variants, immunotherapy markers, FDA-approved therapies and current diagnosis, FDA approved therapies and other indications, current clinical trials, variants of unknown significance, low coverage regions, somatic variant details—clinically actionable, germline variant details, clinical history and oncologist notes (see lower left field in FIG. 17A). Here, the report format is simple and clearly defined so that an oncologist can locate specific information of interest rapidly.

From the perspective of the present disclosure, use of formatted clinical reports as primary data sources to drive a voice based collaboration system eases the tasks associated with developing a fulsome set of intents and supporting information for those records. In this regard, see again FIGS. 17A through 17C. While a large amount of clinically important patient information is presented on the report, the amount of information is limited so that an oncologist can rapidly become familiar with the report format and available data. Knowing a patient's general cancer state (e.g., pancreatic, breast, etc.) as well as report format and report data types for that state, an oncologist will naturally tend to limit system queries to ones calculated to be answerable via the report type information. Because the report data is limited (albeit including all clinically important data) to a specific set of medical record data for the patient, the number of intents required to support anticipated queries is appreciably limited. For instance, the number of intents required to fully support anticipated queries for the FIG. 17A-17C report may be on the order of several thousand as opposed to 100,000 or more for a complete EMR.

Another advantage associated with using formatted clinical reports as primary data sources to drive a voice based collaboration system is that the limited number of intents required to fully support anticipated queries makes it much easier for the collaborative system to uniquely distinguish an intended intent from all other supported intents. Thus, for instance, where only 5000 intents are required to fully handle all anticipated queries about information in a pancreatic clinical record, correct intent discernment is more likely than in a case where 100,000 intents need to be supported.

Yet one other advantage associated with using formatted clinical reports as primary data sources to drive a voice based collaboration system is that the system can leverage off complex data calculations that are already supported by an overall EMR system that generates the important information in the clinical reports. Thus, in the context of pancreatic cancer, the exemplary report in FIGS. 17A through 17C already includes all clinically important data including results of complex data operations so that the collaboration system does not have to independently derive required data and other information.

In some cases, near the beginning of a collaboration session, once the collaboration system identifies a specific patient, the system will identify the patient's cancer state and state-specific clinical medical record and automatically load up the subset of intents (e.g., "state related intents") that are associated with the patient's cancer state for consideration. In some cases, the state related intents may be the only intents that are considered by the system unless the oncologist instructs otherwise. In other cases the state related intents may be preferred (e.g., considered first or more heavily weighted options) than other more general EMR related intents so that if first and second intents in the state related intents and more general pool of intents are identified as possible intended intents, the system would automatically select the state related intent over the more general intent.

In at least some embodiments data operations associated with state related intents will be limited to an associated clinical record. Thus, for instance, referring again to FIGS. 17A through 17C, once Dwayne Holder is identified as a pancreatic cancer patient and a query intent has been identified, in these cases the data operations would be limited to the data and information presented in the FIG. 17A through 17C record.

In other cases data operations associated with state related intents may include any operations related to any EMR or other database data that is accessible by a system processor in addition to operations directly on the clinical report 17A-17C data and information.

In still other cases, cancer state-specific intents may be treated as preferred intents and other more general dataset intents may only be considered if the system cannot identify a state-specific intent to match with a received query. Here, in at least some cases even when a state-specific intent is identified, the system may generate a confidence factor associated with the intent and, if the confidence factor is below some threshold level, may consider other more general system intents as candidates to match with a specific query.

Figure 18:
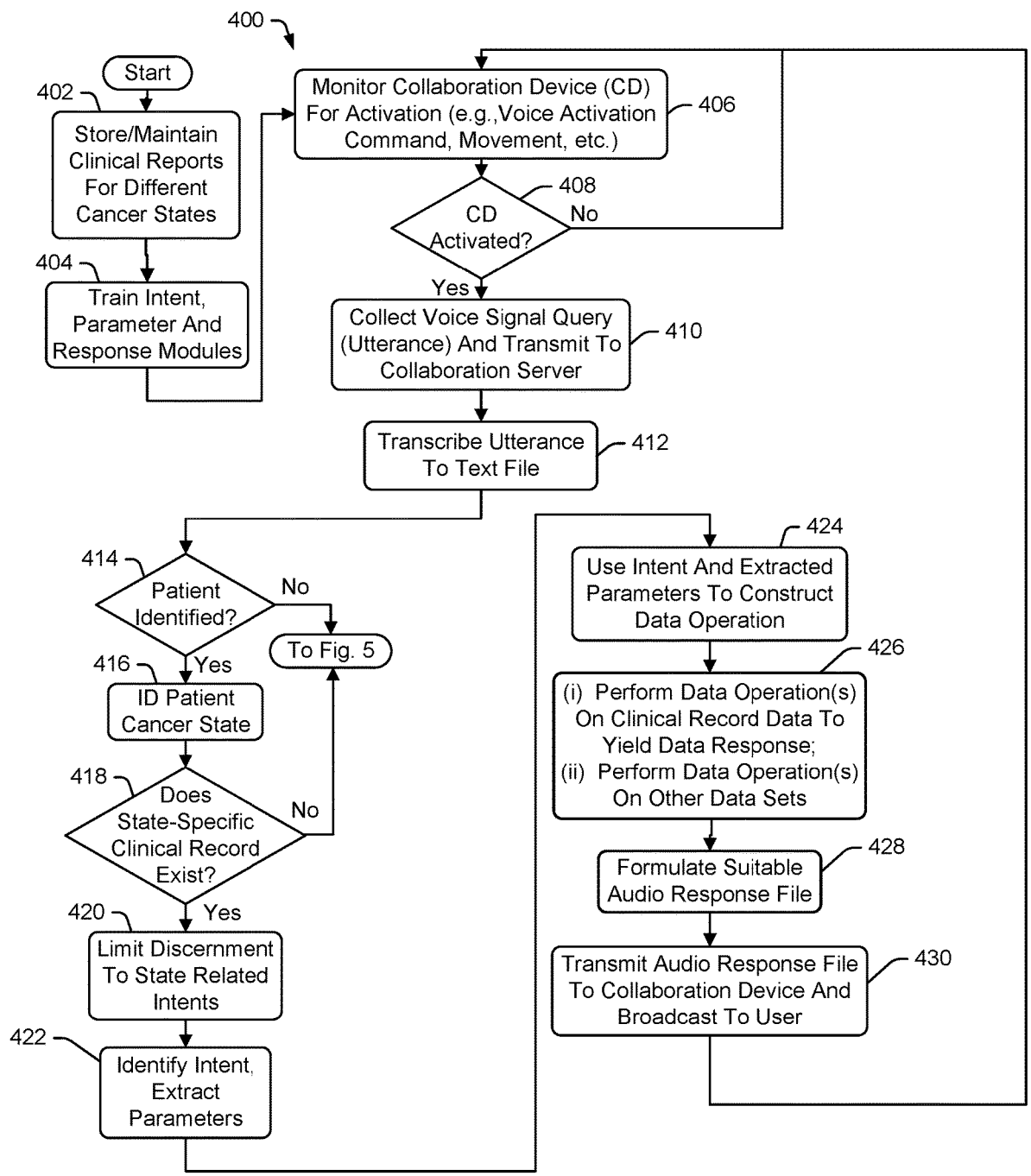
FIG. 18 is a flowchart similar to the chart shown in FIG. 5, albeit where a state-specific clinical record and related intents are used to drive a query process.

Referring now to FIG. 18, a process 400 similar to the process described above with respect to FIG. 5 is illustrated, albeit where the collaboration system automatically limits intents to a specific cancer state when a specific state clinical report is available for a specific patient. While process 400 is similar to the FIG. 5 process, several of the FIG. 5 process steps have been eliminated from process 400 in the interest of simplifying this explanation. For instance, FIG. 18 does not include steps to provide a visual response to an oncological query, among other things. Nevertheless, it should be appreciated that any of the additional steps shown in FIG. 5 could be added to the FIG. 18 process 400 in at least some embodiments of the present disclosure.

Referring to FIG. 18, at an initial process step 402 an EMR or other system stores and maintains clinical reports for specific patients and specific cancer states (e.g., pancreatic, breast, etc.). At block 404 an administrator uses an exemplary cancer state specific clinical report for each cancer state to train an essentially complete state specific set of intents and other supporting information (e.g., parameters, data operations and response files or phrases).

After system training, at block 406 the system monitors for activation of a collaboration device. At decision block 408, once a collaboration device is activated, the system monitors for voice signals and collects any voice signal query enunciated by an oncologist. At process block 412 any received utterances are transcribed to text and stored in a text file.

Referring still to FIG. 18, at decision block 414, a system processor monitors utterances for any information identifying a specific patient. If the oncologist does not identify a specific patient, system control may pass on to a process more akin to the process shown in FIG. 5 in an attempt to identify more general query intents based on a larger dataset. At block 414, if a patient is identified by an oncologist, control passes to process block 416 where the patient's cancer state is identified in a system database. At block 418, the system determines if there is a state-specific clinical record stored in a system database for the user. If there is no state-specific clinical record for the patient, again, control may pass on to the process shown in FIG. 5 in an attempt to identify more general query intents based on a larger dataset.

In FIG. 18, if a state-specific clinical record does exist for the patient, control passes to block 420 where the system limits the pool of intents to match with queries to the state related intents (e.g., intents specifically associated with the patient's state-specific clinical record type). Here, again, in some cases limitation will only mean that some weighting factor is applied to intents which makes it more likely the system will select a state-specific intent instead of a more general system intent. In other cases limitation means the system will only consider general intents until the oncologist performs some activity which causes the system to identify state-specific intents.

In particularly advantageous cases once a patient's general cancer state (e.g., pancreatic, breast, etc.) is determined, the system strictly limits (e.g., considers no other intents during a query path or a collaboration session) the intent pool to match with queries to the state specific clinical report set.

Continuing, at block 422, a processor compares a received query to the limited intent set to identify an intent and then extracts intent related parameters from the query. At process block 424 the system uses the intent and extracted parameters to define one or more data operations (e.g., primary or primary and supplemental per above discussion) to be performed on the clinical report data and, in at least some cases, on other accessible data sets. At block 426 the data operations are performed to generate information usable to respond to the query. At block 428 response files associated with the intent and data operations are used to formulate audio response files and at block 430 the audio response files are transmitted to the collaboration device and broadcast to the oncologist.

In at least some cases it is contemplated that the system will support an e-mail functionality whereby an oncologist can request e-mail copies of different clinical record datasets or other system datasets during a collaboration session. For instance, after the system broadcasts information related to clinical trials that may be off interest for a specific patient, an oncologist may enunciate "Send me information related to the trials." Here, the system would recognize the oncologist's intent to obtain e-mails including trial information for the trials in question, perform a data operation to access the trial information and then transmit that information to the oncologist's e-mail address. In addition, once the trial information is transmitted via e-mail, the system may generate and broadcast a response to the oncologist indicating that the trial information has been sent via e-mail. In other cases it is contemplated that data and information may be sent to an oncologist via other communication systems (e.g., as a text link, via regular mail hard copy, etc. A more complex e-mail related dialog path may include the following queries, where "Therapy Company" stands in for the name of one or more companies that provide therapies, and "Therapy" stands in for the name of one or more therapies:

Results of sequencing for Dwayne Holder.
Does my patient have high TMB?
Are they a good candidate for immunotherapy?
What immunotherapy drugs are currently approved?
Who manufactures Therapy?
What are the main adverse events to Therapy?
Email me the Therapy drug label.
Who manufactures Therapy.
What is the patient financial assistance phone number for Therapy Company?
E-mail me the Therapy Company compassionate use consent form.
E-mail me a Tempus insurance reimbursement letter that my patient Dwayne Holder has data justifying their off label use of Therapy.

In this example, the oncologist enunciates several e-mail requests where each would result in delivery of a different set of information to the oncologist's e-mail account.

In at least some cases when the system receives a query via a collaboration device, data operations will be executed on data from two or more different types of datasets. The first type may include a specific patient's genomic dataset that comprises details on the specific patient's molecular report. The second data type will include data that resides in general knowledge database (KDB) that includes non-patient specific information about specific topics (e.g., efficacy of specific drugs in treating specific cancer states, clinical trials information, drug class—mutation interactions, genes, etc.) based on accepted industry standards or empirical information derived by the service provider as well as information about the service provider's system capabilities (e.g., information about specific tests and activities performed by the provider, test requirements, etc.) To this end, see the exemplary system database 500 shown in FIG. 20 that includes molecular report genomic datasets and clinical data sets 502 and a non-patient specific knowledge database (KDB) 504. By arranging data operations in this fashion, the universe of possible intents and data operations that can be associated with any query is proscribed as described above and the advantages associated with such arrangements result.

Figure 20:
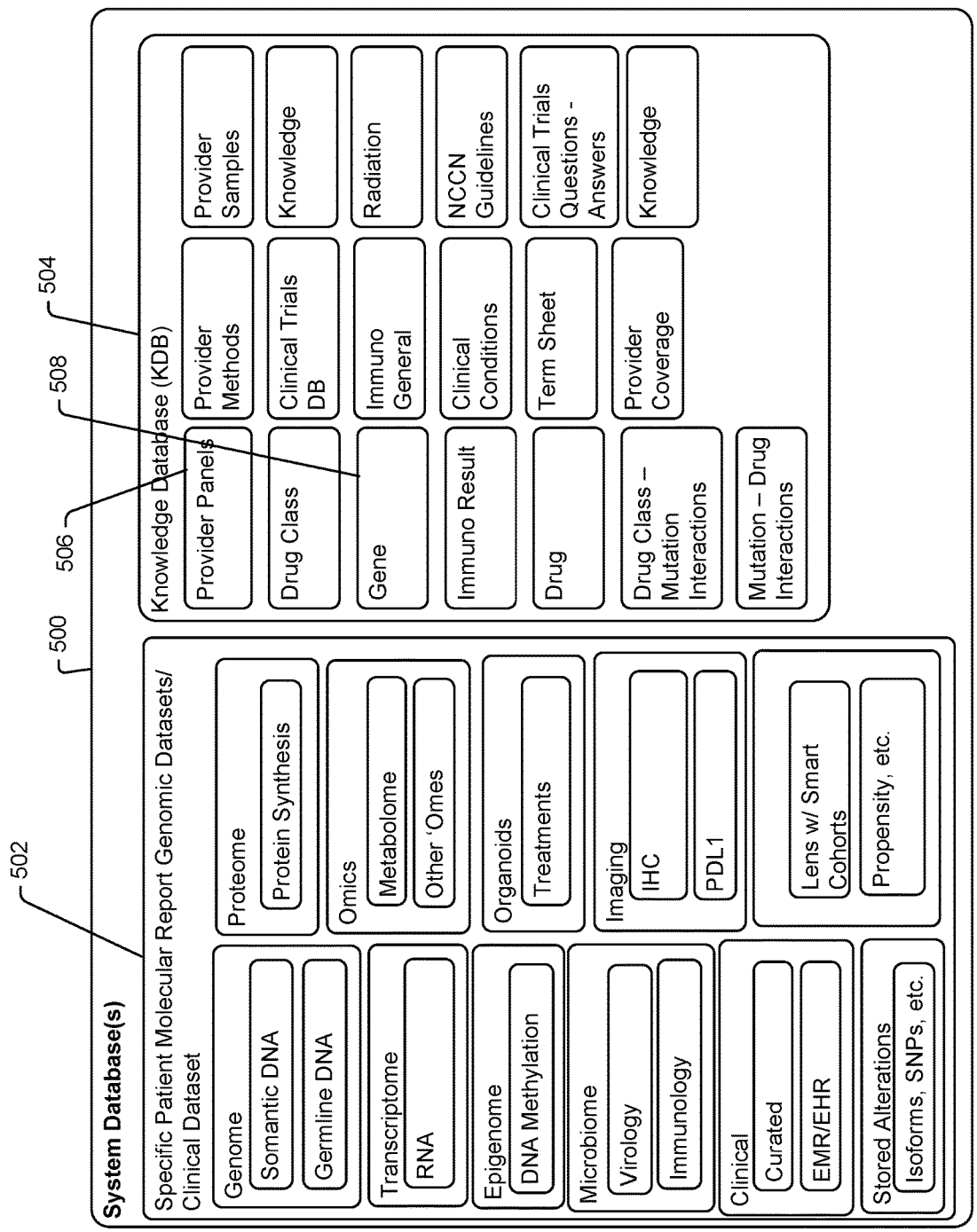
FIG. 20 is a system database that is consistent with at least some aspects of the present disclosure.

Referring still to FIG. 20, datasets 502 include, among other data, genome, transcriptome, epigenome, microbiome, clinical, stored alterations proteome, -omics, organoids, imaging and cohort and propensity data sets which are described in other patent applications in some detail. The KDB includes separate sub-databases related to specific information types including, as shown, provider panels 506 (e.g., information related to genetic panels supported by the service provider that operates the system), drug classes (e.g., drug class specific information (e.g., do drugs of a specific class work on pancreatic cancer, what drugs are considered to be included in a specific drug class, etc.)), specific genes 508, immuno results (e.g., information related to treatments based on specific immuno biomarker results), specific drugs, drug class-mutation interactions, mutation-drug interactions, provider methods (e.g., questions about processes performed by the service provider), clinical trials, immuno general, clinical conditions such as clinical diseases, term sheets (e.g., definitions of industry specific terms), provider coverage (e.g., information about provider tests and results), provider samples (e.g., information about types of samples that can be processed by the provider), knowledge (e.g., scripted questions and answers on various frequently asked questions that do not fall into other sub-databases), radiation (e.g., information related to suitable radiation treatments given specific cancer states), NCCN guidelines (e.g., national guidelines related to classification of cancer states, accepted treatments, etc.) and clinical trials questions—answers (e.g., information related to locations and administrators of clinical trials. Organizing the KDB into sub-databases makes it easier to manage those databases as information therein evolves over time and also enables addition of new sub-databases related to other defined information types.

To identify a genomic dataset associate with a specific patient's molecular report, the system identifies data operations associated with a query and then associates at least one of those operations with the patient's genomic dataset represented on the molecular report prior to executing the at least one data operation on the set.

In at least some cases results of a data operation on a patient's molecular report data inform other data operations to perform on the KDB or results from operations on a KDB inform other operations to perform on a patient's molecular report data. For instance, in a case where an oncologist queries "What are the treatment implications of Dwayne Holder's CDKN2A mutation?", the system may associate the query with an intent. The intent may be associated with two data operations including a first to search a general KDB for appropriate treatments for a CDKN2A mutation and a second operation to determine if the patient has already been treated with one or more of the appropriate treatments. In this case, results from a KDB data operation inform the molecular report data operation. As another instance, in a case where an oncologist queries "Did Dwayne Holder have loss of heterozygosity with his BRCA2 mutation?", the system may again identify two data operations, this time including a first operation on the genomic dataset associated with Dwayne Holder's molecular report to return the patient's loss of heterozygosity (LOH) value and a second operation to perform on a KDB to determine if the patient's mutation and LOH value pairing is known to be a tumor driver. In this case, results from the operation on the molecular report data inform the KDB data operation.

Hereafter first and second exemplary processes related to handling of the queries "What are the treatment implications of Dwayne Holder's CDKN2A mutation?" and "Did Dwayne Holder have loss of heterozygosity with his BRCA2 mutation?", respectively, are described. In the interest of simplifying this explanation, the first and second processes will be referred to as first and second examples, respectively, unless indicated otherwise.

Figure 19:
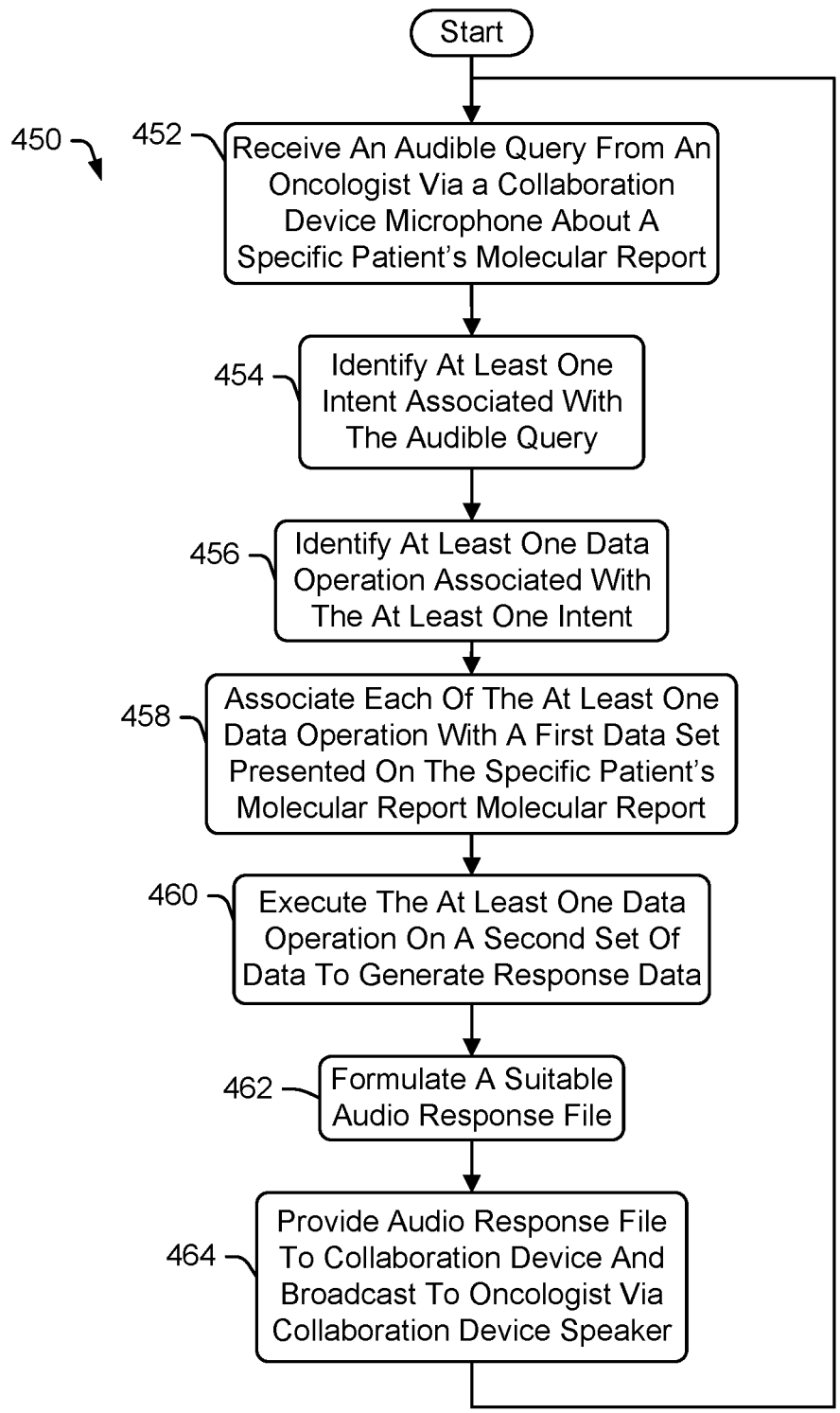
FIG. 19 is an audio response process that is consistent with at least some aspects of the present disclosure.

Referring now to FIG. 19, a process 450 that is consistent with at least some aspects of the present disclosure is shown that associates data operations with a genomic dataset represented on a patient's molecular report prior to performing those operations on the dataset. At process block 452, a collaboration device 20 (see again FIG. 1) receives an audible query from an oncologist via the device microphone that is related to information that appears on the specific patient's molecular report, which can be stored in a system database. In some embodiments, the process 450 can store the specific patient's molecular report and/or other patient's molecular reports in the system database. In this way, the process 450 can store molecular reports for multiple patients. In some embodiments, the process 450 may identify the specific patient as described in conjunction with FIG. 18. In at least some cases, the audible query can include a question about a nucleotide profile associated with the patient. The nucleotide profile associated with the patient can be a profile of the patient's cancer. The nucleotide profile associated with the patient can be a profile of the patient's germline. The nucleotide profile associated with the patient can be a DNA profile. The nucleotide profile associated with the patient can be an RNA expression profile. The nucleotide profile associated with the patient can be a mutation biomarker. The nucleotide profile associated with the patient can be a BRCA biomarker. In at least some cases, the audible query can include a question about a therapy. In at least some cases, the audible query can include a question about a gene. In at least some cases, the audible query can include a question about a clinical data. The clinical data may include at least one of the clinical data elements described above. In at least some cases, the audible query can include a question about a next-generation sequencing panel. In at least some cases, the audible query can include a question about a biomarker. In at least some cases, the audible query can include a question about an immune biomarker. In at least some cases, the audible query can include a question about an antibody-based test. In at least some cases, the antibody-based test can be a a blood sample based antibody test. In at least some cases, the audible query can include a question about a clinical trial. In at least some cases, the audible query can include a question about an organoid assay. In at least some cases, the audible query can include a question about a pathology image. The pathology image can be a slide image, for example, an image generated using whole-slide imaging (WSI). In at least some cases, the audible query can include a question about a disease type.

In some embodiments, at block 452, the process 450 can identify at least one qualifying parameter in the audible query. In some cases, the at least one qualifying parameter can include a patient identity, a patient's disease state, a genetic mutation, and/or a procedure type. In some embodiments, the process 450 can identify qualifying parameters in the first patient's molecular report.

At block 454 the system identifies at least one intent associated with the audible query. Here, block 454 entails identifying a general intent as well as context parameters within the query so that a specific intent can be formulated. For instance, in the case of the first example query "What are the treatment implications of Dwayne Holder's CDKN2A mutation?", a general intent identified may be "What are treatment implications based on gene mutation for patient?" and specific query parameters may include "CDKN2A and "Dwayne Holder" where the underlined gene and patient fields in the general query are populated with "CDKN2A" and "Dwayne Holder" to generate a specific query intent.

In the case of the second example query "Did Dwayne Holder have loss of heterozygosity with his BRCA2 mutation?", a general intent identified may be "Did patient experience genetic characteristic with gene mutation?" where the underlined patient, genetic mutation and gene fields in the general query are populated with "Dwayne Holder", "heterozygosity" and "BRCA2", respectively, to generate a specific query intent.

In at least some cases, the at least one intent can be associated with an audible query. In at least some cases, the at least one intent can be an intent related to a clinical trial. In at least some cases, the at least one intent can be related to a drug. In at least some cases, the intent can be referred to as a drug intent if the intent is related to a drug. In at least some cases, the drug intent can be related to a drug such as chemotherapy. In at least some cases, the drug intent can be an intent related to a PARP inhibitor intent. In at least some cases, the at least one intent can be related to a gene. In at least some cases, the at least one intent can be related to immunology. In at least some cases, the at least one intent can be related to a knowledge database. In at least some cases, the at least one intent can be related to testing methods. In at least some cases, the at least one intent can be related to a gene panel. In at least some cases, the at least one intent can be related to a report. In at least some cases, the at least one intent can be related to an organoid process. In at least some cases, the at least one intent can be related to imaging. In at least some cases, the at least one intent can be related to a pathogen. In some aspects, the pathogen may be a pathogenic mutation. In at least some cases, the at least one intent can be related to a vaccine.

The at least one intent can be related to at least one activity. The at least one activity can include periodically capturing health information from electronic health records included in the knowledge database. The at least one activity can include checking the status of an existing clinical or lab order. The at least one activity can include ordering a new clinical or lab order. The at least one activity can include automatically initiating the at least one activity without any initiating input from the oncologist. The at least one activity can include uploading the patient's EHR to the knowledge database.

Referring still to FIG. 19, once a specific intent is identified, at block 456 the system identifies at least one data operation associated with the specific intent. Here, a database correlates data operations with intents. For instance, in some cases one or more data operations may be correlated with each specific intent. In other cases at least some data operations may depend on results from other data operations (e.g., a second operation is only performed if results from a first operation are within a specific value range).

In some embodiments, at block 456, the process 450 can identify the at least one data operation based on both the identified intent and the at least one qualifying parameter.

In the case of the first example, for the specific intent "What are treatment implications based on CDKN2A mutation for Dwayne Holder?", exemplary data operations may include (1) For CDKN2A mutation, search for appropriate treatments in a treatments KDB and (2) For appropriate treatments, search a treatment history portion of a patient's molecular report genomic dataset to identify if patient already treated with appropriate treatments. Similarly, in the case of the second example, for the specific intent "Did Dwayne Holder experience loss of heterozygosity with BRCA2 mutation?", exemplary data operations may include (1) search for LOH value in patient's molecular report genomic dataset as well as whether the mutation is germline or somatic and (2) based on the LOH value, optionally search a KDB (e.g., the KDB 504) to determine whether the LOH value and mutation are known to be a tumor driver.

In at least some cases, the at least one data operation can include an operation to identify at least one treatment option. In at least some cases, the at least one data operation can include an operation to identify knowledge about a therapy. In at least some cases, the at least one data operation can include an operation to identify knowledge related to at least one drug. For example, the knowledge can be what drugs, if any are associated with high CD40 expression. In at least some cases, the at least one data operation can include an operation to identify knowledge related to mutation testing. For example, the knowledge can be whether Dwayne Holder's sample tested for a KMT2D mutation. In at least some cases, the at least one data operation can include an operation to identify knowledge related to mutation presence. For example, the knowledge can be whether Dwayne Holder has a KMT2C mutation. In at least some cases, the at least one data operation can include an operation to identify knowledge related to tumor characterization. For example, the knowledge can be if Dwayne Holder's tumor be a BRCA2 driven tumor. In at least some cases, the at least one data operation can include an operation to identify knowledge related to testing requirements. For example, the knowledge can be what tumor percentage Tempus requires for TMB results. In at least some cases, the at least one data operation can include an operation to query for definition information. For example, the definition information can be the definition of PDL1 expression. In at least some cases, the at least one data operation can include an operation to query for expert information. For example, the expert information can include the clinical relevance of PDL1 expression or what common risks are associated with the Whipple procedure. In at least some cases, the at least one data operation can include an operation to identify information related to recommended therapy. For example, the information can be whether or not Dwayne Holder is a candidate for immunotherapy given that he is in the 88th percentile of PDL1 expression. In at least some cases, the at least one data operation can include an operation to query for information relating to a patient. In at least some cases, the at least one data operation can include an operation to query for information relating to patients with one or more clinical characteristics similar to the patient. For example, the information can be what the most common adverse events are for patients similar to Dwayne Holder. In at least some cases, the at least one data operation can include an operation to query for information relating to patient cohorts. For example, the information can be what the most common adverse events are for pancreatic cancer patients. In at least some cases, the at least one data operation can include an operation to query for information relating to clinical trials. For example, the information can be which clinical trials Dwayne Holder is the best match for. In at least some cases, the at least one data operation can include an operation to query about a characteristic relating to a genomic mutation. In at least some cases, the characteristic can be loss of heterozygosity. In at least some cases, the characteristic can reflect the source of the mutation. In at least some cases, the source can be germline. In at least some cases, the source can be somatic. In at least some cases, the characteristic can include whether the mutation is a tumor driver.

Referring again to FIG. 19, at block 458 the system associates each of the at least one data operations with a first dataset (i.e., a first set of data) presented on a specific patient's molecular report. In the case of the first example, the system associates each of the data operations with CDKN2A which, as seen in FIG. 17A, is presented on the molecular report. In the case of the second example, the system associates the first data operation with BRCA2 and Dwayne Holder in the molecular report genomic dataset. In some embodiments, the system can access the specific patient's molecular report at block 458.

In at least some cases, the first set of data can also be a gene editing therapy that has been previously researched and/or documented by a reputable source. In at least some cases, the gene editing therapy can be a clustered regularly interspaced short palindromic repeats (CRISPR) therapy. In at least some cases, the first set of data can include a patient name. In at least some cases, the first set of data can include a patient age. In at least some cases, the first set of data can include a next-generation sequencing panel. In at least some cases, the first set of data can include a genomic variant. In at least some cases, the first set of data can include a somatic genomic variant. In at least some cases, the first set of data can include a germline genomic variant. In at least some cases, the first set of data can include a clinically actionable genomic variant. In at least some cases, the first set of data can include a loss of function variant. In at least some cases, the first set of data can include a gain of function variant. In at least some cases, the first set of data can include an immunology marker. In at least some cases, the first set of data can include a tumor mutational burden. In at least some cases, the first set of data can include a microsatellite instability status. In at least some cases, the first set of data can include a diagnosis. In at least some cases, the first set of data can include a therapy. In at least some cases, the first set of data can include a therapy approved by the U.S. Food and Drug Administration. In at least some cases, the first set of data can include a drug therapy. In at least some cases, the first set of data can include a radiation therapy. In at least some cases, the first set of data can include a chemotherapy. In at least some cases, the first set of data can include a cancer vaccine therapy. In at least some cases, the first set of data can include an oncolytic virus therapy. In at least some cases, the first set of data can include an immunotherapy. In at least some cases, the first set of data can include a pembrolizumab therapy. In at least some cases, the first set of data can include a CAR-T therapy. In at least some cases, the first set of data can include a proton therapy. In at least some cases, the first set of data can include an ultrasound therapy. In at least some cases, the first set of data can include a surgery. In at least some cases, the first set of data can include a hormone therapy. In at least some cases, the first set of data can include an off-label therapy. In some aspects, the off-label therapy can include a drug therapy. In at least some cases, the first set of data can include an on-label therapy. In at least some cases, the first set of data can include a bone marrow transplant event. In at least some cases, the first set of data can include a cryoablation event. In at least some cases, the first set of data can include a radiofrequency ablation. In at least some cases, the first set of data can include a monoclonal antibody therapy. In at least some cases, the first set of data can include an angiogenesis inhibitor. In at least some cases, the first set of data can include a PARP inhibitor. In at least some cases, the first set of data can include a targeted therapy. In some aspects, the targeted therapy may be a molecularly targeted therapy. In at least some cases, the first set of data can include an indication of use. In some aspects, the indication of use may be an indication of use for a drug in treating a condition, such as a disease. In at least some cases, the first set of data can include a clinical trial. In at least some cases, the first set of data can include a distance to a location conducting a clinical trial. In at least some cases, the first set of data can include a variant of unknown significance. In some aspects, variants may be classified as pathogenic, likely pathogenic, variant of unknown significance, likely benign, or benign variants. In at least some cases, the first set of data can include a mutation effect. In some aspects, the mutation effect may be positive (e.g., associated with a reduction in risk of heart disease), negative (e.g., associated with an increase in risk of heart disease), or neutral (e.g., associated with no significant change in risk of heart disease). In at least some cases, the first set of data can include a variant allele fraction. In some aspects, the variant allele fraction may be the proportion of variant reads for a given mutation. In at least some cases, the first set of data can include a low coverage region. In at least some cases, the first set of data can include a clinical history. In at least some cases, the first set of data can include a biopsy result. In some aspects, the biopsy result may include a grade of how aggressive a cancer is. For example, the grade may range from one to four, with one indicating a least aggressive cancer, and four indicating a most aggressive cancer. In at least some cases, the first set of data can include an imaging result. In at least some cases, the first set of data can include an MRI result. In at least some cases, the first set of data can include a CT result. In at least some cases, the first set of data can include a therapy prescription. In at least some cases, the first set of data can include a therapy administration. In at least some cases, the first set of data can include a cancer subtype diagnosis. In at least some cases, the first set of data can include a cancer subtype diagnosis by RNA class. In at least some cases, the first set of data can include a result of a therapy applied to an organoid grown from the patient's cells. In at least some cases, the first set of data can include a tumor quality measure. In at least some cases, the first set of data can include a tumor quality measure selected from at least one of the set of PD-L1, MMR, tumor infiltrating lymphocyte count, and tumor ploidy. In at least some cases, the first set of data can include a tumor quality measure derived from an image analysis of a pathology slide of the patient's tumor. In at least some cases, the first set of data can include a signaling pathway associated with a tumor of the patient. In at least some cases, the signaling pathway can be a HER pathway. In at least some cases, the signaling pathway can be a MAPK pathway. In at least some cases, the signaling pathway can be a MDM2-TP53 pathway. In at least some cases, the signaling pathway can be a PI3K pathway. In at least some cases, the signaling pathway can be a mTOR pathway.

In at least some cases, the at least one data operations can include an operation to query for a treatment option, the first set of data can include a genomic variant, and the associating step (i.e., block 458) can include adjusting the operation to query for the treatment option based on the genomic variant. In at least some cases, the at least one data operations can include an operation to query for a clinical history data, the first set of data can include a therapy, and the associating step (i.e., block 458) can include adjusting the operation to query for the clinical history data element based on the therapy. In at least some cases, the clinical history data can be medication prescriptions, the therapy can be pembrolizumab, and the associating step can include adjusting the operation to query for the prescription of pembrolizumab.

Continuing, at block 460 the system executes each of the data operations on a second set of data to generate response data. In the case of the first example, the first data operation on a KDB (e.g., a second data set) yields Palbociclib as an appropriate treatment for the patient's CDKN2A mutation and the second data operation on the molecular report genomic dataset (e.g., another second dataset) indicates that Dwayne Holder has already been treated with Palbociclib. In the case of the second example, response data from the first data operation on Dwayne Holder's molecular report genomic dataset (e.g., a second dataset) indicates no pathogenic somatic BRCA2 mutation but also indicates that there is a pathogenic germline BRCA2 mutation and an LOH loss associated therewith (see BRCA2 section of the molecular report shown at bottom of FIG. 17B that indicates LOH). In the second example, the first data operation results (e.g., germline BRCA2 mutation and presence of somatic LOH) are used to drive the second data operation and the response data indicates that the tumor is a BRCA2 driven tumor.

In at least some cases, the second set of data can include clinical health information. In at least some cases, the second set of data can include genomic variant information.

In at least some cases, the second set of data can include DNA sequencing information. In at least some cases, the second set of data can include RNA information. In at least some cases, the second set of data can include DNA sequencing information from short-read sequencing. In at least some cases, the second set of data can include DNA sequencing information from long-read sequencing. In at least some cases, the second set of data can include RNA transcriptome information. In at least some cases, the second set of data can include RNA full-transcriptome information. In at least some cases, the second set of data can be stored in a single data repository. In at least some cases, the second set of data can be stored in a plurality of data repositories. In at least some cases, the second set of data can include clinical health information and genomic variant information. In at least some cases, the second set of data can include immunology marker information. In at least some cases, the second set of data can include microsatellite instability immunology marker information. In at least some cases, the second set of data can include tumor mutational burden immunology marker information. In at least some cases, the second set of data can include clinical health information including one or more of demographic information, diagnostic information, assessment results, laboratory results, prescribed or administered therapies, and outcomes information. In at least some cases, the second set of data can include demographic information comprising one or more of patient age, patient date of birth, gender, race, ethnicity, institution of care, comorbidities, and smoking history. In at least some cases, the second set of data can include diagnosis information including one or more of tissue of origin, date of initial diagnosis, histology, histology grade, metastatic diagnosis, date of metastatic diagnosis, site or sites of metastasis, and staging information. In at least some cases, the second set of data can include staging information including one or more of TNM, ISS, DSS, FAB, RAI, and Binet. In some aspects, the staging information may be referred to as "cancer staging information." In at least some cases, the second set of data can include assessment information including one or more of performance status including at least one pf ECOG status or Karnofsky status, performance status score, and date of performance status. In at least some cases, the second set of data can include laboratory information including one or more of type of lab (e.g. CBS, CMP, PSA, CEA), lab results, lab units, date of lab service, date of molecular pathology test, assay type, assay result (e.g. positive, negative, equivocal, mutated, wild type), molecular pathology method (e.g. IHC, FISH, NGS), and molecular pathology provider. In at least some cases, the second set of data can include treatment information including one or more of drug name, drug start date, drug end date, drug dosage, drug units, drug number of cycles, surgical procedure type, date of surgical procedure, radiation site, radiation modality, radiation start date, radiation end date, radiation total dose delivered, and radiation total fractions delivered. In at least some cases, the second set of data can include outcomes information including one or more of Response to Therapy (e.g. CR, PR, SD, PD), RECIST score, Date of Outcome, date of observation, date of progression, date of recurrence, adverse event to therapy, adverse event date of presentation, adverse event grade, date of death, date of last follow-up, and disease status at last follow up. In at least some cases, the second set of data can include information that has been de-identified in accordance with a de-identification method permitted by HIPAA. In at least some cases, the second set of data can include information that has been de-identified in accordance with a safe harbor de-identification method permitted by HIPAA. In at least some cases, the second set of data can include information that has been de-identified in accordance with a statistical de-identification method permitted by HIPAA. In at least some cases, the second set of data can include clinical health information of patients diagnosed with a cancer condition. In at least some cases, the second set of data can include clinical health information of patients diagnosed with a cardiovascular condition. In at least some cases, the second set of data can include clinical health information of patients diagnosed with a diabetes condition. In at least some cases, the second set of data can include clinical health information of patients diagnosed with an autoimmune condition. In at least some cases, the second set of data can include clinical health information of patients diagnosed with a lupus condition. In at least some cases, the second set of data can include clinical health information of patients diagnosed with a psoriasis condition. In at least some cases, the second set of data can include clinical health information of patients diagnosed with a depression condition. In at least some cases, the second set of data can include clinical health information of patients diagnosed with a rare disease.

Referring yet again to FIG. 19, at block 462 the system formulates a suitable audio response file and at block 464 the response file is used to broadcast an audible response to the oncologist. In the first example, the system may generate the following response "Provider recommends Palbociclib, a CDK4/6 inhibitor based on Dwayne Holder's CDKN2A mutation. He has already received this drug from Sep. 20, 2017 to Jan. 6, 2018 however, so you may want to consider targeting one of his other clinically actionable mutations." In the second example, the system may generate the following response "Dwayne Holder's results showed a pathogenic germline BRCA2 mutation combined with a somatic loss of heterozygosity, indicating that this may be a BRCA2 driven tumor."

It has been recognized that many different query intents may take similar formats where the differences between specific intents are defined by specific parameters. Similarly, many system responses to different queries may have similar formats where differences between the specific responses are defined by specific parameters in the queries and/or results generated by data operations. For these reasons, in at least some embodiments, a specialized user interface has been developed to reduce the burden on a system administrator associated with specifying all possible system intents, contextual query parameters, data operations and audio response files as well as to manage that information as knowledge evolves over time. The interface generates sub-databases (see sub-databases in FIG. 20) that form the KDB shown in FIG. 20.

Figure 21:
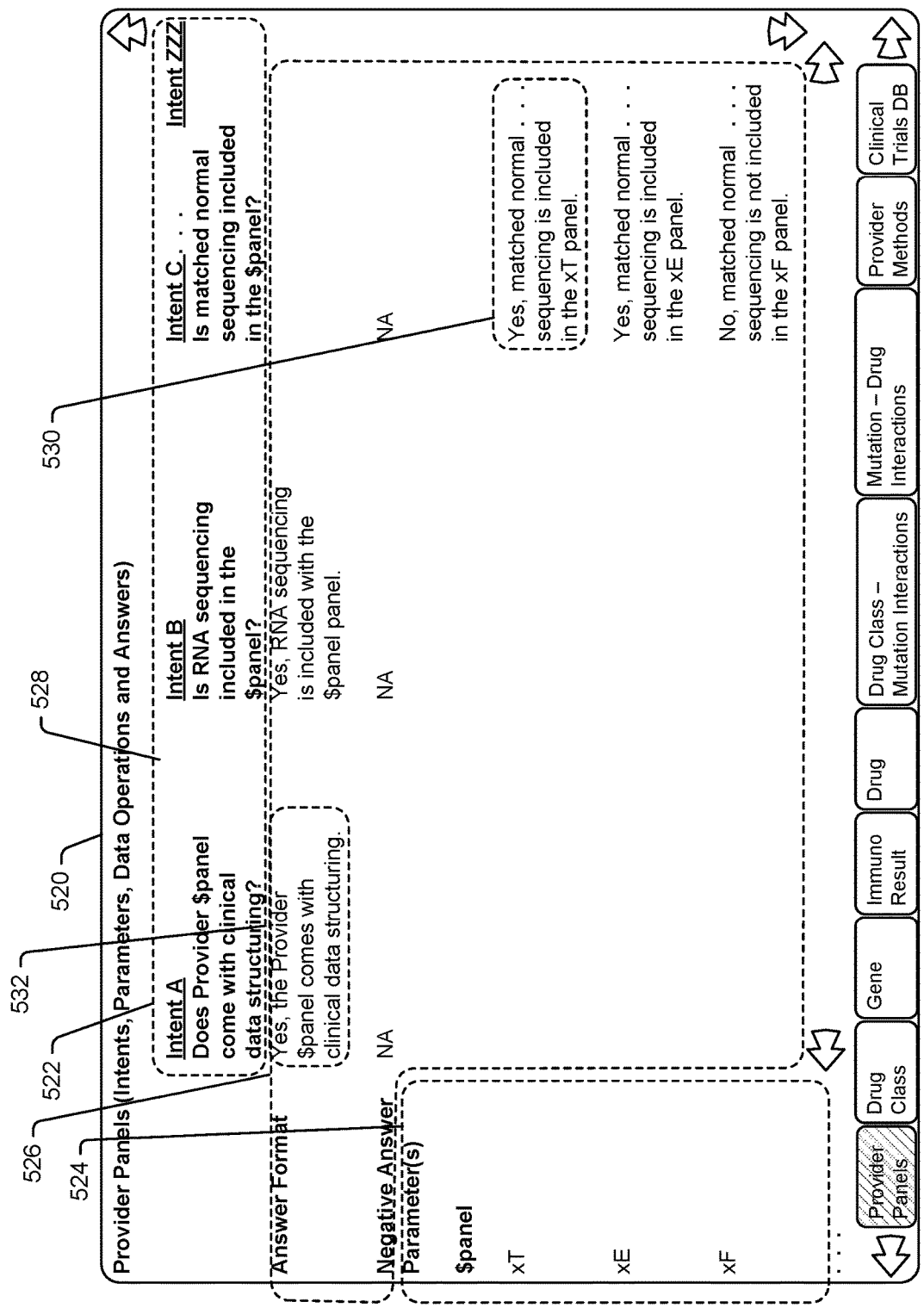
FIG. 21 is a screen shot for use by a system administrator for specifying system intents, intent parameters and answer formats for provider panel types that is consistent with at least some aspects of the present disclosure.

See FIG. 21 that schematically illustrates an exemplary user interface screen shot 520 that corresponds to the provider panels sub-database 506 shown in FIG. 20. In addition to presenting a provider panels dataset, the screen shot includes a separate selectable icon for each of the sub-database types in FIG. 20 so that an administrator can access any one of those sub-databases via a screen shot akin to the one shown in FIG. 21. Screen shot 520 includes a spreadsheet type arrangement of information cells in rows and columns used by the system to processes queries and generate responses as well as interface tools for scrolling up and down and left and right to access additional sub-database information. Although not shown an exemplary interface would also include a keyboard, mouse device and/or other input devices for interacting with the interface (e.g., scrolling, modifying information, adding or deleting information, etc.)

Referring still to FIG. 21, the screen shot 520 includes query intents 522 A through ZZZ arranged in a first row of cells, a separate intent in a cell at the top of each column within a first row. Intents often take the form of a defined query that received queries can be associated with. Exemplary intent A shown is "Does Provider $panel come with clinical data structuring?" where the "$panel" representation is a parameter that is gleaned from a query received from an oncologist. Although only a small number of intents are shown, it should be appreciated that hundreds or more intents may be expressed and accessed via the interface. The $panel representation is referred to as a parameter field and the system supports many parameter types with different parameter fields and any intent may include two or more different parameter fields.

Referring still to FIG. 21, parameters that may fill in the $panel parameter fields in the intents are listed in cells arranged in a left hand column 524 on screen shot 520 and include xT, xE and xF and may include many other panel types. Thus, depending on a received query (e.g., does the query reference an xT panel?), the $panel field in intent A may be filled in with any of xT, xE, xF, etc., to define a panel specific intent.

Answers are provided for each intent and parameter combination in an answer section 526 of the screen shot. In general the answer section includes separate cells for each of the parameter rows and intent columns and separate scripted answers may be provided in each of the answer cells for each of the intent-parameter combinations. For instance, for intent C and an xT panel, the answer in an associated answer cell 530 is "Yes, matched normal sequencing is included in the xT panel."

In cases where a general answer format is applicable to each parameter in column 524, an answer format may be provided where specific parameters are used to fill in parameter fields in the answer format. To this end, see the answer format in field 532 that requires a panel parameter in field $panel. Here, in operation, the system retrieves a suitable panel parameter from column 524 and fills in field $panel when appropriate. Although not shown in FIG. 21, a negative answer row 536 is also provided that may include negative answer formats for one or each of the intents listed in row 522.

Referring still to FIG. 21, an administrator can change any intent, add intents, delete intents, change a parameter in column 524, add a parameter, delete a parameter and/or change an answer by simply selecting an instance of the information to change and then typing different information into the associated cell. In this way, intents and answers with formats that are similar for different parameters can be quickly specified and managed with less overall effort. For instance, in FIG. 21 assume the interface specifies 200 different intents and an administrator wants to add a new panel to the parameter options. Here, the administrator can just select another cell in the parameter column and name the new panel causing all the intents in row 522 to be associated with the new panel name. In addition, when the new panel is added to the panel column, for each answer format (e.g., see again 532) that remains valid for the new panel, that answer formats are automatically applied to the new panel.

Figure 22:
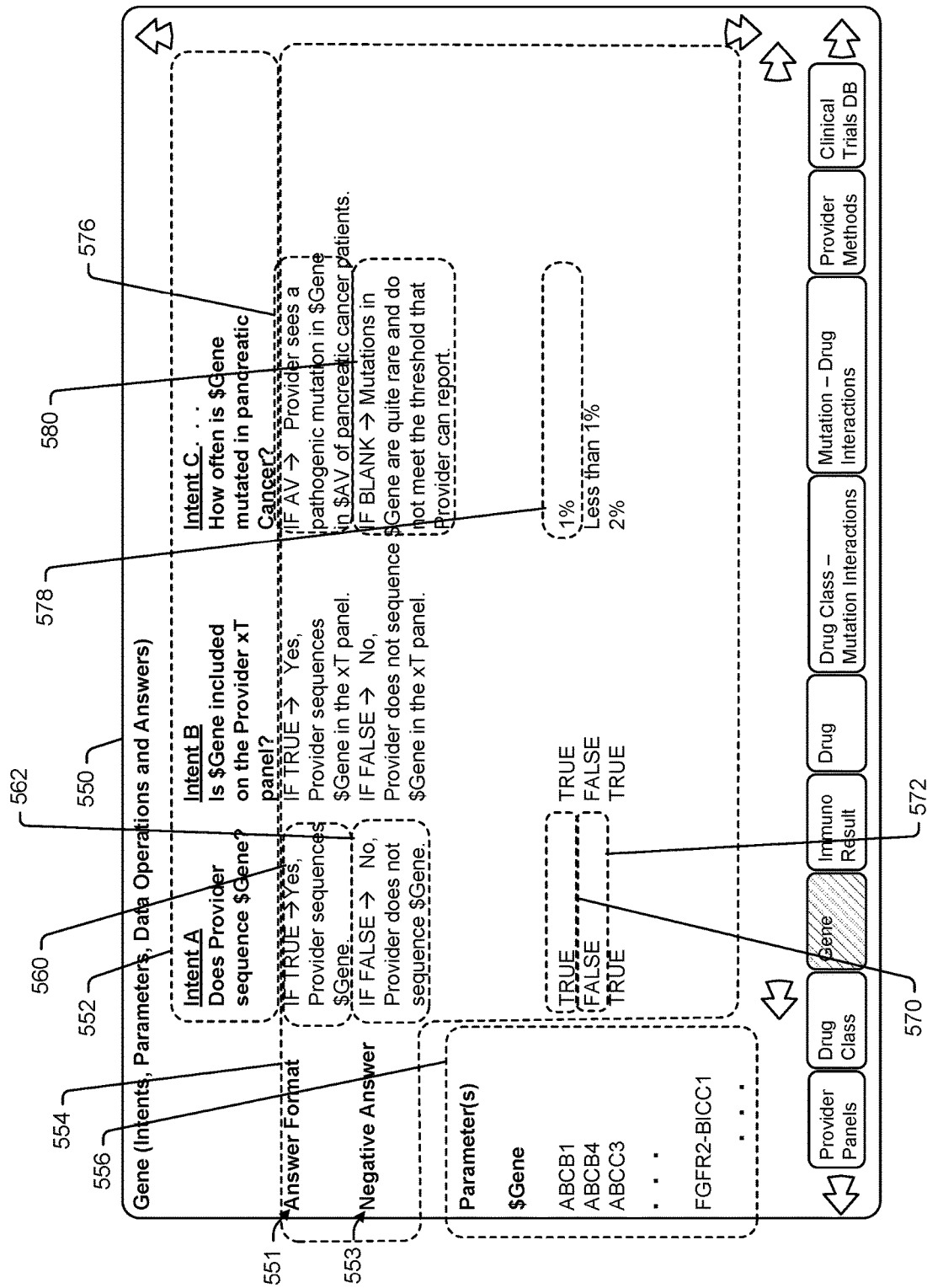
FIG. 22 is similar to FIG. 21, albeit including a screen shot for specifying gene specific system information.

Referring now to FIG. 22, a second administrator interface screen shot 550 is illustrated that has a format similar to the FIG. 21 provider panels screen shot and, to that end, includes an intents row 552, an answer section 554 and a parameters section 556. Each exemplary intent includes a parameter field $Gene which is filled in with one of the parameters from the parameter column 556 that forms part of a received query.

In FIG. 22 the answer section 554 is different than in FIG. 21 as "answer values" are provided in each answer cell (e.g., a cell corresponding to a specific intent column and parameter row combination) that are used in at least one and in some cases two different ways. First, answers in the answer cells corresponding to specific intent and parameter pairings can be used to select one of the answer format 551 or negative answer format 553. To this end, each of the answer format and the negative answer format for each format includes each of a rule and a response format where the rules apply based on answer cell values. Thus, for instance, for the answer format in cell 560, the rule is "IF TRUE" (e.g., if a TRUE value is in an answer cell), then apply the associated answer format. Similarly, for the negative answer format in cell 562, the rule is "IF FALSE" (e.g., if a FALSE value is in an answer cell), then apply the associated negative answer format. Thus, for instance, because the answer cell 570 includes the value TRUE for gene ABCB1 and intent A, the answer format in cell 560 is applied and the response file includes the phrase "Yes, Provider sequences ABCB1." Similarly, because the answer cell 572 includes the value false for gene ABCB4 and intent A, the negative answer format in cell 562 is applied and the response file includes the phrase "No, Provider does not sequence ABCB4."

Second, in at least some cases answer cell values can also be used to populate one or more fields in an answer format or a negative answer format. To this end, see for instance the answer format in cell 576 which, in addition to including a $Gene field, also includes an $AV (e.g., answer value) field. Here, when the answer format rule is met (e.g., IF AV; if there is an answer value in an answer cell) so that answer format 576 is used to generate a response file, in addition to populating the $Gene field with one of the genes from column 556, the $AV field is populated with a value from an associated answer cell there below. For instance, for gene ABCB1 the answer cell 578 includes a value 1% and therefore, if intent C applies and is qualified by gene parameter ABCB1 the answer format rule in cell 576 is met and the response tile includes the phrase "Provider sees a pathogenic mutation in ABCB1 in 1% of pancreatic cancer patients". In negative answer cell 580, the rule is that if an answer cell there below is blank, then that cell format is used to generate a response file.

While there are two answer format rows shown in each of FIGS. 21 and 10 (e.g., the answer format row and the negative answer format row), in other cases there may be three or more answer formats that change based on values in specific answer fields there below to support more complex answer generation schemes.

Again, as in the case of the data presented in FIG. 21, the data in FIG. 22 only shows a small subset of the gene data accessible via left and right and up and down scrolling through parameters and intents. For instance, the genes in parameter column 556 may include an entire gene panel (e.g., hundreds of genes) and the intents in row 552 may include hundreds or even thousands of intents.

Figure 23:
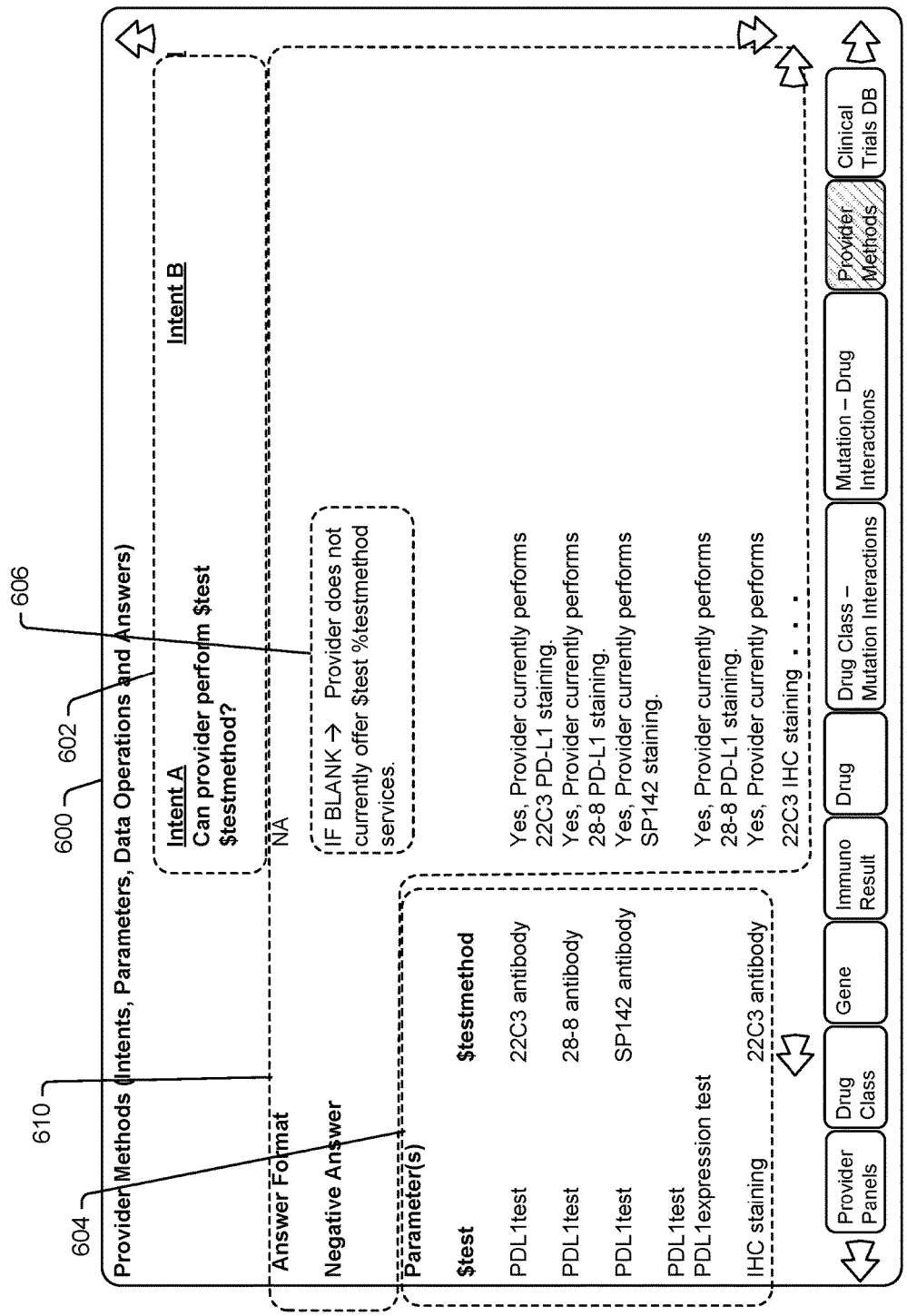
FIG. 23 is similar to FIG. 22, albeit including a screen shot for specifying provider methods.

FIG. 23 shows another administrative screen shot 600 similar to the FIG. 21 and FIG. 22 shots, albeit corresponding to a provider methods data set. The spreadsheet representation in FIG. 23 is similar to the representations in FIGS. 21 and 22 including an intent row 602, an answer format section 610, and a parameters column 604. One difference in FIG. 23 is that the first intent A includes two parameter fields and the parameters section includes first and second parameter rows, one for each of the parameter fields in intent A. More specifically, the parameters section include a first column listing tests and a second column that lists test methods for populating associated $test and $testmethod fields in the intent statement. In addition, in at least some cases answer formats like the negative answer format shown in cell 606 will include two or more parameter or value fields. Here operation is similar to that described above, albeit using two parameters to instantiate specific intents and final response files.

Referring again to FIG. 20, interface screen shots akin to those described in FIGS. 21 through 23 are included in a system for specifying intents, parameters and answer formats for each of the information types associated with the sub-databases illustrated. Some of the screen shots will include specific scripted answers for specific intents while others will rely upon answer formats, rules for one or all the formats and populating answer fields with intent parameters and/or database values that appear in answer cells as described above. Other screen shots and tool combinations are contemplated.

In at least some cases it is contemplated that the system will enable an oncologist to request visual access to query answers and/or related information (e.g., associated documents (e.g., clinical trial information, drug label warnings, etc.). For instance, an oncologist may enunciate "Make that answer available with the system web platform," causing the system to render the most recently broadcast answer available via a nearby or oncologist dedicated computer display screen. In at least some cases it is contemplated that the system will enable an oncologist or other user to provide queries via a typed question instead of an audible query. For instance, rather than speaking a question, an oncologist may type the query into a mobile phone or other computing device, and the query may be processed as described herein.

Figure 24:
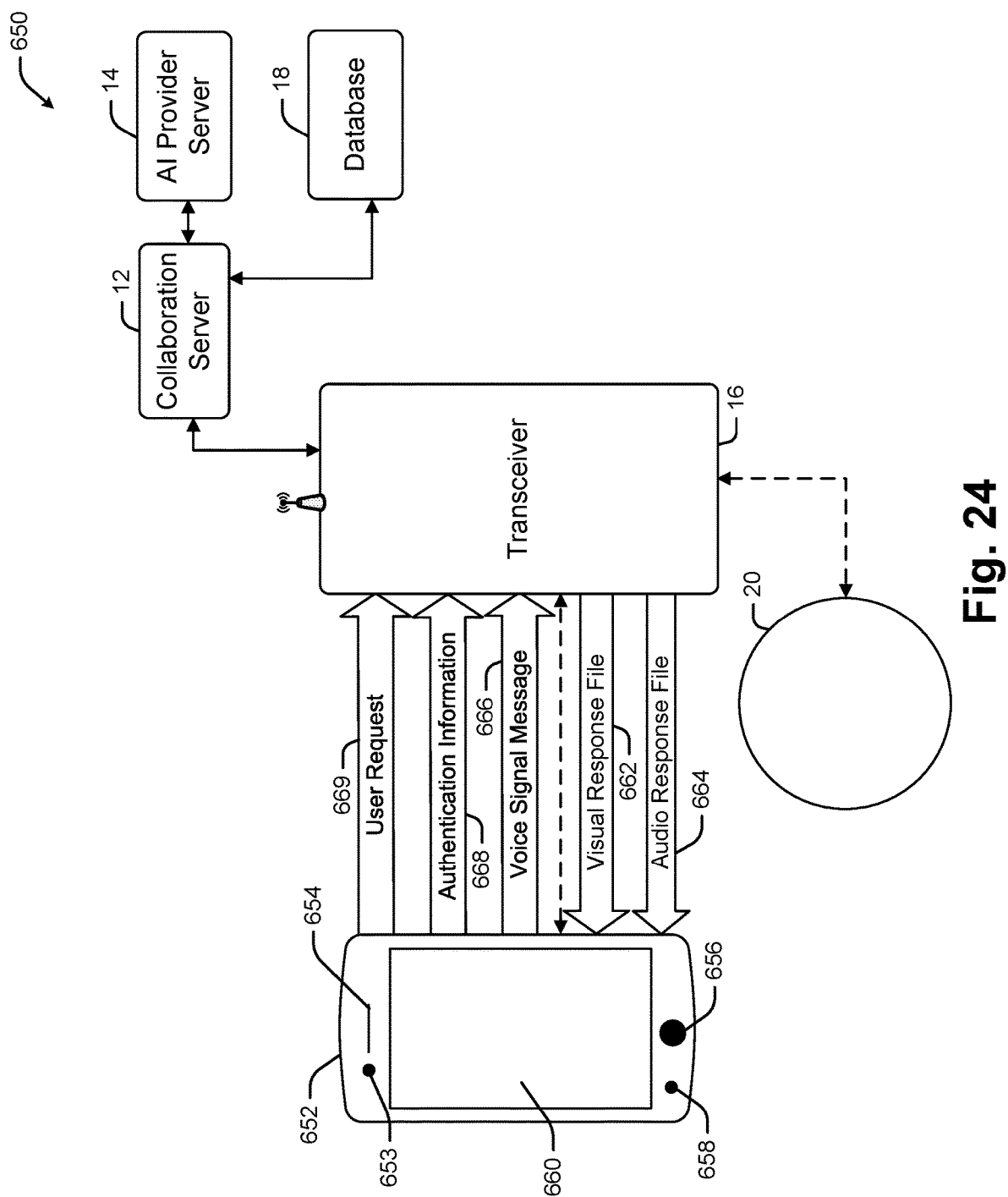
FIG. 24 is a schematic diagram of an exemplary fourth exemplary system including a mobile device.

Referring now to FIG. 24, a fourth exemplary system 650 including a mobile device 652 is depicted. The fourth exemplary system can include the collaboration device 20, the collaboration server 12, the AI provider server 14, and the database 18. The collaboration device 20, the collaboration server 12, the AI provider server 14, and the database 18 can be linked together as described above in conjunction with FIG. 1. The mobile device 652 can be used in conjunction with the collaboration device 20 to authenticate user credentials and/or onboard the oncologist, as well as perform at least a portion of the functions of the collaboration device 20 (e.g., handle queries about a patient) among other suitable uses.

The mobile device 652 can be a smartphone, a tablet, or another suitable mobile computing device. The mobile device 652 can include a camera 653, a speaker 654, a fingerprint sensor 656, and input button 658, and a touchscreen 660, Similar to the collaboration device 20, the mobile device 652 can transmit 666 voice signal messages to the transceiver 16 for processing by the collaboration server 12 and/or AI provider server 14. The mobile device 652 can also receive 662 visual response files and/or receive 664 audio response files generated based on the voice message signals from the transceiver 16.

In addition, the mobile device 652 can transmit 668 authentication information to the transceiver 16 in order to unlock the collaboration device 20. The collaboration device 20 may be configured to request authentication from the oncologist at predetermined time points (e.g., every thirty minutes, every hour, etc.) or when the oncologist moves the collaboration device 20. For example, the collaboration device 20 can detect it has been moved if contact with the transceiver 16 is lost. The oncologist may have moved the collaboration device to another room in the same building (e.g., a hospital) or to another building entirely (e.g., another hospital, a home office, etc.). It is appreciated that the collaboration device 20 is mobile and can be moved to and used in a variety of locations with suitable connectivity (e.g., wireless internet).

The mobile device 652 can have a mobile device application (not shown) installed that can determine what authentication credentials are required at a specific time and display notification about required authentication credentials on the touchscreen 660 when applicable. For example, if the mobile device application determines that a half hour has passed since the last authentication, the mobile device application can output a notification that the oncologist needs to reauthenticate before using the full capabilities of the collaboration device 20 (e.g., querying the collaboration device 20 about a specific patient). In some embodiments, the mobile device application may not output a notification, and the collaboration device 20 can prompt the oncologist to reauthenticate when the oncologist attempts to query the collaboration device.

The mobile device 652 can provide 668 multiple forms of authentication information to the transceiver. The authentication information can include a fingerprint scan generated using the fingerprint sensor 656, a picture of the face of the oncologist generated using the camera 653, and/or a text password. In some embodiments, the mobile device application can provide the raw fingerprint scan, the picture, and/or the password to the transceiver 16, and another process (e.g., a process in the collaboration server 12) can determine if the authentication information is sufficient (e.g., the fingerprint scan sufficiently matches a predetermined fingerprint scan associated with the oncologist) or not. In other embodiments, the mobile device application can determine if the authentication information is sufficient or not, and transmit 668 authentication information indicating whether the authentication information is sufficient or not (e.g., a Boolean yes/no). If the authentication information is sufficient, the collaboration device 20 can resume full operation.

The mobile device 652 can also transmit 669 a user request (i.e., an oncologist request) to the transceiver for processing by the collaboration server 12. The user request can be a request for a human (e.g., an administrator or in some cases, a medical practitioner) to review a note, clinical report, molecular report, patient, case, etc., a product suggestion (e.g., a collaboration device 20 capability the oncologist would like to add), product fulfillment requests (e.g., an order for testing kits), a status of an ordered test kit (e.g., a liquid or tissue based biopsy test kit for executing a molecular test), a recommendation for a tumor board session for a patient, or other requests that may be more easily disseminated by a human than a computer process or requests not necessarily related to intent fulfillment. Some user requests may be generated by and transmitted from the mobile device 652 and/or the collaboration device 20 based on a voice signal captured from the oncologist. The AI database 14 can determine the intent of the user request to be an order for testing kits or a request for manual review of a particular case, for example. The text form of the voice signal and any associated information (e.g., the intent) can then be transmitted to the collaboration server 12, which can then transmit the text form of the voice signal and any associated information to an administrator and/or a suitable computer process. If the user request includes a recommendation of a patient for a tumor board or a clinical trial, relevant information about the patient can also be transmitted along with the request, greatly reducing the need for filling out applications for clinical trials and/or tumor boards.

In some embodiments, the processes performed by the mobile device 652 (e.g., authentication processes, transmitting 669 user requests, etc.) can be performed by the collaboration device 20.

Figure 25:
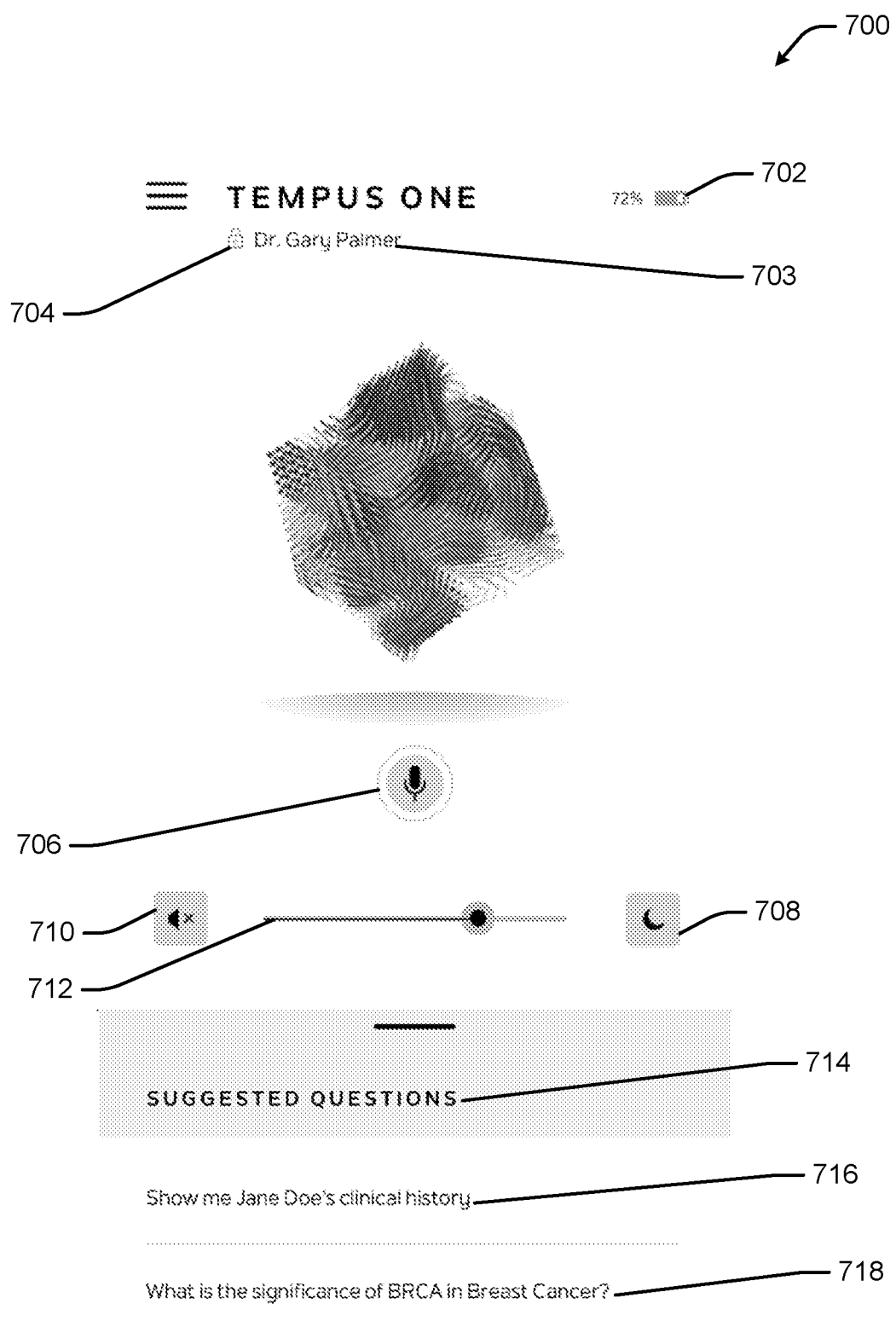
FIG. 25 is a screen shot of a mobile application.

Referring now to FIG. 24 as well as FIG. 25, a mobile application screen shot 700 is shown. The mobile application screen shot 700 can be a portion of the mobile device application included in the mobile device 652. The mobile application screen shot 700 can include a battery level indicator 702 indicating a battery level of the collaboration device 20, a username 703 corresponding to the current oncologist that is logged in, an authentication indicator 704 indicating whether or not the oncologist has been authenticated by the mobile device 652, a microphone button 706, a night mode button 708, and a mute button 710. The oncologist can select the microphone button 706 instead of enunciating a wake word or phrase (e.g., "Tempus ONE") in order to prompt the collaboration device 20 and/or the mobile device 652 to record a voice signal. The night mode button 708 can control the darkness and/or colors displayed by the mobile device application.

The mobile application screen shot 700 can include a slider 712. The oncologist can actuate the slider 712 to control a volume of the collaboration device 20. The mobile application screen shot 700 can include a suggested questions section 714 that can display example queries and/or common queries that oncologists ask the collaboration device 20. For example, a first question 716 can show the oncologist how to inquire about a specific patient, and a second question 718 can show the oncologist how to inquire about medical questions not specific to the patient.

Figure 26:
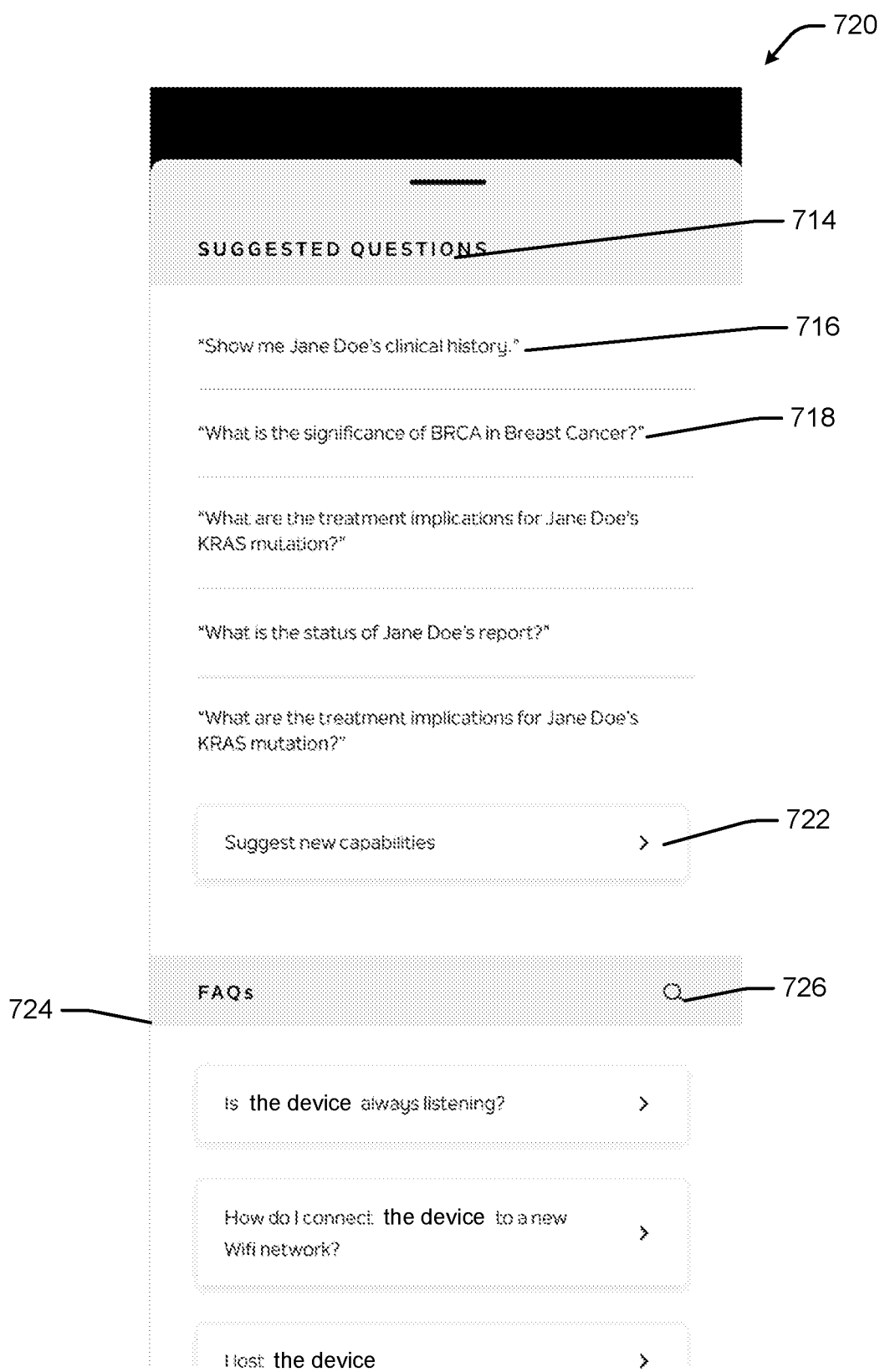
FIG. 26 is a second screenshot of the mobile application in FIG. 25.

Referring now to FIGS. 24 and 25 as well as FIG. 26, a second mobile application screen shot 720 is shown. The second mobile application screen shot 720 can include the suggested questions section 714, the first question 716, and the second question 718 included in the mobile application screenshot 700 shown in FIG. 25. In FIG. 26, the suggested questions section 714 is shown to include additional suggested questions. The second mobile application screen shot 720 can include a suggest new capabilities button 722. The oncologist can select the suggest new capabilities button 722 and provide a suggestion about new capabilities in a popup box, for example. The mobile device 652 can then transmit the suggestion to an administrator.

The second mobile application screen shot 720 can include a frequently asked questions (FAQs) section 724 that includes common questions about the functionality of the collaboration device 20. The second mobile application screen shot 720, and more specifically the FAQs section 724, can include a search button 726 that the oncologist can select in order to search a set of FAQs.

Figure 27:
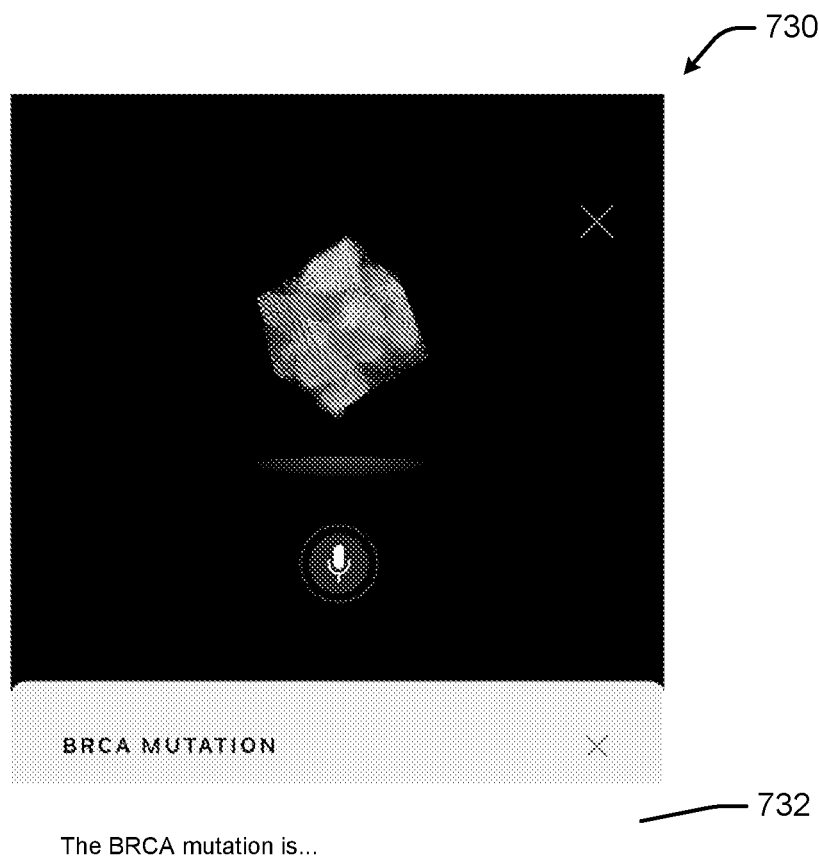
FIG. 27 is a third screenshot of the mobile application in FIG. 25.

Referring now to FIG. 25 as well as FIG. 27, a third mobile application screen shot 730 is shown. The third mobile application screen shot can include an answer 732 to the second question 718 shown in FIG. 25. The answer 732 can include text and may be included in a popup box that is displayed when the oncologist selects the second question 718.

Figure 28:
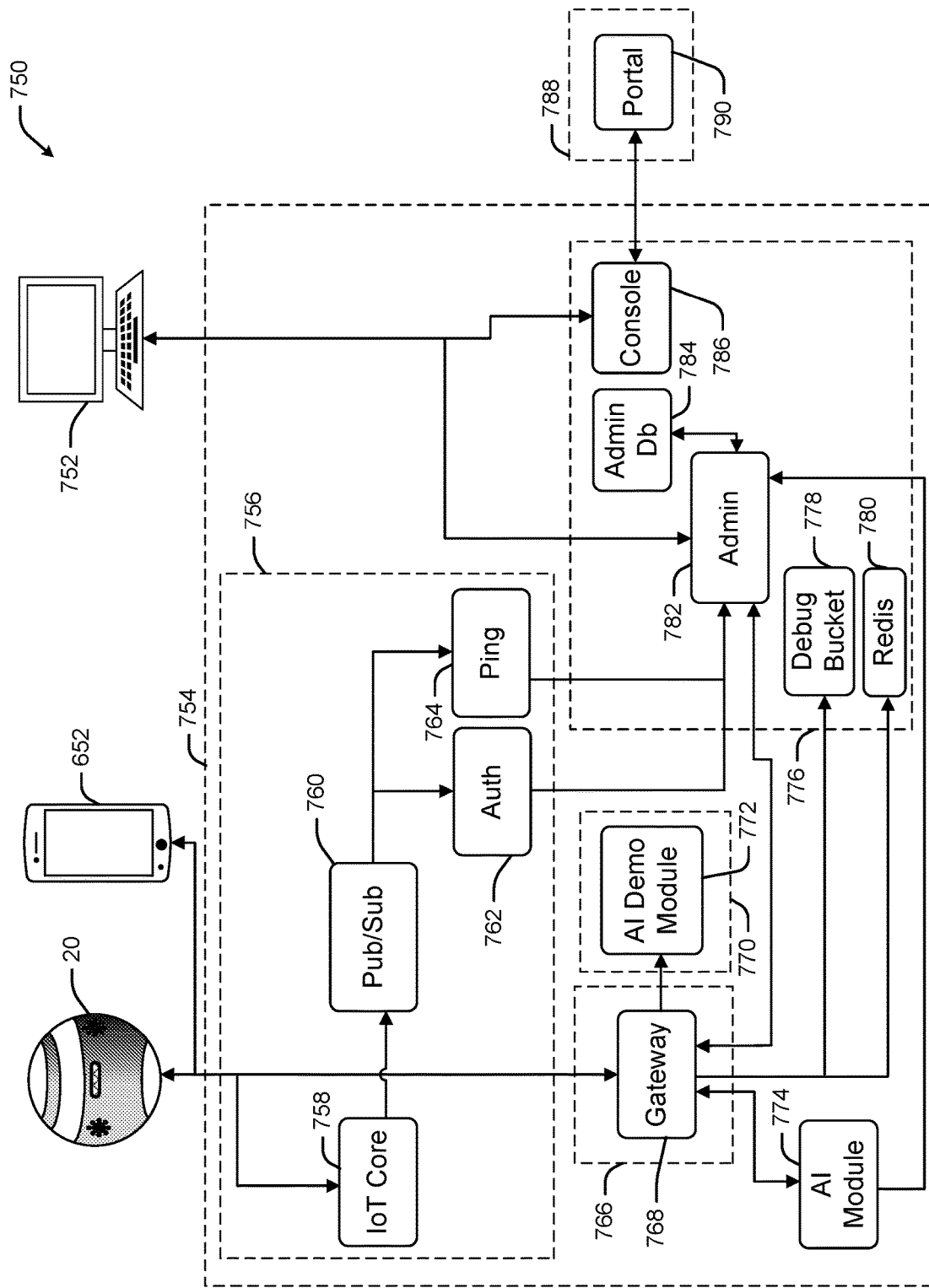
FIG. 28 is a schematic diagram of a fifth exemplary collaboration system.

Referring now to FIG. 28, a fifth exemplary collaboration system 750 is shown. The fifth exemplary system 750 can include an administrator device 752 such as a laptop or desktop computer. An administrator can use the administrator device 752 to analyze data aggregated from a number of oncologists, update firmware in the collaboration device 20, analyze requests from an oncologist, update a set of intents (e.g., in Dialogflow), and other suitable tasks related to operation of the collaboration device and/or the mobile device 652.

The fifth exemplary system 750 can include a cloud architecture 754 that includes a number of modules that may be located remotely (e.g., on one or more servers) in relation to the administrator device 752, collaboration device 20, and/or the mobile device 652. The collaboration device 20 and/or the mobile device 652 can be linked to an IoT core module 758 that can handle authentication requests and other communications from the collaboration device 20. The IoT core module 758 can be linked to a pub/sub module 760 that is linked to an authentication module 762 and a ping module 764. The pub/sub module 760 can transmit updates (e.g., status updates) to the collaboration device 20 and/or the mobile device. The authentication module 762 can receive authentication requests from the collaboration device 20 and/or the mobile device 652. The pub/sub module 760 can direct communications from the IoT core module 758 to either the authentication module 762 or the ping module 764 as appropriate. The pub/sub module 760, the IoT core module 758, the authentication module 762, and/or the ping module 764 can be stored on a first server 756.

The collaboration device 20 and/or the mobile device 652 can be linked to a gateway module 768 that may be included in a second server 766. The gateway module 768 can include at least a portion of the processes included in the collaboration server 12. The collaboration device 20 and/or the mobile device 652 can transmit requests (e.g., a user request transmitted from the mobile device 652) and/or voice signal messages to the gateway module 768. The gateway module 768 can be linked to an AI module 774. The AI module 774 can include at least a portion of the processes included in the AI provider server 14 (e.g., voice signal extraction processes) and may receive voice signals, extract intents from the voice signals, and transmit data response to the gateway module 768 for transmitting to at least one of the collaboration device 20 and the mobile device 652. In some embodiments, the Dialogflow suite can be included in the AI module 774. The gateway module 768 can also be linked to a debug bucket module 778 and a redis module 780 included in a third server 776. The gateway module 768 can be linked to an AI demo module 772 included in a fourth server 772.

The third server 776 may only be fully accessible (e.g., configured to allow full control and/or modification of processes) by the administrator device 752 and not the collaboration device 20 and/or the mobile device 652. The third server 776 can include an administrator module 782 that the administrator device 752 can access in order to update collaborator device 20 firmware, define intents, update intent fulfillment processes, and perform other administrator functions. The administrator module 782 can also process and/or transmit user requests (e.g., an order for testing kits) to the administrator device 752. The administrator and/or the administrator device 752 can then analyze the user request and proceed accordingly. For example, an order for testing kits can be transmitted to an order fulfillment center. As another example, the oncologist can request a manual review of a particular case, and the request can be transmitted to an administrator who may assign the case to a medical practitioner for review within a predetermined timeframe, for example, twenty-four hours.

The third server 776 can include a console module 786 linked to the administrator device 752. The console module 786 can perform administrative duties. An administrative database 784 can be linked to the administrator module 782. The console module 786 can be linked to a portal module 790 included in a fifth server 788. The portal module 790 may provide an interface for oncologists to review molecular tests reports.

The fifth system 750, and more specifically the administrator module 782, the administrator device 752, the console module 786, and/or the administrator database 784 may track a number of collaboration devices 20. More specifically, the fifth system 750 can track if each collaboration device 20 is connected (e.g., in contact with the cloud architecture 754) or active (e.g., processing a query), what version of firmware each collaboration device 20 is running, and relatively static information such as an owner and/or institution associated with the device.

The administrator module 782 can include processes for analyzing queries from oncologists and generate usage data about how oncologists are using the collaboration device 20, how many test kits are being ordered for different case types, how often questions about specific sections of generated clinical reports are asked about FDA on/off label drug questions, therapies associated with a specific variant, what actions oncologists take in different scenarios (e.g., what questions are being asked), and other suitable data.

It is understood that the servers 756, 766, 770, 776, and 788 can each include more than one server. Additionally, at least some of the modules and/or processes included in the cloud architecture 754 can be implemented with infrastructure-as-code that can be migrated across clouds like AWS, Google Cloud, Azure, etc.

The fifth system 750, and more specifically the administrator module 782, the administrator device 752, the console module 786, and/or the administrator database 784 can track intents being processed across a number of cases (e.g., thousands of cases) and/or other actions one or more collaboration devices 20 are taking or developments being made in the medical community (e.g., new research articles, studies, and/or treatment techniques) and provide "nudges" to oncologists in order to potentially make the oncologists aware of information they potentially may not be aware of. The fifth system 750 may ask the oncologist for permission to analyze clinical data generated by the oncologists.

Other data the administrator module 782, the administrator device 752, the console module 786, and/or the administrator database 784 can track may include numbers of test kits ordered by an oncologist in a predetermined timeframe (which may indicate if onboarding is successful), how many answers (e.g., statistics) or other information (Tempus Insights, actionable mutations, etc.) the collaboration devices 20 provide that are not included in clinical reports, periodically scheduled surveys of oncologists about the collaboration device 20 and/or the mobile application (e.g., answers to "What information would be most helpful when making clinical decisions?"), what portions of clinical reports are asked about the most often (either for an individual oncologist or for multiple oncologists), how oncologists behave on a macro scale (e.g., for a given cancer type and/or molecular variation, what tests did other oncologists run), how similar patients behaved to certain therapies (e.g., how many patients presented with XXX molecular mutation had variant YYY, and of those, how many had ZZZ response to therapy AAA over time duration BBB), or other suitable data.

In some embodiments, the administrator device 752 may provide at least some of the functionalities of the collaboration device 20, albeit tailored for the administrator. For example, the administrator device 752 may be suitable equipped (e.g., with a microphone and speakers) and configured to answer questions such as "where is sample [x] stored?", "what is the SOP for scenario y", etc. that may only be relevant to the administrator. In some embodiments, the administrator may use the collaboration device 20 with an administrator-specific set of intents that oncologists may not be able to use (i.e., are restricted from using). The administrator may enunciate e.g. Tempus ONE, where is sample [x] stored?" and the collaboration device can determine the intent of the query is to know the location (e.g., a warehouse) of the sample [x], and provide an appropriate visual and/or audible response.

Some data can then be used to customize the user experience of each oncologist. For example, data about what portions of clinical reports are the most asked about can be used to custom tailor report layout and format suggestions that an oncologist could accept (i.e., update the report layout and/or format) or reject (i.e., keep the same report layout and/or format) after receiving the notification. Then, reports displayed on the portal module 790 or via the mobile application (e.g., on the touchscreen 660) can follow the updated template and/or layout. Additionally or alternatively, the oncologist can provide suggestions about the report layout and/or format, and the report layout and/or format can be updated accordingly.

The fifth system 750 can provide nudges to the oncologist using the collaboration device 20 and/or the mobile device 652 using data collected by the fifth system 750. The nudges can be provided to an oncologist without the oncologist needing to ask a question. One nudge can include the fifth system 750 determining a treatment that is most successful for patients similar to a patient the oncologist is analyzing. The most successful treatment can be determined based on molecular data of the patient (e.g., molecular mutations and/or variants), age, gender, etc. as well as the success rates of various treatments in populations with the same molecular data, age, gender, etc. Another nudge can include informing the oncologist of cancer boards, clinical trials, and other programs within a predetermined radius (e.g., fifteen miles of the medical facility the oncologist is located at) the patient is eligible for. Furthermore, the fifth system 750 can provide the nudge to the oncologist at a predetermined time before an upcoming patient visit (e.g., within twenty-four hours), and may only provide cancer boards, clinical trials, and other programs that were not available when the patient last visited and/or the last clinical report was generated for the patient. The oncologist can be notified by controlling the indicator lights 50 in a predetermined pattern and/or color, outputting specific sounds at the speakers 44, displaying notifications on the mobile device 652, vibrating the collaboration device 20 and/or mobile device 652 using a haptic signaling component, etc. Additionally, the findings of any tumor boards and/or trials and/or any action plans can be provided to the oncologist or cite a specific action plan following a tumor board. The oncologist can then easily retrieve findings of a given tumor board.

Yet another nudge can include controlling the indicator lights 50 in a predetermined pattern and/or color, outputting specific sounds at the speakers 44, displaying notifications on the mobile device 652, vibrating the collaboration device 20 and/or mobile device 652 using a haptic signaling component, etc., to indicate that a new molecular report or clinical report has become available for the patient.

Still another nudge can include notifying the oncologist of newly-available content (e.g., research papers, articles, journals, posters, etc.) that is relevant to the practice area of the oncologist or for the patient. Oncologists can opt in for notifications associated with multiple data sources, content types, cancer subtypes and/or diseases, molecular mutations/variants, treatments (FDA on-label, off-label, investigational, etc.) as well as clinical trials. A further nudge can include notifying the oncologist that an ordered test may be completed more efficiently with an alternative test (e.g., using an xF liquid biopsy test instead of a tissue-specific xT panel). The test kit may not be able to be processed due to insufficient tissue, but the oncologist will only see the newly-suggested test.

A still further nudge can include notifying an oncologist of various patient tests and orders that other oncologist have made for similar patients and/or cases. For example, the nudge can include a notification that a peer oncologist (or x % of other oncologists) has placed a test order for a similar patient. In some embodiments, the fifth system 750 can determine if oncologists have ordered PDL1 IHC with a specific test, and inform the oncologist whether or not the test is a good option for the patient. Sometimes, oncologists do not want to be the first to use a new vendor and may also want to consult their peers to better understand the type of information returned via PDF report, through the portal module 790 or the mobile application on the mobile device 652. Knowing that other oncologist peers in an institution are ordering tests for x % of certain patient cohorts may allow the oncologist to operate with a knowledge of how other oncologists are treating similar patients.

Still regarding test kits, yet another nudge can include notifying the oncologist that their stock of test kits is running low (e.g., below a predetermined threshold). Some nudges can include information about financial assistance that may be available for a test kit. Once an oncologist is informed of test kit options, the oncologist can order the test kit and/or apply for financial aid by enunciating an appropriate command to the collaboration device 20 and/or the mobile device 652. The fifth system 750 may then automatically fill out any test kit order forms and/or financial aid applications.

Some nudges can inform an oncologist of nearby continuing medical education (CME) courses and/or allow the oncologist to enroll in CME-crediting courses or highlight local and/or online offerings within the particular specialty and/or area of focus of the oncologist.

Figure 29:
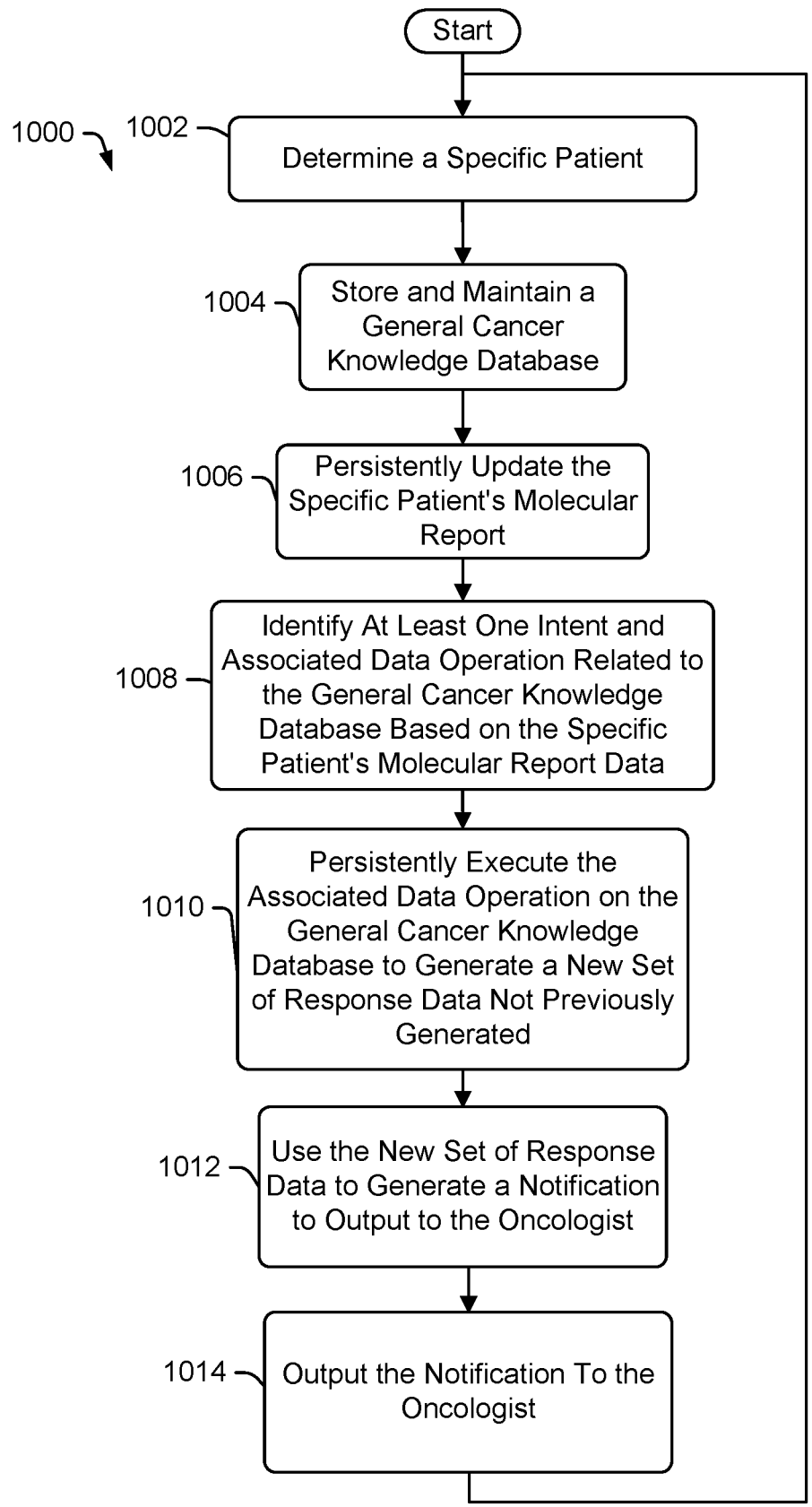
FIG. 29 is a flowchart of a process for generating supplemental content for a physician based on a molecular report associated with a specific patient.

Referring now to FIGS. 19, 24, and 28 as well as FIG. 29, a process 1000 for generating supplemental content for a physician based on a molecular report associated with a specific patient is shown. The process 1000 can be used to provide patient-specific nudges to the oncologist. The process 1000 can identify information that may be relevant to treatment of a patient and that the oncologist may not have considered when querying the collaboration device 1000. In this way, the collaboration device 20 may assist the oncologist in treating the patient using therapies, drugs, clinical trials, and/or other treatment techniques applicable to the specific patient that the oncologist may not be aware of or may not have considered previously. The process 1000 may also provide the oncologist 1000 with information about how other oncologists have treated similar patients (e.g., similar gnomically and/or being diagnosed with a similar cancer type). The process 1000 may be executed by a suitable system such as the fifth exemplary system 750.

At 1002, the process 1000 can determine a specific patient. In at least some cases, the process 1000 can be executed in parallel and/or after the process 450 is being executed and/or after the process 450 has been executed. The process 1000 can determine that the specific patient is the same specific patient identified by the process 450. In at least some cases, the process 1000 can be executed along with the process 1000 to effectively form a single process. The process 1000 can then proceed to 1004.

At 1004, the process 1000 can store and maintain a general cancer knowledge database. The general cancer knowledge database can include raw data and/or processed data about a number of patients including molecular reports, presence of conditions such as diabetes, heart disease, etc., information about treatment history such as drugs and/or therapies that each patient has taken as well as responses to the drugs and/or therapies (e.g., a patient was successfully treated using drug FFF), and/or other suitable data about patients. Data associated with each patient can be persistently updated as additional information becomes available. The general cancer knowledge database can include non-patient specific information about specific topics (e.g., efficacy of specific drugs in treating specific cancer states, clinical trials information, drug class—mutation interactions, genes, etc.) based on accepted industry standards or empirical information derived by the service provider as well as information about the service provider's system capabilities (e.g., information about specific tests and activities performed by the provider, test requirements, etc.) The general cancer knowledge database can include the KDB 504 described above. The general cancer knowledge database can include information about available clinical trials, treatments, studies, academic papers, CLE courses, or other available resources. The process 1000 can then proceed to 1006.

At 1006, the process 1000 can persistently update the specific patient's molecular report. For example, the process 1000 can update relevant clinical trials included in the molecular report. The process 1000 can then proceed to 1008.

At 1008, the process 1000 can automatically identify at least one intent and associated data operation related to the general cancer knowledge database based on the specific patient's molecular report data. The at least one intent can be related to drugs, genes, testing methods, etc. as described above. The at least one intent can also be related to a specific cancer the specific patient has been diagnosed as having. At least some of the intents may be intents the oncologist has not queried the collaboration device 20 about previously. The process 1000 can then proceed to 1010.

At 1010, the process 1000 can persistently execute the associated data operation on the general cancer knowledge database to generate a new set of response data not previously generated. In some cases, the process 1000 can persistently execute multiple associated data operations on the general cancer knowledge database. Persistently executing the general cancer knowledge database can allow the process 1000 to provide updated information (i.e., the new set of response data) to the oncologist. Additionally, the new set of response data may provide be used to provide information related to the specific patient that the oncologist may not have been aware of previously. For example, the new set of response data can be used to inform the oncologist of how various treatment options perform on other patients with similar genomic profiles. As another example, the new set of data can be used to inform the oncologist of tests that were ordered for other patients diagnosed with the same cancer as the specific patient and that have similar genomic profiles (e.g., the presence of a specific gene mutation). The process 1000 can then proceed to 1012.

At 1012, the process 1000 can, upon generating a new set of response data, use the new set of response data to generate a notification to output to the oncologist. In some cases, the notification can be an audible response file the process 1000 generates based on the new set of response data. In some cases, the notification can be a visual indicator the process 1000 generates based on the new set of response data. The visual indicator can include a question related to the new set of response data. For example, the question can be a suggested question that can be answered using the new set of response data. In this example, if the new set of response data includes information about patient response to a certain treatment (e.g., patients with mutation XXX that received treatment YYY survived cancer type VWWV VVV % of the time), the suggested question can be "How many patients with mutation XXX survived when given treatment YYY?" or "What treatment is most effective for patients with mutation XXX and cancer type VWWV?" The process 1000 can then proceed to 1014.

At 1014, the process 1000 can output the notification generated at 1012 to the oncologist. If the notification is an audible response file, the process can output the audible response file at the collaboration device 20 (e.g., at the speakers 44) and/or the mobile device 652 (e.g., at the speaker 654). If the notification is a visual indicator, the visual indicator can be output at the collaboration device 20 (e.g., at the display screen(s) 48) and/or the mobile device 652 (e.g., at the touchscreen 660). If the visual indicator is a suggested question, the suggested question can be displayed in the suggested question section 714 described above. The notification can function as a nudge. Thus, the process 1000 can generate and provide at least some of the nudges described above to the oncologist.

Figure 30:
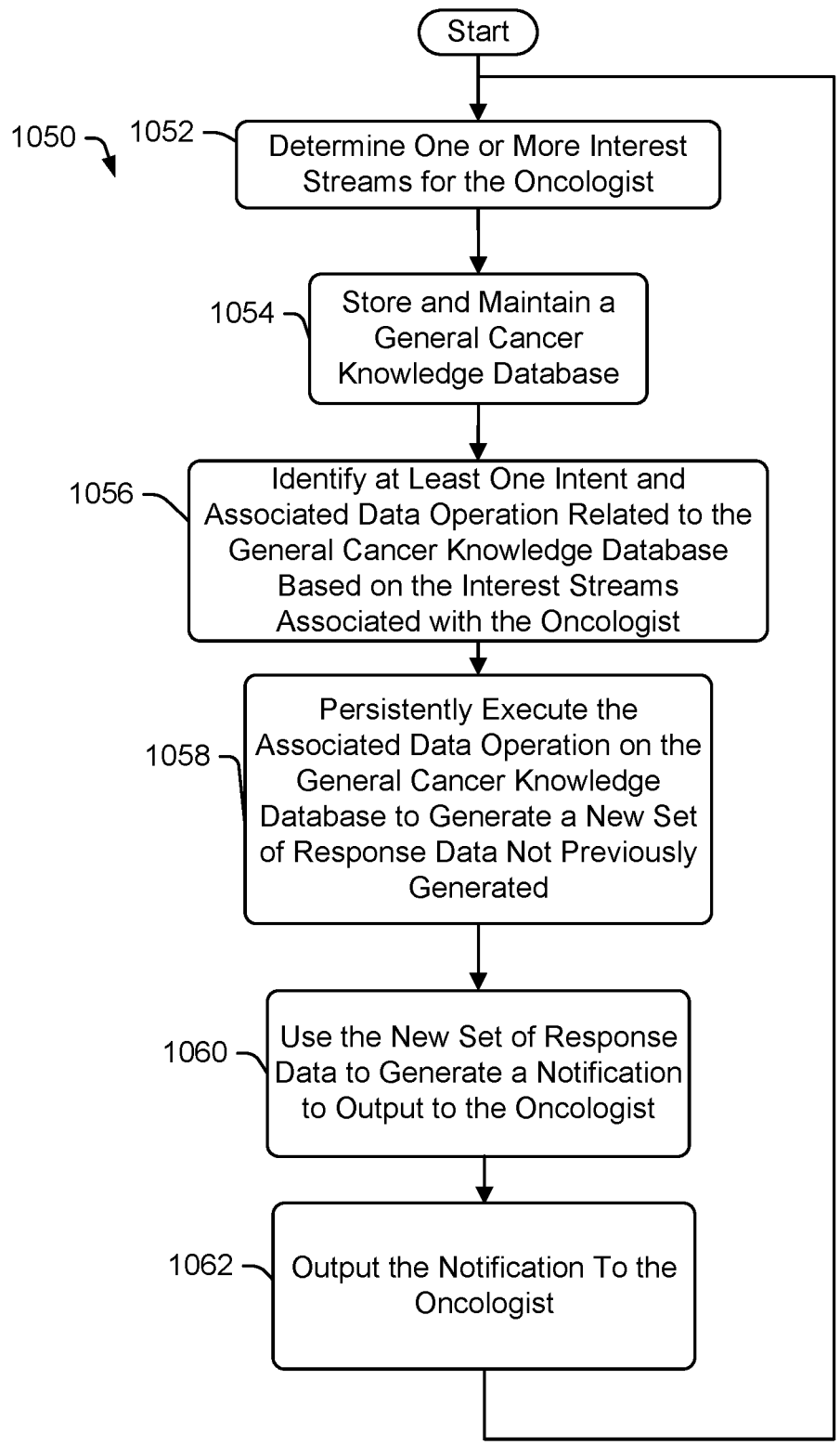
FIG. 30 is a flowchart of a process for generating non-patient-specific supplemental content for a physician.

Referring now to FIGS. 19, 24, and 28 as well as FIG. 30, a process 1050 for generating non-patient-specific supplemental content for a physician is shown. The process 1050 can be used to provide non-patient-specific nudges to the oncologist. The process 1050 can identify information that may be generally relevant to the oncologist, such as newly available treatments, studies, academic papers, etc. The process 1050 can reduce the need for the oncologist to search for new developments in the field(s) the oncologist practices in. For example, if the oncologist specializes in treating breast cancer patients, the process 1050 may provide information that is may be useful for treating breast cancer patients. The process 1050 may be executed by a suitable system such as the fifth exemplary system 750.

At 1052, the process 1050 can determine one or more interest streams for the oncologist. The interest streams can include newly available clinical trials, treatments, studies, academic papers, CLE courses, or other suitable types of information and/or programs related to a cancer type that may be useful to the oncologist. In some embodiments, the oncologist can provide (e.g., audibly) the types of interest streams and/or cancer types of interest to the process 1050. The process 1050 may automatically determine the interest streams based on the history of the oncologist. For example, the oncologist may generally treat breast cancer and lung cancer patients, and the process 1050 can select interest streams available that are related to those cancer types. The process 1050 can then proceed to 1054.

At 1054, the process 1050 can store and maintain a general cancer knowledge database. The general cancer knowledge database can include raw data and/or processed data about a number of patients including molecular reports, presence of conditions such as diabetes, heart disease, etc., information about treatment history such as drugs and/or therapies that each patient has taken as well as responses to the drugs and/or therapies (e.g., a patient was successfully treated using drug FFF), and/or other suitable data about patients. Data associated with each patient can be persistently updated as additional information becomes available. The general cancer knowledge database can include non-patient specific information about specific topics (e.g., efficacy of specific drugs in treating specific cancer states, clinical trials information, drug class—mutation interactions, genes, etc.) based on accepted industry standards or empirical information derived by the service provider as well as information about the service provider's system capabilities (e.g., information about specific tests and activities performed by the provider, test requirements, etc.) The general cancer knowledge database can include the KDB 504 described above. The general cancer knowledge database can include information about available clinical trials, treatments, studies, academic papers, CLE courses, or other available resources. The process 1050 can then proceed to 1056.

At 1056, the process 1050 can automatically identify at least one intent and associated data operation related to the general cancer knowledge database based on the interest streams associated with the oncologist. For example, the at least one intent can be related to identifying whether or not any new academic papers about a certain cancer type (e.g., breast cancer) are newly available (e.g., published in the last week), identifying whether or not any new clinical trials for a certain cancer type (e.g., lung cancer) are newly available, identifying whether or not any new treatment options for a certain cancer type (e.g., breast cancer) are newly available, or other suitable intents. In this example, the associated data operations can include searches for any new available academic papers, clinical trials, and treatment options. At least some of the intents may be intents the oncologist has not queried the collaboration device 20 about previously. The process 1050 can then proceed to 1058.

At 1058, the process 1050 can persistently execute the associated data operation on the general cancer knowledge database to generate a new set of response data not previously generated. In some cases, the process 1050 can persistently execute multiple associated data operations on the general cancer knowledge database. Persistently executing the general cancer knowledge database can allow the process 1050 to provide updated information (i.e., the new set of response data) to the oncologist. The new set of data can be used to inform the oncologist of newly available academic papers, clinical trials, and treatment options, etc. that are available. The process 1050 can then proceed to 1060.

At 1060, the process 1050 can, upon generating a new set of response data, use the new set of response data to generate a notification to output to the oncologist. In some cases, the notification can be an audible response file the process 1050 generates based on the new set of response data. In some cases, the notification can be a visual indicator the process 1050 generates based on the new set of response data. The visual indicator can include a question related to the new set of response data. For example, the question can be a suggested question that can be answered using the new set of response data. In this example, if the new set of response data includes information about a newly available breast cancer treatment (e.g., treatment YYY is now available for breast cancer patients), the suggested question can be "Are there any new treatment options available for breast cancer patients?" The process 1050 can then proceed to 1062.

At 1062, the process 1050 can output the notification generated at 1060 to the oncologist. If the notification is an audible response file, the process can output the audible response file at the collaboration device 20 (e.g., at the speakers 44) and/or the mobile device 652 (e.g., at the speaker 654). If the notification is a visual indicator, the visual indicator can be output at the collaboration device 20 (e.g., at the display screen(s) 48) and/or the mobile device 652 (e.g., at the touchscreen 660). If the visual indicator is a suggested question, the suggested question can be displayed in the suggested question section 714 described above.

Figure 31:
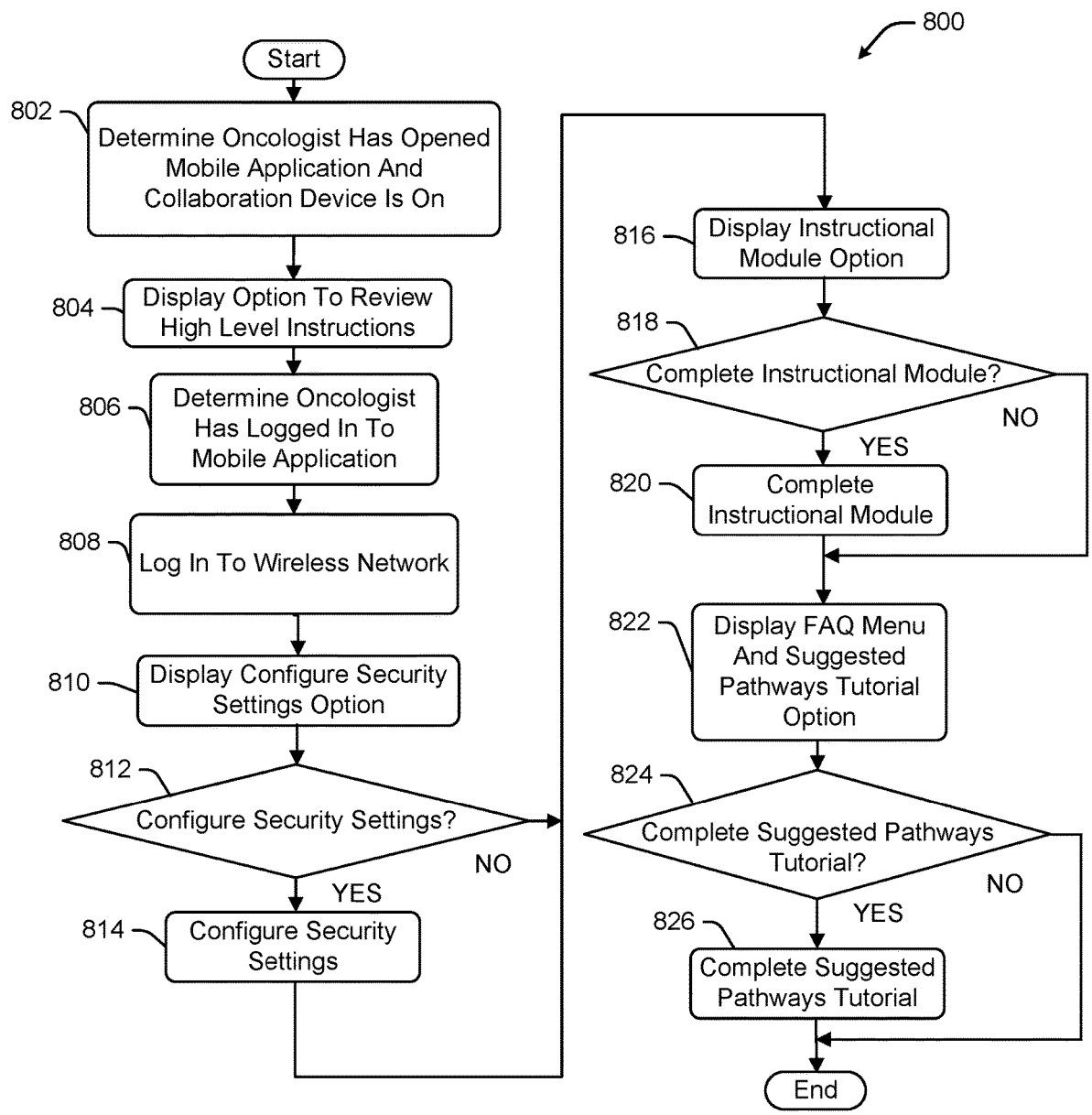
FIG. 31 is a flowchart of a process that may be used for onboarding an oncologist.

Referring now to FIG. 31, a process 800 that may be used for onboarding an oncologist is shown. At block 802, the process 800 can determine a user (e.g., an oncologist) has opened a mobile application, and that a collaboration device is on. The mobile application can be the mobile application included on the mobile device 652, and the collaboration device can be the collaboration device 20 described above. The collaboration device 20 may output "Hello, your Tempus ONE is ready for setup. Please download the Tempus ONE mobile app to begin setup" using the speakers 44. Control passes to block 804, where the process 800 can display an option to review high level instructions to the oncologist. The option can be displayed on a user interface such as the touchscreen 660. Control passes to block 806, where the process 800 can determine if the oncologist has logged in to the mobile application.

Once the oncologist has logged in, the control passes to block 808, where the process 800 can attempt to log the mobile device 652 in to a wireless network that the collaboration device is connected to. After the mobile device 652 logs in to the wireless network, the control passes to block 810, where the process 800 displays an option to configure security settings to the oncologist at the user interface. Control passes to block 812, where the process 800 proceeds to block 814 if the oncologist selects the option to configure security settings (i.e., the "YES" at block 812). If the oncologist does not select the option to configure security settings (i.e., the "NO" at block 812), control passes to block 816. At block 814, the process 800 can configure the security setting of the mobile device 652 and/or the collaboration device 20. For example, the process 800 can set an authentication preference for the oncologist (e.g., a fingerprint preference, a face identification preference, or a typed password preference).

Flow then passes to block 816, where the process 800 can display an option to open an instructional module to the oncologist at the user interface. Control then passes to block 818, where if the oncologist selects the option to open the instructional module, the process 800 can proceed to block 820. If the oncologist does not select the option to open the instructional module, the process 800 can proceed to block 822. At block 820, the process 800 can display an instructional manual (i.e., a user manual) to the oncologist. Control then passes to block 822, where the process 800 can display a FAQ menu as well as a suggested pathways tutorial option to the oncologist at the user interface. Control then passes to block 824, where if the oncologist selects the suggested pathways tutorial option, control passes to block 826. If the oncologist does not select the suggested pathways tutorial option, the process 800 ends.

At block 826, the process 800 can run at least one tutorial that can include tutorials about how to use the collaboration device 20 (e.g., how to change the volume of the collaboration device 20) as well as suggest "first questions" the oncologist may want to ask the collaboration device. In particular, tutorials related to suggested questions may instruct the oncologist on methods for querying the collaboration device. After the oncologist practices with a number of questions, the collaboration device 20 can exit the tutorial and allow the oncologist to ask questions independently. The tutorials can be generated by recognizing the types of intents that the specific physician may have and anticipating the questions based on various criteria (e.g., institution, areas of specialty, questions asked by other physicians that they are affiliated with, the patients' molecular/clinical data and their past order history, upcoming patients based on EMR scheduling integration, etc.). The tutorial can instruct the user visually and/or audibly about basic voice commands the collaboration device can recognize such as "Volume Up," "Volume Down," "Start Pairing," "Turn Off," or other suitable voice commands.

Figure 32:
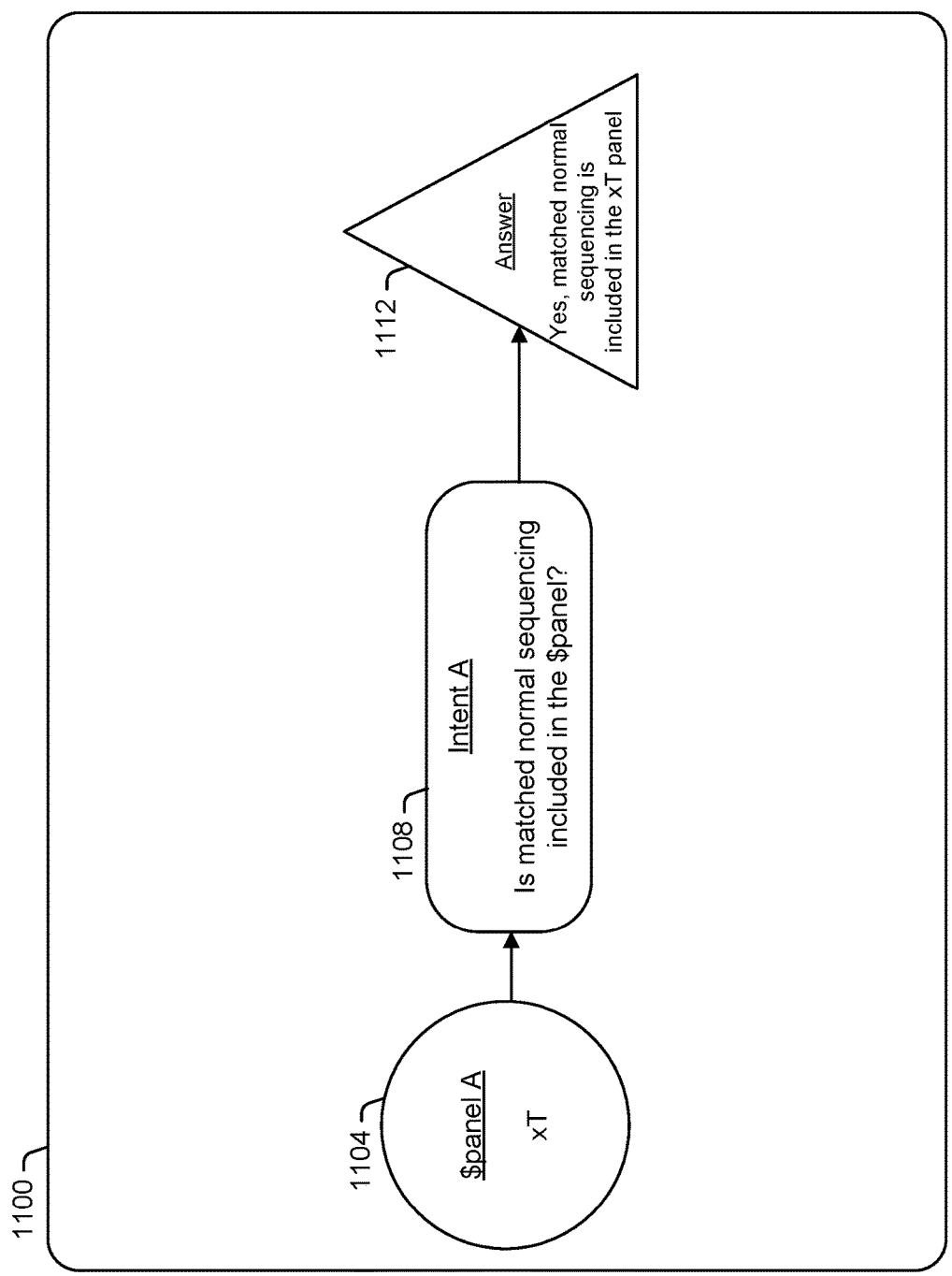
FIG. 32 is a screen shot for use by a system administrator for visually specifying system intents, intent parameters and answer formats for provider panel types that is consistent with at least some aspects of the present disclosure.

Referring now to FIG. 32, a screen shot 1100 of an interface for use by a system administrator for visually specifying system intents, intent parameters and answer formats for provider panel types that is consistent with at least some aspects of the present disclosure is shown. As shown, a panel variable module 1104, an intent module 1108, and an answer module 1112 can be used by a user to specify intents. It is noted that the modules can appear differently to make identification easier. For example, the modules 1104-1112 can be different shapes. The intent module can have an intent (i.e., "Intent A") that may require a variable input to answer. In this example, the variable is a panel type. The panel variable module 1104, which corresponds to a type of panel, can be linked to the intent module 1108, which can also be linked to the answer module 1112 which can automatically fill in the answer based on the panel variable module 1104. The user can drag and link the modules 1104-1112 using a mouse or touchscreen to create the intent and associated answer.

Figure 33:
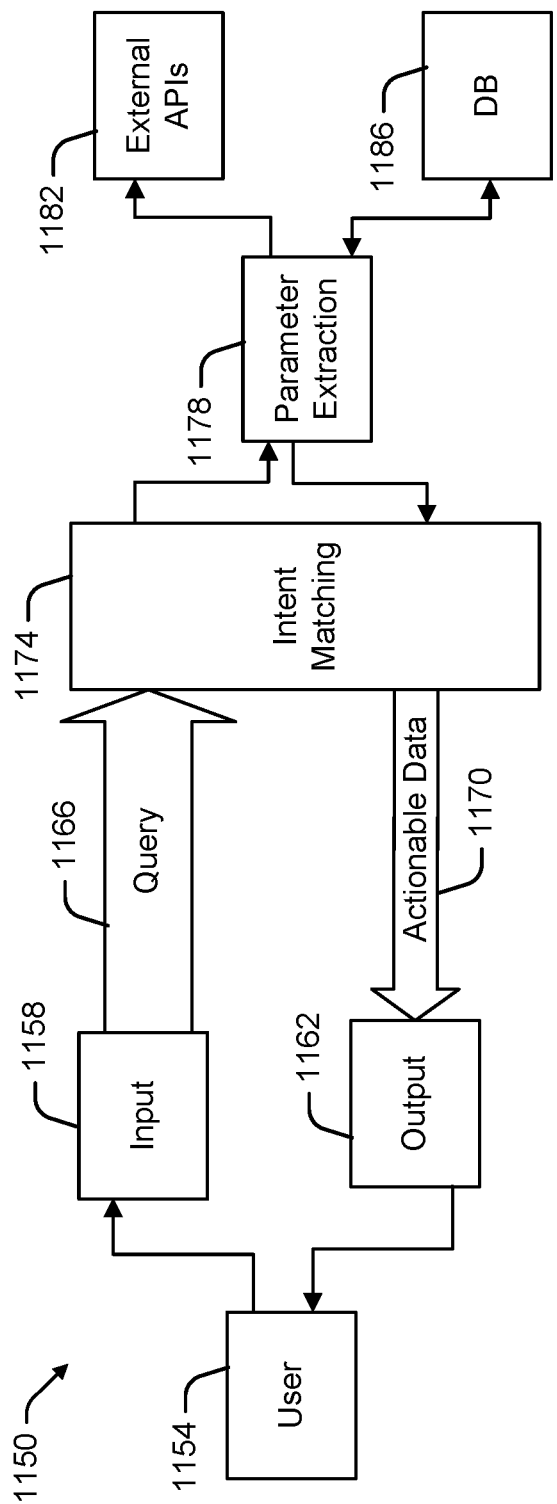
FIG. 33 is a schematic diagram of an intent extraction architecture.

Referring now to FIG. 1 well as FIG. 33, an intent extraction architecture 1150 that is consistent with at least some aspects of the present disclosure is shown. The intent extraction architecture 1150 can include an input module 1158 including a microphone and an output module 1162 including a speaker that may be included in the collaboration device 20. A user 1154 can provide audible queries to the input module 1158 and receive audible answers from the output module 1162. The input module 1158 can process the audible query (e.g., perform text recognition) and transmit a query 1166 to an intent matching module 1174 included in the intent extraction architecture 1150. The intent matching module 1174 can include an intent matching application such as Dialogflow. The intent matching module 1174 can extract the intent from the query and transmit the query 1166 and the intent to a parameter extraction module 1178 included in the intent extraction architecture 1150. The parameter extraction module 1178 can extract any parameters from the query 1166 that are relevant to the intent. The parameter extraction module 1178 can then communicate with an API module 1182 and/or a database 1186 included in the intent extraction architecture 1150 in order to extract information relevant to the extracted parameters and/or intent from the database 1186. The information can be transmitted to the intent matching module 1174. The intent matching module 1174 can generate actionable data 1170 based on the information from the database 1186. The intent matching module 1174 can then transmit the actionable data 1170 to the output module 1162, which can output an audible answer based on the actionable data 1170 to the user 1154.

Figure 34:
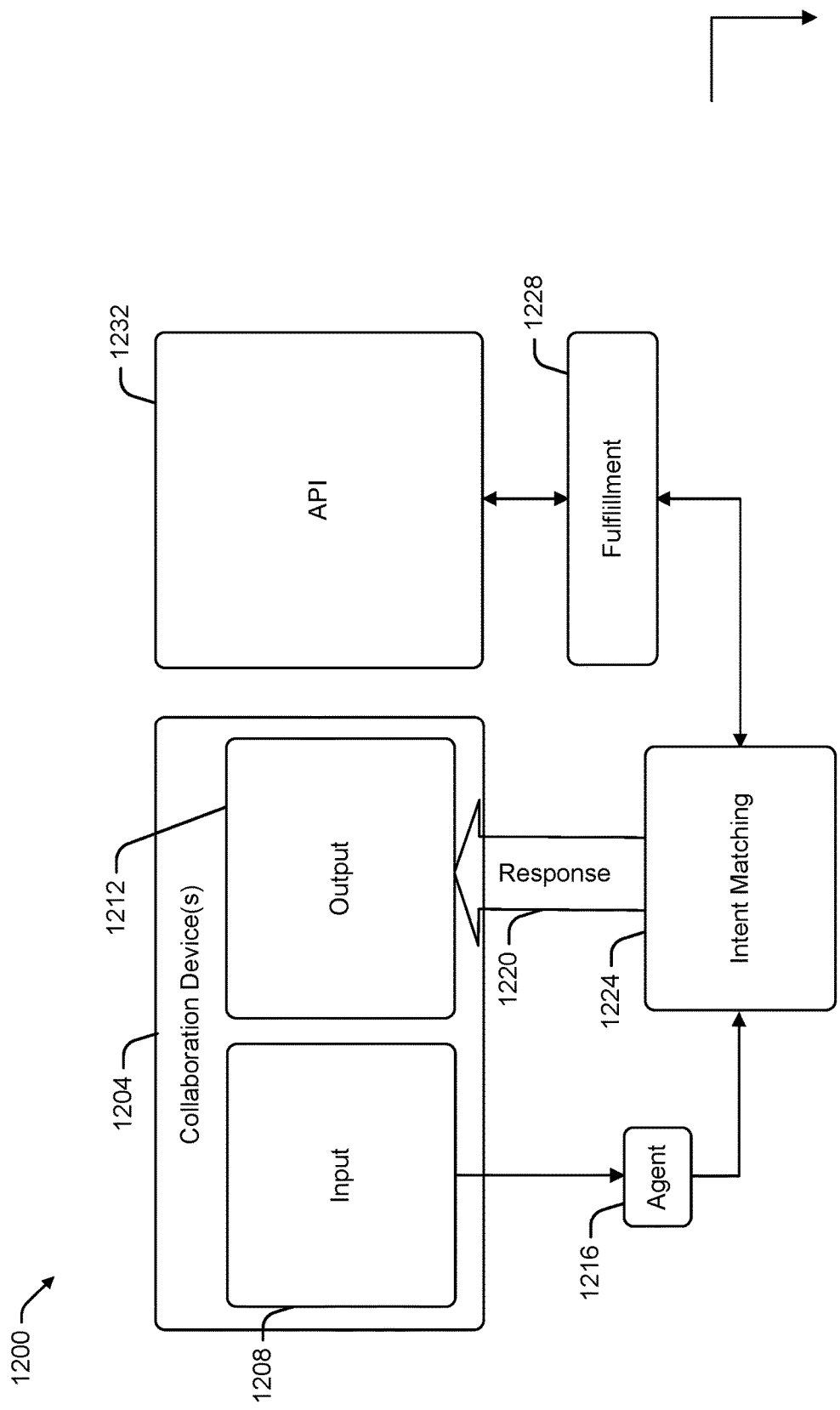
FIG. 34 is a schematic diagram of a question and answer workflow.

Referring now to FIGS. 1, 28, and 33 as well as FIG. 34, an exemplary question and answer workflow 1200 that is consistent with at least some aspects of the present disclosure is shown. The workflow 1200 can include one or more collaboration devices 1204 (e.g., the collaboration device 20 and/or the mobile device 652), each including an input module 1208 and an output module 1212. The input module 1208 may include at least a portion of the components of the input module 1158, and the output module 1212 may include at least a portion of the components of the output module 1162. The input module 1208 can receive audible queries from an oncologist. The audible query can include a single question that may be formulated from a series of prompts displayed on one of the collaboration devices 1204. The input module 1208 can output the audible query (which can include a raw audio file) to an agent module 1216 included in the workflow 1200. The agent module 1216 can include a number of natural language understanding (NLU) modules that translate text or spoken user requests into actions. The agent module 1216 can translate the audible query into an action and transmit the action to an intent matching module 1224 included in the workflow 1200. The intent matching module 1224 may be substantially the same as the intent matching module 1174. The intent matching module 1224 can communicate with a fulfillment module 1228 included in the workflow 1200. The fulfillment module 1228 can include an intent-specific webhook for agent look-up of business logic. The fulfillment module 1228 can receive the intent from the intent matching module 1224 and communicate with an API module 1232 included in the workflow 1200 to extract relevant information from a database linked to the API module 1232. The fulfillment module 1228 can then receive the relevant information from the API module 1232 and transmit the relevant information to the intent matching module 1224. The intent matching module 1224 can then generate a response 1220 based on the relevant information and transmit the response 1220 to the output module 1212. The output module 1212 can then visually and/or audible output the response 1220.

Figure 35:
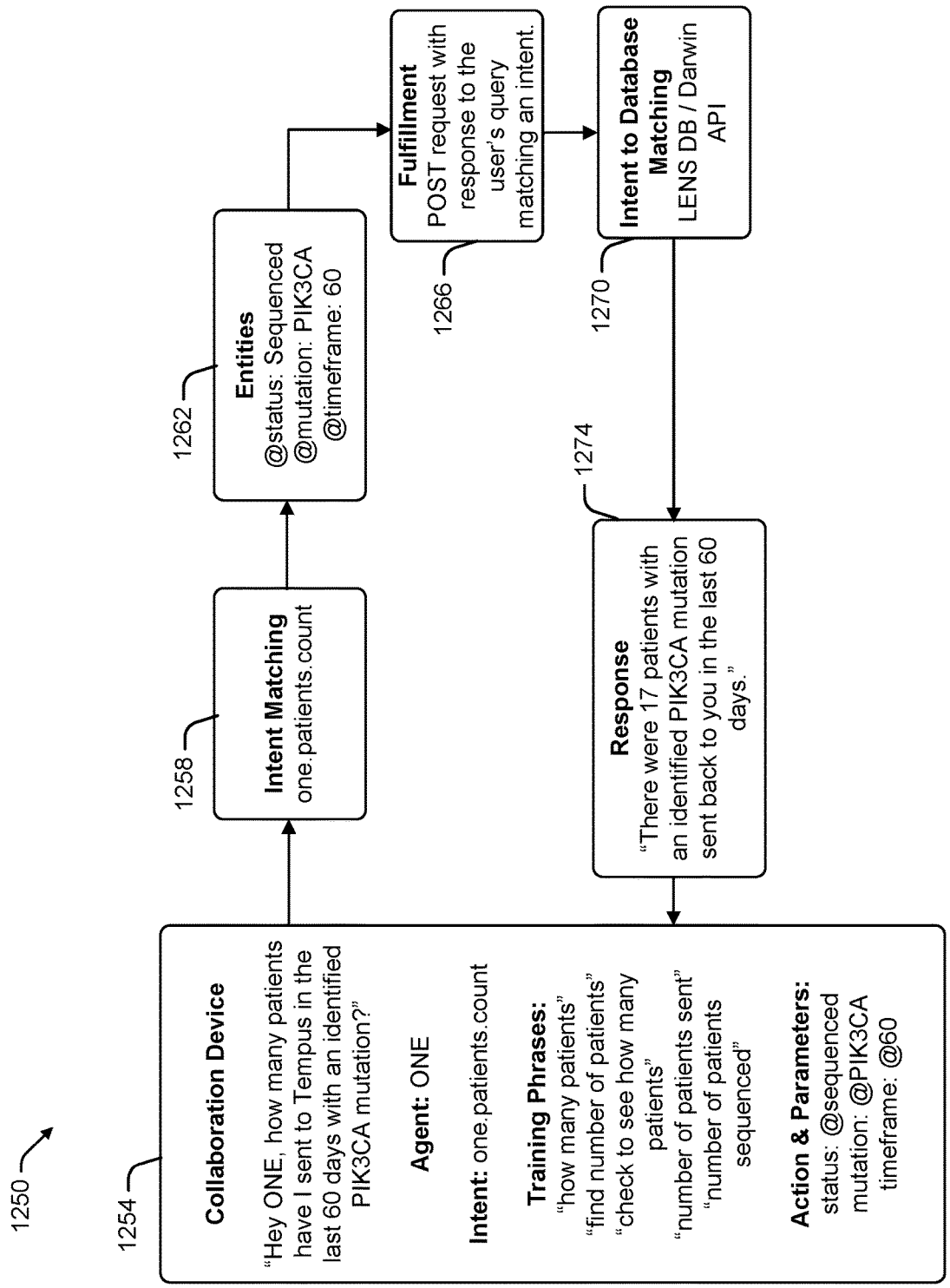
FIG. 35 is a schematic diagram of an exemplary conversation workflow.

Referring now to FIGS. 33 and 34 as well as FIG. 35, an exemplary conversation workflow 1250 that is consistent with at least some aspects of the present disclosure is shown. A collaboration device 1254 (e.g., the collaboration device 20) can receive an audible query. For example, the audible query can be "Hey ONE, how many patients have I sent to Tempus in the last 60 days with an identified PIK3CA mutation?" The collaboration device 1254 can transmit text extracted from the audible query to an intent matching module 1258, which can be substantially the same as the intent matching module 1224. The intent matching module 1258 can extract an intent associated with the audible query from the text. For example, the intent can be "one.patients.count." The intent matching module 1258 can transmit the text associated with the audible query and the intent to an entities module 1262 that may be substantially the same as the parameter extraction module 1178. The entities module 1262 can determine one or more parameters based on the text. For example, the entities module 1262 can determine a status parameter (e.g., @status: Sequenced), a mutation parameter (e.g., @mutation: PIK3CA), and a timeframe parameter (e.g., @timeframe: 60). The entities module 1262 can transmit the parameters, the text, and/or the intent to a fulfillment module 1266 that formulates the parameters as a request to a database that includes that actual values of the parameters. The fulfillment module 1266 transmits the request to an intent to database matching module 1270 that extracts the requested values from a database. The intent to database matching module 1270 can then output the requested values to as response module 1274 that may be included in the intent matching module 1258. The response module 1274 can generate a response and transmit the response to the collaboration device 1254. For example, the response module 1274 can generate and transmit "There were 17 patients with an identified PIK3CA mutation sent back to you in the last 60 days." The collaboration device 1254 can then audibly and/or visually output the response.

The methods and systems described above may be utilized in combination with or as part of a digital and laboratory health care platform that is generally targeted to medical care and research, and in particular, generating a molecular report as part of a targeted medical care precision medicine treatment or research. It should be understood that many uses of the methods and systems described above, in combination with such a platform, are possible. One example of such a platform is described in U.S. patent application Ser. No. 16/657,804, titled "Data Based Cancer Research and Treatment Systems and Methods" (hereinafter "the '804 application"), which is incorporated herein by reference and in its entirety for all purposes.

In some aspects, a physician or other individual may utilize a collaboration device, such as the collaboration device 20 or the mobile device 652, in connection with one or more expert treatment system databases shown in FIG. 1 of the '804 application. The collaboration device may operate on one or more micro-services operating as part of a system services/applications/integration resources database, and the methods described herein may be executed as one or more system orchestration modules/resources, operational applications, or analytical applications. At least some of the methods (e.g., microservices) can be implemented as computer readable instructions that can be executed by one or more computational devices, such as the collaboration device 20, a server such as the first server 756, the second server 766, the third server 776, the fourth server 772, the fifth server 788, the AI server 14, or the collaboration server 12, and/or the administrator device 752. The one or more computational devices can be included in a system described above, such as the fifth system 750.

For example, an implementation of one or more embodiments of the methods and systems as described above may include microservices included in a digital and laboratory health care platform that can audibly broadcast responses to a physician in response to a query about a patient's molecular report.

In some embodiments, a system can include a single microservice for executing and delivering the response to the query or may include a plurality of microservices, each microservice having a particular role which together implement one or more of the embodiments above. In one example, a first microservice can include listening for a query from a microphone of a collaboration device or otherwise receiving the query from the user, identifing an intent associated with the query, and identifying a data operation associated with the identified intent in order to deliver a structured query having a data operation to be performed on the patient's molecular report to a second microservice for processing the query. Similarly, the second microservice may include performing the data operation on the patient's molecular report in order to generate response data, generating an audible response file from the response data, and providing that audible response data to the collaboration so that the collaboration device may provide the audible response to the physician in response to their query according to an embodiment, above.

The collaboration device may be utilized as a source for automated entry of the kind identified in FIG. 59 of the '804 application. For example, the collaboration device may interact with an order intake server to generate an order for a test. Where embodiments above are executed in one or more micro-services with or as part of a digital and laboratory health care platform, one or more of such microservices may be part of an order management system that orchestrates the sequence of events as needed at the appropriate time and in the appropriate order necessary to instantiate embodiments above.

For example, continuing with the above first and second microservices, an order management system may notify the first microservice that an order for an audible query has been received and is ready for processing. The first microservice may include executing and notifying the order management system once the delivery of a structured query is ready for the second microservice. Furthermore, the order management system may identify that execution parameters (prerequisites) for the second microservice are satisfied, including that the first microservice has completed, and notify the second microservice that it may continue processing the order to provide the audible response to the collaboration device according to an embodiment, above. While two microservices are utilized for illustrative purposes, query identification, intent identification, data operation association and executions, and audible response generation and delivery may be split up between any number of microservices for audibly broadcasting responses to user based queries in accordance with performing embodiments herein.

In another example, the microservices included in a digital and laboratory health care platform and capable of supporting audibly broadcasting responses to a physician in response to a query about a status of a patient's molecular report can include identifying a status of the progress of the generation of the patients report. The platform can send a query to an order management system to request a current status of the order for a respective patient. The other management system may identify the last completed microservice which has broadcast a completion message and return the current stage of the patient's order and/or a time remaining until a report may be generated. The collaboration device may broadcast the current status as received from the order management system.

In some aspects, a physician or other individual may utilize a collaboration device in connection with one or more electronic document abstraction services shown in FIG. 80 of the '804 application. In some embodiments, the collaboration device can receive a verbal request to summarize a portion or the whole of an electronic document. The electronic document may be identified and provided to an abstraction microservice for consumption for generating a structured data format of the information contained in the electronic document. The abstraction microservice, or a subsequent microservice, may include identifying which information of the information contained in the electronic document contains medically important data and generating an audible response to the user's query to summarize the document. In an example, a summary of a genetic sequencing report may identify the somatic variants of the patient, the matched therapies which may be prescribed to the patient, and potential clinical trials mentioned in the report. In another example, a summary of a patient's clinical history may be generated from the electronic health records and/or progress notes available to the microservices platform. A system (e.g., the fifth system 750) can generate an audible response to describe the patient's treatment history, family history, or other important medical information contained in the medical record for playback to the physician.

In some aspects, a physician or other individual may utilize a collaboration device (e.g., the collaboration device 20 or the mobile device 652) in connection with one or more electronic document abstraction services shown in FIGS. 158-160 of the '804 application. The collaboration device may receive a verbal request to summarize a portion or the whole of a physical document. The collaboration device may request the physician to open a corresponding application on their mobile device to capture the physical document in an electronic format, converting the physical document to an electronic document. The electronic document may then be provided to an abstraction microservice for consumption for generating a structured data format of the information contained in the electronic document. Summarization and audible response generation may be performed as described above with respect to another aspect.

In some aspects, a physician or other individual may utilize a collaboration device (e.g., the collaboration device 20 or the mobile device 652) in connection with one or more prediction engine services shown in FIG. 204 of the '804 application. The collaboration device may receive a verbal request to predict an outcome for a patient with respect to a specific target outcome and within a specified time period. A query identifying the patient, the outcome, and the time period may be sent to a prediction engine to generate a prediction. In another embodiment, predictions may be precomputed and stored in a patient prediction database for retrieval. An audible query response including the prediction may be generated provided to the collaboration device for playback to the physician. Queryable predictions may include targets such as odds of progression-free survival, death, metastasis, occurrence of disease progression states, or other predictable outcomes and time periods measured in days, weeks, months, or years.

In another aspect, a pathologist or other individual may utilize a collaboration device (e.g., the collaboration device 20 or the mobile device 652) in connection with one or more cell-type profiling services shown in FIG. 244 of the '804 application. The collaboration device may receive a verbal request to identify cell and tissue types present in an H&E or IHC slide from a tumor next-generation sequencing report generated from the slide or a slide proximate to the sequenced slide. A cell-type profiling service may identify the cell-types present in the slide and generate an audible query response to provide the identified cell-types to the pathologist. In another aspect, the collaboration device may receive a verbal request to identify an unknown tumor origin of a tumor tissue present in a slide. The cell-type profiling service may identify the tumorous cell-types present in the slide as originating from an organ of the body and identify that the cell-types likely represent a metastasis from an organ to the site where the tumor tissue was biopsied. Consistent with the above aspects, an audible query response may be generated to provide the origin of the identified tumorous cell-types to the physician.

In some aspects, a physician or other individual may utilize a collaboration device (e.g., the collaboration device 20 or the mobile device 652) in connection with one or more tissue segmentation services shown in FIGS. 253 and 261 of the '804 application. The collaboration device may receive a verbal request to summarize classification of a portion or the whole of a digital representation of an H&E or IHC slide. The digital slide may be identified and provided to a tissue segmentation microservice for consumption, classification of the tissue present, and summarization. The segmentation microservice, or a subsequent microservice, may include identifying the cell/tissue types and proportions present in the digital slide and generating an audible response to the user's query to summarize the types and respective proportions to the physician.

The digital and laboratory health care platform further includes one or more insight engines shown in FIG. 272. Exemplary insight engines may include a tumor of unknown origin engine, a human leukocyte antigen (HLA) loss of homozygosity (LOH) engine, a tumor mutational burden (TMB) engine, a PD-L1 status engine, a homologous recombination deficiency (HRD) engine, a cellular pathway activation report engine, an immune infiltration engine, a microsatellite instability engine, a pathogen infection status engine, and so forth as described with respect to FIGS. 189, 199-200, and 266-270 of the '804 application. In an aspect, a physician may query the collaboration device as to the patient's status for any diagnosis of the patient as to an insight engine such as HLA LOH, TMB, PD-L1, HRD, active pathway, or other insight status. The collaboration device may identify an insight engine query by keyword content matching one of the existing insight engines and generate a corresponding database query to retrieve the related status associated with the patient. The related status of the patient may then be provided as part of an audible response to the physician by the collaboration device. In some examples, an audible response may identify the source diagnostic testing which provided the baseline for the insight as well as the date of collection. For example, an audible response may include, "Patient has been identified as TMB High as a result of next generation sequencing of the patient's breast tumor on Jan. 21, 2019."

When the digital and laboratory health care platform further includes a molecular report generation engine, the methods and systems described above may be utilized to create a summary report of a patient's genetic profile and the results of one or more insight engines for presentation to a physician. For instance, the report may provide to the physician information about the extent to which the specimen that was sequenced contained tumor or normal tissue from a first organ, a second organ, a third organ, and so forth. For example, the report may provide a genetic profile for each of the tissue types, tumors, or organs in the specimen. The genetic profile may represent genetic sequences present in the tissue type, tumor, or organ and may include variants, expression levels, information about gene products, or other information that could be derived from genetic analysis of a tissue, tumor, or organ via a genetic analyzer. The report may further include therapies and/or clinical trials matched based on a portion or all of the genetic profile or insight engine findings and summaries shown in FIGS. 271 and 302 of the '804 application. A physician, or other individual, may query the collaborative device as to the therapies or clinical trials the patient may qualify for. In one example, the collaboration device may reference a database having previously stored the patient's potential therapies and clinical trials. In another example, the collaboration device may initiate a new identification of potential therapies and/or clinical trials based upon the query received. A microservice may include determining the patient's eligibility based on all current patient information, identifying the closest matches, and generating, or causing another microservice to generate, an audible response with the closest matching therapies or clinical trials. The collaboration device may receive and broadcast the audible response to the physician.

It should be understood that the examples given above are illustrative and do not limit the uses of the systems and methods described herein in combination with a digital and laboratory health care platform.

Figure 36:
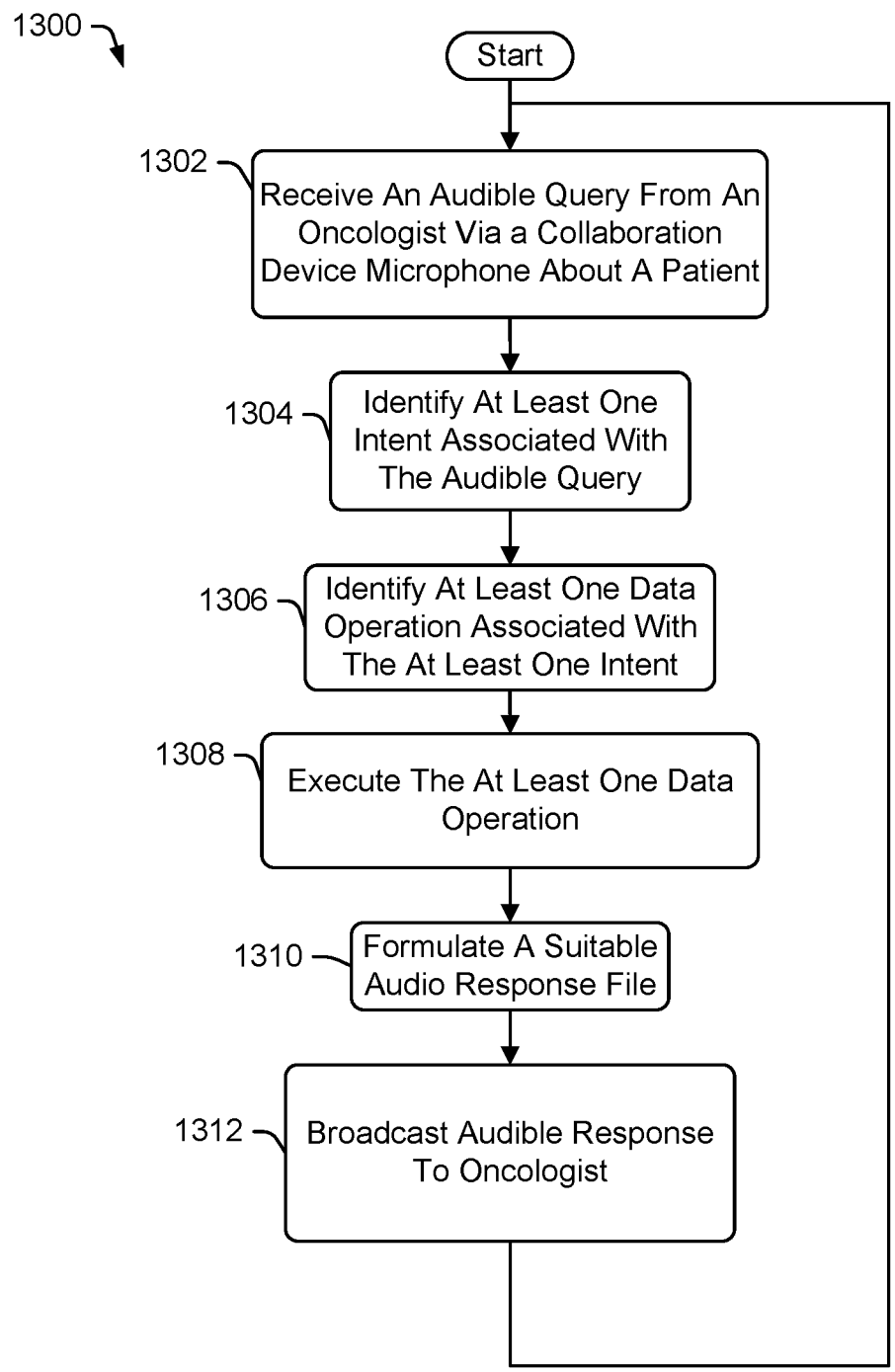
FIG. 36 is a flowchart of a process that provides an audible response to an oncologist using at least one microservice and/or engine that is consistent with at least some aspects of the present disclosure.

Referring now to FIG. 36, a process 1300 that is consistent with at least some aspects of the present disclosure is shown that provides an audible response to an oncologist using at least one microservice and/or engine is shown. The process 1300 can be executed (i.e., performed) in conjunction with (e.g., in parallel with) the process 450 in order to provide relevant information to the oncologist based on audible queries enunciated by the oncologist. Furthermore, the process 1300 can utilized in combination with or as part of a digital and laboratory health care platform, such as the platform is described in the '804 application. The digital and laboratory health care platform can include one or more microservices and/or may operate on one or more microservices. In other words, the digital and laboratory health care platform may be implemented using microprocesses. In some embodiments, the digital and laboratory health care platform can generate a molecular report as part of a targeted medical care precision medicine treatment.

At process block 1302, the process 1300 can receive an audible query from an oncologist via a collaboration device microphone. In some embodiments, the collaboration device can include the collaboration device 20. In some embodiments, the collaboration device can include the mobile device 652. In some aspects, the audible query can be a verbal request to summarize a portion or the whole of an electronic document related to the patient (e.g., "Summarize the first page of the molecular report for Dwayne Holder"), a verbal request about the status of the patient's molecular report, a verbal request to predict an outcome for a patient with respect to a specific target outcome and within a specified time period (e.g., "Predict one year survival for Dwayne Holder"), a verbal request to identify cell and tissue types present in an H&E or IHC slide from a tumor next-generation sequencing report generated from the slide or a slide proximate to the sequenced slide, a verbal request to summarize a classification of a portion or the whole of a digital representation of an H&E or IHC slide, or another suitable verbal request.

At block 1304 the process 1300 can identify at least one intent associated with the audible query. For example, if the audible query is "Summarize the first page of the molecular report for Dwayne Holder," the intent may be "Summarize a portion of this document" and specific query parameters may include "first page" and "molecular report for Dwayne Holder" where the underlined portion and document in the general query are populated with "first page" and "molecular report for Dwayne Holder" to generate a specific query intent. As another example, if the audible query is "What is the estimated one year survival for Dwayne Holder?" the intent may be "Estimate probability of outcome in time period for patient" and specific query parameters may include "survival," "one year," and "Dwayne Holder" for the underlined outcome, time period, and patient respectively.

At block 1306 the process 1300 can identify at least one data operation associated with the specific intent. The at least one data operation can include providing the at least one intent to at least one microservice and/or engine. For example, if the intent is "Summarize a portion of this document," the process 1300 can provide the portion and document parameters to an abstraction microservice. As another example, if the intent is "Estimate probability of outcome in time period for patient," the process 1300 can provide the outcome, time period, and patient parameters to a prediction engine. Thus, the process 1300 can be performed in conjunction with one or more microservices. In some embodiments, the process 1300 can be performed in conjunction with one or more microservices of an order management system. In these embodiments, the process 1300 can access or report on a status of an order as is flows through various databases and/or servers. In some embodiments, the process 1300 can be performed in conjunction with one or more microservices of a medical document abstraction system. In these embodiments, the process 1300 can access or report on contents of physical or electronic medical documents. In some embodiments, the process 1300 can be performed in conjunction with one or more microservices of a mobile device application. In these embodiments, the process 1300 can access or report on the status of a patient, physical or electronic documents, or other application interfaced data. In some embodiments, the process 1300 can be performed in conjunction with one or more microservices of a prediction engine. In these embodiments, the process 1300 can access precomputed predictions of a patient or request on demand predictions to be generated regarding the status of a patient. In some embodiments, the process 1300 can be performed in conjunction with one or more microservices of a service such as a cell-type profiling service. In these embodiments, the process 1300 can access precomputed cell-type predictions from sequencing or trigger computation on a given raw sequencing data or digital image. In some embodiments, the process 1300 can be performed in conjunction with a variant calling engine to provide information to a query involving variants. In these embodiments, the process 1300 can access a database (e.g., a Tempus database) to provide sequencing results. In some embodiments, the process 1300 can be performed in conjunction with an insight engine. In these embodiments, the process 1300 can access a database (e.g., a Tempus database) to provide advanced analytic results for a particular insight test [TUO, HLA LOH, TMB, PD-L1, HRD, active pathway, or other insight status]). In some embodiments, the process 1300 can be performed in conjunction with a therapy matching engine. In these embodiments, the process 1300 can access therapies which are relevant to the patient. In some embodiments, the process 1300 can be performed in conjunction with a clinical trial matching engine. In these embodiments, the process 1300 can access clinical trials which are relevant to the patient.

At block 1308, the process 1300 can execute the at least one data operation using at least one microservice and/or at least one engine. The at least one microservice and/or at least one engine can generate response data based on the parameters identified at block 1304.

At block 1310, the process 1300 can formulate a suitable audio response file based on the response data received from the at least one microservice and/or the at least one engine. For example, the abstraction microservice can identify which information of the information contained in the electronic document contains medically important data, and include the medically important data in the response data provided to the process 1300. The process 1300 can then include at least a portion of the medically important data in the audio response file. As another example, the prediction engine can generate an estimated survival figure (e.g., a percentage), and include the estimated survival figure in the response data provided to the process 1300.

At block 1312, the process 1300 can broadcast an audible response to the oncologist. More specifically, the process 1300 can cause the audible response to be output at speakers included in the collaboration device. The audible response can be the result of the collaboration device actuating the speakers based on the audio response file.

Appendix D includes an exemplary set of questions and answers that an oncologist may voice to a disclosed collaboration device and that the device may return in response. While clearly not exhaustive, the exemplary questions and answers give a sense of the power of the system and the complexity of the types of queries that the system can handle.

Table 2 below includes an exemplary set of questions and answers that an oncologist may voice to a disclosed collaboration device and that the device may return in response. While clearly not exhaustive, the exemplary questions and answers give a sense of the power of the system and the complexity of the types of queries that the system can handle.

TABLE 2

| Category | Question | Answer | Answer for negative | Answer for Null |
|---|---|---|---|---|
| Report Content | Where was Dwayne Holder's tumor sample collected from? | Dwayne Holder's tumor sample was collected from a lung biopsy. | Tempus does not have information on where Dwayne Holder's tumor sample was collected from. | Please check the Tempus portal for information about Dwayne Holder's tumor sample. |
| Report Content | What is the tumor percentage of Dwayne Holder's tumor sample submitted to Tempus for sequencing? | The tumor percentage of Dwayne Holder's sample was 40%. | Tempus does not currently have information on Dwayne Holder's tumor percentage. | Please check the Tempus portal for information about Dwayne Holder's tumor percentage. |
| Report Content | What is Dwayne Holder's diagnosis? | Dwayne Holder has a Pancreatic Ductal Adenocarcinoma. | Tempus does not currently have information on Dwayne Holder's diagnosis. | Please check the Tempus portal for information about Dwayne Holder's diagnosis. |
| Report Content | What is Dwayne Holder's Date Of Birth? | Dwayne Holder's date of birth is Aug. 8th, 1971. | Tempus does not currently have information on Dwayne Holder's date of birth. | Please check the Tempus portal for information on Dwayne Holder's date of birth. |

TABLE 2-continued

| Category | Question | Answer | Answer for negative | Answer for Null |
|---|---|---|---|---|
| Report Content | What is Dwayne Holder's TMB? | Dwayne Holder's TMB was found to be in the 79th percentile. | Dwayne Holder's Tempus xT report did not have a TMB associated with it. | Please check the Tempus portal for information on Dwayne Holder's TMB. |
| Report Content | What genes does Dwayne Holder have a germline mutation in? | Dwayne Holder was found to have a germline mutation in his BRCA2 gene during sequencing. | Tempus did not find any germline mutations for Dwayne Holder during sequencing. | Tempus did not receive a normal sample for Dwayne Holder, therefore no germline mutations were found. |
| Report Content | How many fusions does Dwayne Holder have? | Dwayne Holder was found to have 1 clinically validated fusion. | Dwayne Holder did not have any fusions found during sequencing. | Please check the Tempus portal for information on Dwayne Holder's mutations. |
| Report Content | Has Dwayne Holder received any previous lines of therapy? | Dwayne Holder has previously received folfirinox and olaparib. | Tempus does not currently have any information about any previous therapies for Dwayne Holder. | Please check the Tempus portal for information on Dwayne Holder's previous lines of therapy. |
| Report Content | What report edition is Dwayne Holder's report? | Dwayne Holder has the original report edition. | Please check the Tempus portal for information on Dwayne Holder's report edition | Please check the Tempus portal for information on Dwayne Holder's report edition |
| Report Content | What was Dwayne Holder's date of diagnosis? | Dwayne Holder's diagnosis date is Jul. 27th, 2018. | Tempus does not have information on Dwayne Holder's date of diagnosis. | Please check the Tempus portal for information on Dwayne Holder's diagnosis date. |
| Report Content | Have there been any amendments to Dwayne Holder's report? | Yes, there has been an amendment to Dwayne Holder's report. | No, there has not been an amendment to Dwayne Holder's report. | Please check the Tempus portal for information on Dwayne Holder's reports, including any amendments made. |
| Report Content | Is Dwayne Holder MSI high? | Yes, Dwayne Holder is MSI high. | Dwayne Holder is MSI stable. | Please check the Tempus portal for information on Dwayne Holder's MSI status. |
| Report Content | What is Dwayne Holder's mutations per Megabase? | Dwayne Holder was found to have 2.7 mutations per Megabase during sequencing. | Dwayne Holder does not have any information associated with TMB on his report. | Please check the Tempus portal for information on Dwayne Holder's TMB. |
| Report Content | What FDA approved, on label drugs does Tempus recommend for Dwayne Holder? | Tempus does not recommend drugs or other therapies. Selection of therapies should be performed through the physician's judgment. | Tempus does not recommend drugs or other therapies. Selection of therapies should be used by the physician's judgment. | Tempus does not recommend drugs or other therapies. Selection of therapies should be performed through the physician's judgment. |
| Report Content | What drugs have been approved by the FDA for patients who have mutations like Dwyane Holder? | Keytruda has been approved by the FDA for patients who are MSI high and meet the other labeling criteria. | Tempus does not have any FDA approved drugs associated with patients that have mutations like Dwayne Holder's. | Please check the Tempus portal for more information on Dwayne Holder's staging information. |
| Report Content | What FDA approved, off label drugs does Tempus recommend for Dwayne Holder? | Tempus does not recommend drugs or other therapies. Selection of therapies should be used by the physician's judgment (see disclaimer text) | Tempus does not recommend drugs or other therapies. Selection of therapies should be performed through the physician's judgment. | Tempus does not recommend drugs or other therapies. Selection of therapies should be performed through the physician's judgment. |
| Report Content | What FDA approved therapies for other indications exist for Dwayne Holder? | Based on Dwayne Holder's mutations, olaparib, niraparib, rucaparib, talazoparib, and palbociclib are FDA approved therapies for other indications. | Tempus does not have any FDA approved drugs associated with patients that have mutations like Dwayne Holder's. | Please check the Tempus portal for more information on Dwayne Holder's staging information. |

TABLE 2-continued

| Category | Question | Answer | Answer for negative | Answer for Null |
|---|---|---|---|---|
| Report Content | What investigational drugs does Tempus recommend for Dwayne Holder? | Tempus does not recommend drugs or other therapies. Selection of therapies should be used by the physician's judgment (see disclaimer text) | Tempus does not recommend drugs or other therapies. Selection of therapies should be performed through the physician's judgment. | Tempus does not recommend drugs or other therapies. Selection of therapies should be performed through the physician's judgment. |
| Report Content | What investigational drugs are associated with patients like Dwayne Holder? | A preclinical study found Verteporfin and LY-3009120, an investigational drug regimen, to have a good response in KRAS G.12V mutations. | There is not much research currently surrounding investigational drugs associated with patients that have mutations like Dwayne Holder's. | Please check the Tempus portal for more information on Dwayne Holder's staging information. |
| Report Content | What AJCC staging does Dwayne Holder have? | Dwayne Holder has a stage T3 N1 M1 tumor. | Tempus does not have information about Dwayne Holder's AJCC staging. | Please check the Tempus portal for more information on Dwayne Holder's staging information. |
| Report Content | How many mutations did Tempus find for Dwayne Holder? | Dwayne Holder was found to have 5 mutations during sequencing. | Tempus did not find any mutations for Dwayne Holder during sequencing. | Please check the Tempus portal for more information on Dwayne Holder's mutations. |
| Report Content | What somatic mutations does Dwayne Holder have? | Dwayne Holder was found to have a CDKN2A, KRAS, and a BRCA2 somatic mutation during sequencing. | Tempus did not find any somatic mutations for Dwayne Holder during sequencing. | Please check the Tempus portal for more information on Dwayne Holder's mutations. |
| Report Content | What can I give Dwayne Holder for his KRAS mutation? | Verteporfin may be a treatment option given Dwayne Holder's KRAS mutation. Refer to the complete report for additional details. | Tempus finds that Dwayne Holder's KRAS mutation is somatic and biologically relevant, though there are no therapies currently associated with this specific mutation. | Please check the Tempus portal for more information on Dwayne Holder's mutations. |
| Report Content | Has Dwayne Holder had any biopsies? | Dwayne Holder has had a lung biopsy. | Tempus does not have a record of any previous biopsies for Dwayne Holder, though this information may not have been shared with Tempus. | Please check the Tempus portal for more information on Dwayne Holder's clinical history. |
| Report Content | When was Dwayne Holder's lung biopsy? | Dwayne Holder's biopsy was performed on Feb. 28th, 2019. | Tempus does not have a record of any previous biopsies for Dwayne Holder, though this information may not have been shared with Tempus. | Please check the Tempus portal for more information on Dwayne Holder's clinical history. |
| Report Content | Has Dwayne Holder taken a PARP inhibitor before? | Dwayne Holder has previously taken a PARP inhibitor. | Dwayne Holder has never received a PARP inhibitor, though this information may not have been shared with Tempus. | Please check the Tempus portal for more information on Dwayne Holder's clinical history. |
| Report Content | What drug classes does Tempus associate with Dwayne Holder's mutations? | Based on Dwayne Holder's mutations, an EGFR Inhibitor, Pyrimidine Analog, PARP Inhibitor, CDK4/6 inhibitor, YAP Inhibitor, or a Pan-RAF Inhibitor are drug classes that are | Tempus does not currently have any associated therapies for Dwayne Holder's mutations. | Please check the Tempus portal for more information on Dwayne Holder's mutations and associated therapies. |

TABLE 2-continued

| Category | Question | Answer | Answer for negative | Answer for Null |
|---|---|---|---|---|
| Report Content | What drug classes does Tempus recommend for patients with mutations like Dwayne Holder? | investigational or FDA approved for other indications. Tempus does not recommend drugs or other therapies. Selection of therapies should be used by the physician's judgment (see disclaimer text) | Tempus does not recommend drugs or other therapies. Selection of therapies should be used by the physician's judgment (see disclaimer text) | Tempus does not recommend drugs or other therapies. Selection of therapies should be used by the physician's judgment (see disclaimer text) |
| Report Content | What FDA approved drugs does Tempus recommend for Dwayne Holder? | Tempus does not recommend drugs or other therapies. Selection of therapies should be used by the physician's judgment (see disclaimer text) | Tempus does not recommend drugs or other therapies. Selection of therapies should be used by the physician's judgment (see disclaimer text) | Tempus does not recommend drugs or other therapies. Selection of therapies should be used by the physician's judgment (see disclaimer text) |
| Report Content | What FDA approved drugs does Tempus associate with patients who have mutations like Dwayne Holder? | Based on Dwayne Holder's mutations, olaparib, rucaparib, niraparib, talazoparib, and palbociclib are FDA approved therapies. | There currently are no FDA approved drugs associated with Dwayne Holder's mutations, though there may be investigational drugs. | Please check the Tempus portal for more information on Dwayne Holder's mutations and associated therapies. |
| Report Content | Has Dwayne Holder taken olaparib before? | Dwayne Holder has taken olaparib before. | Dwayne Holder has never received olaparib, though this information may not have been shared with Tempus. | Please check the Tempus portal for more information on Dwayne Holder's clinical history. |
| Report Content | Is gemcitabine with erlotinib an option for Dwayne Holder? | Dwayne Holder has an X mutation, which was associated with a positive response to gemcitabine and erlotinib in a preclinical trial. | Gemcitabine with erlotinib is associated with a resistance in patients with KRAS mutations like Dwayne Holder. | Please check the Tempus portal for more information on Dwayne Holder's mutations and associated therapies. |
| Report Content | What drugs does Tempus recommend to treat Dwayne Holder? | Tempus does not recommend drugs or other therapies. Selection of therapies should be used by the physician's judgment (see disclaimer text) | Tempus does not recommend drugs or other therapies. Selection of therapies should be used by the physician's judgment (see disclaimer text) | Tempus does not recommend drugs or other therapies. Selection of therapies should be used by the physician's judgment (see disclaimer text) |
| Report Content | What drugs does Tempus associate with patients who have mutations like Dwayne Holder's? | Based on Dwayne Holder's mutations, olaparib, rucaparib, niraparib, talapozib, palbociclib, verteporfin, and LY3009120 are drugs that are investigational or FDA approved for other indications. | Tempus does not recommend drugs or other therapies. Selection of therapies should be used by the physician's judgment (see disclaimer text) | Please check the Tempus portal for more information on Dwayne Holder's mutations and associated therapies. |
| Report Content | Is erlotinib with gemcitabine FDA approved? | Erlotinib and gemcitabine is an FDA approved regimen in some instances. | Erlotinib and gemcitabine is not currently an FDA approved regimen. | Please check the Tempus portal for more information on Dwayne Holder's mutations and associated therapies. |
| Report Content | Is the erlotinib with gemcitabine therapy on Dwayne Holder's report an on-label use | Erlotinib with gemcitabine is an FDA approved regimen in some instances, though given Dwayne Holder's KRAS | Erlotinib and gemcitabine is not currently an FDA approved regimen. | Please check the Tempus portal for more information on Dwayne Holder's mutations and associated therapies. |

TABLE 2-continued

| Category | Question | Answer | Answer for negative | Answer for Null |
|---|---|---|---|---|
| | of the drugs? | mutation, he may be resistance to this therapy. | | |
| Report Content | What type of mutation is Dwayne Holder's KRAS mutation? | Dwayne Holder has a gain of function KRAS mutation. | Dwayne Holder was not found to have a KRAS mutation. | Please check the Tempus portal for more information on Dwayne Holder's mutations and associated therapies. |
| Report Content | What genes does Dwayne Holder have a germline mutation in? | Dwayne Holder has a BRCA2 germline mutation. | Dwayne Holder was not found to have any germline mutations. | Please check the Tempus portal for more information on Dwayne Holder's mutations. |
| Report Content | What grade is Dwayne Holder's tumor? | Dwayne Holder has a grade 3 tumor. | Tempus does not have information about Dwayne Holder's histologic grade. | Please check the Tempus portal for more information on Dwayne Holder's histologic grade. |
| Report Content | What stage is Dwayne Holder? | Dwayne Holder is stage 4. | Tempus does not have information about Dwayne Holder's stage. | Please check the Tempus portal for more information on Dwayne Holder's stage. |
| Report Content | Did Dwayne Holder progress on any of his previous therapies? | According to the clinical records provided to Tempus, Dwayne Holder progressed while on folfirinox. | Tempus does not have a record of any progressions for Dwayne Holder in his clinical history, though this information may not have been shared with Tempus. | Please check the Tempus portal for more information on Dwayne Holder's clinical history. |
| Report Content | Did Dwayne Holder have a response to Olaparib? | According to the clinical records provided to Tempus, Dwayne Holder had a partial response to olaparib. | Tempus does not have a record of any responses to olaparib for Dwayne Holder in his clinical history, though this information may not have been shared with Tempus. | Please check the Tempus portal for more information on Dwayne Holder's clinical history. |
| Report Content | What clinical trials on Dwayne Holder's report are related to his MSI status? | The Keytruda clinical trial on Dwayne Holder's report is related to his MSI status. | Tempus did not include any clinical trials on Dwayne Holder's report that are associated with his MSI status, though he does have 6 other trials listed that may be a fit. | Please check the Tempus portal for more information on Dwayne Holder's clinical matched trials. |
| Report Content | What is the clinical significance of Dwayne Holder's germline BRCA2 mutation? | Dwayne Holder's BRCA2 germline mutation is classified as a pathogenic variant. | Dwayne Holder was not found to have a germline BRCA2 mutation. | Please check the Tempus clinical portal for more information on Dwayne Holder's mutations. |
| Report Content | Are there any diseases associated with Dwayne Holder's BRCA2 mutation? | Dwayne Holder's BRCA2 germline mutation is associated with Hereditary breast and ovarian cancer. | Tempus does not have any diseases associated with Dwayne Holder's germline BRCA2 mutation at this time. | Please check the Tempus clinical portal for more information on Dwayne Holder's mutations. |
| Order Status | What is the status of Dwayne Holder's order? | Dwayne Holder's order is currently in progress. | There is no order status associated with Dwayne Holder's order. | Please check the Tempus portal to find more information about Dwayne Holder's order status. |
| Order Status | When was Dwayne Holder's order placed? | Dwayne Holder's order was placed on Jul. 16, 2019. | There is no date associated with Dwayne Holder's order. | Please check the Tempus portal to find more information about Dwayne Holder's order submission date. |

TABLE 2-continued

| Category | Question | Answer | Answer for negative | Answer for Null |
|---|---|---|---|---|
| Order Status | What is the current status of Dwayne Holder's DNA order? | Dwayne Holder's DNA order is currently complete. | The status of Dwayne Holder's DNA order can not be retrieved at this time. | Please check the Tempus portal for information regarding the status of Dwayne Holder's DNA order. |
| Order Status | What is the current status of Dwayne Holder's IHC MMR order? | Dwayne Holder's IHC MMR order is currently delayed. | The status of Dwayne Holder's IHC MMR order can not be retrieved at this time. | Please check the Tempus portal for information regarding the status of Dwayne Holder's IHC MMR order. |
| Order Status | What is the current status of Dwayne Holder's PD-L1 SP142 order? | Dwayne Holder's PD-L1 SP142 order is currently in progress. | The status of Dwayne Holder's PD-L1 SP142 order can not be retrieved at this time. | Please check the Tempus portal for information regarding the status of Dwayne Holder's PD-L1 SP142 order. |
| Order Status | What orders are currently in progress for Dwayne Holder? | There are 2 orders currently in progress for Dwayne Holder. | Dwayne Holder's in progress orders can not be retrieved at this time. | Please check the Tempus portal for information regarding Dwayne Holder's in progress orders. |
| Order Status | What orders are currently delayed for Dwayne Holder? | There are 3 orders currently delayed for Dwayne Holder. | Dwayne Holder's delayed orders can not be retrieved at this time. | Please check the Tempus portal for information regarding Dwayne Holder's delayed orders. |
| Order Status | What orders are currently complete for Dwayne Holder? | There are 2 orders currently complete for Dwayne Holder. | Dwayne Holder's completed orders can not be retrieved at this time. | Please check the Tempus portal for information regarding Dwayne Holder's in progress orders. |
| Order Status | When did Tempus receive Dwayne Holder's tumor sample? | Tempus received Dwayne Holder's tumor sample on Jul. 20th, 2019. | Tempus has not yet received Dwayne Holder's tumor sample. | Please check the Tempus portal for information regarding Dwayne Holder's orders. |
| Order Status | When did Tempus receive Dwayne Holder's normal sample? | Tempus received Dwayne Holder's normal sample on Jul. 21st, 2019. | Tempus has not yet received Dwayne Holder's normal sample. | Please check the Tempus portal for information regarding Dwayne Holder's orders. |
| Order Status | When was Dwayne Holder's DNA panel ordered? | Dwayne Holder's DNA panel was ordered on Jul. 16th, 2019. | Tempus has not received a DNA order for Dwayne Holder. | Please check the Tempus portal for information regarding Dwayne Holder's DNA orders. |
| Clinical Reports 101 | What type of database does Tempus use for its clinical science information? | Tempus uses a database called the "Knowledge Database," or KDB, to store its clinical science information. | | Could you repeat your question? |
| Clinical Reports 101 | How does Tempus classify variants? | Tempus has adapted standards from the ACMG, AMP, ASCO and other working-groups to use for somatic and germline variant classification, in addition to Tempus uses a weighted classification scheme for classifying variants. Molecular Platform is a proprietary internally-built program that utilizes a series of algorithms that incorporate internal and external | | Could you repeat your question? |

TABLE 2-continued

| Category | Question | Answer | Answer for negative | Answer for Null |
|---|---|---|---|---|
| | | databases and the latest science to classify variants. | | |
| Clinical Reports 101 | What variants does Tempus list on its reports? | Tempus lists pathogenic, likely pathogenic, and variants of unknown significance on its reports. | | Could you repeat your question? |
| Clinical Reports 101 | What groups are variants classified under? | Variants are classified as pathogenic, likely pathogenic, variant of unknown significance, likely benign, or benign variants. | | Could you repeat your question? |
| Clinical Reports 101 | Does Tempus include therapies for VUS"? | Tempus includes therapies for pathogenic and likely pathogenic variants only. | | Could you repeat your question? |
| Clinical Reports 101 | Does Tempus include therapies for likely pathogenic variants? | Tempus does include therapies on its clinical reports for likely pathogenic variants. | | Could you repeat your question? |
| Clinical Reports 101 | What genes are listed under biologically relevant? | Somatic pathogenic and likely pathogenic variants without therapies are "Biologically Relevant." | | Could you repeat your question? |
| Clinical Reports 101 | How does Tempus classify a gene as "Biologically Relevant"? | Tempus classifies somatic pathogenic and likely pathogenic variants without associated therapies as "Biologically Relevant." | | Could you repeat your question? |
| Clinical Reports 101 | Are germline mutations reported for all patients? | Germline mutations are reported for for tumor-normal consenting patients. | | Could you repeat your question? |
| Clinical Reports 101 | Can germline mutations be reported for patients that did not have a normal sample? | Germline mutations are only reported for for tumor-normal consenting patients. | | Could you repeat your question? |
| Clinical Reports 101 | What is the benefit of a tumor normal sample? | Tumor-normal samples allows for clearly defines somatic mutations and can detect medically actionable germline variants. | | Could you repeat your question? |
| Clinical Reports 101 | How can Tempus distinguish from a somatic or germline mutation? | A tumor-normal sample allows for clearly defines somatic mutations and can detect medically actionable germline variants. | | Could you repeat your question? |
| Clinical Reports 102 | Does Tempus report on incidental germline findings? | In addition to somatic variants, Tempus reports Incidental Germline Variants with patient consent. These are inherited variants in genes that have been previously associated with an | | Could you repeat the type of mutation? |

TABLE 2-continued

| Category | Question | Answer | Answer for negative | Answer for Null |
|---|---|---|---|---|
| | | increased risk for certain types of cancer, or other medically actionable disorders recommended by the American College of Medical Genetics and Genomics. | | |
| Clinical Reports 103 | How does Tempus calculate TMB? | TMB is calculated as the number of all protein-altering mutations per million base-pairs of DNA covered by the Tempus panel. For example, non-synonymous mutations are normalized to 2.4 Mb, the size of the xT panel. | | Could you repeat your question? |
| Clinical Reports 103 | How does Tempus calculate MSI? | Tempus measures MSI status through DNA sequencing and also offers clinical MMR protein IHC. | | Could you repeat your question? |
| Clinical Reports 101 | What does Levels of Evidence mean on a Tempus report? | The clinical evidence on a Tempus report integrates clinical expertise, patient medical information, and the best available peer-reviewed evidence, including publications, case studies, guidelines, and others into the decision making process for patient care. | | Could you repeat your question? |
| Clinical Reports 101 | What does "Consensus" mean on a Tempus report? | Consensus evidence on a Tempus report refers to NCCN guideline and/or standard of care. | | Could you repeat your question? |
| Clinical Reports 101 | What types of levels of evidence are used on a Tempus report? | The levels of evidence on a Tempus report include Consensus, Clinical Research, Case Study, and PreClinical evidence. | | Could you repeat your question? |
| Clinical Reports 101 | What does "Case Study" mean on a Tempus report? | Case Study evidence on a Tempus report refers to a case study or small patient cohort. | | Could you repeat your question? |
| Clinical Reports 101 | What does "Preclinical" mean on a Tempus report? | PreClinical evidence on a Tempus report refers to patient-derived xenograft modeling, cell lines, mouse models, or organoid modeling studies. | | Could you repeat your question? |
| Clinical Reports 101 | What does Immune Infiltration mean on a | The immune infiltration estimate on a Tempus report is meant for | | Could you repeat your question? |

TABLE 2-continued

| Category | Question | Answer | Answer for negative | Answer for Null |
|---|---|---|---|---|
| | Tempus report? | experienced physicians to have a starting point to examine the tumor-immune microenvironment. It estimates the proportions between B-, CD4+ T-, CD8+ T-, macrophages, and NK cells in the immune cell infiltrate and does not currently consider any other type of immune cell. This information is only for research use. | | |
| Clinical Reports 101 | What is Immune Infiltration of a tumor? | Immune cells that infiltrate into the tumor can affect the response to immunotherapy. The immune infiltration module uses the gene expression patterns of different immune cell types to predict their relative abundance within the tumor. Higher levels of infiltrating immune cells, specifically cytotoxic CD8+ T cells, are associated with better responses to checkpoint inhibition. | | Could you repeat your question? |
| Clinical Reports 101 | What does HLA typing mean? | HLA typing provides a patient's genotype for the three HLA class 1 genes. There are thousands of different alleles for each HLA gene, and each allele displays a different subset of peptides to the immune system. | | Could you repeat your question? |
| Clinical Reports 101 | What does Neoantigen prediction mean on a Tempus report? | Neoantigen prediction module leverages HLA typing to provide additional context for the results of the TMB metric. Neoantigenic mutations are mutations resulting in a protein change in which from the resulting peptide fragment is predicted to bind to the patient's unique combination of HLA alleles. These mutations are more likely to be visible to the immune system and to be the target of immune responses. | | Could you repeat your question? |

TABLE 2-continued

| Category | Question | Answer | Answer for negative | Answer for Null |
|---|---|---|---|---|
| Clinical Reports 101 | What is immunotherapy resistance risk? | Immunotherapy resistance risk refers to certain gene alterations that have been associated with resistance to immunotherapy regimens. | | Could you repeat your question? |
| Clinical Reports 101 | What is a variant allele fraction? | A Variant Allele Fraction is the proportion of variant reads for a given mutation. This represents the percentage of tumor cells that harbor a specific mutation. | | Could you repeat the term? |
| Clinical Reports 101 | What does potentially actionable mean on a Tempus report? | Potentially actionable on a Tempus report refers to protein-altering variants with an associated therapy. | | Could you repeat the term? |

Thus, the invention is to cover all modifications, equivalents, and alternatives falling within the spirit and scope of the invention as defined by the following appended claims.

To apprise the public of the scope of this invention, the following claims are made:

What is claimed is:

1. A method of providing responses to a user based on user queries about a specific patient's molecular report information, the method for use with a collaboration device that includes a processor, the method comprising:
   (i) storing molecular report information for a plurality of patients in a system database;
   (ii) receiving a query answerable in part by reference to a genomic biomarker from the user;
   (iii) identifying at least one intent associated with the query, the at least one intent including at least one qualifying entity, the at least one intent identified by a machine learning module recognizing the query as sufficiently corresponding to an intent phrase provided to or generated by the machine learning module;
   (iv) identifying at least one parameter value associated with the entity in the query corresponding to the at least one qualifying entity;
   (v) identifying at least one first data operation associated with the at least one intent, the at least one first data operation associated with the at least one qualifying entity;
   (vi) identifying at least one second data operation associated with the genomic biomarker;
   (vii) executing (a) at least one of the identified at least one first data operations and (b) at least one of the identified at least one second data operations on a first set of data in the system database, the first set of data comprising a genomic biomarker from the specific patient's molecular report information, to generate a first set of response data;
   (viii) using the first set of response data to generate a response; and
   (ix) providing the response.

2. The method of claim 1, wherein the collaboration device includes a speaker linked to the processor, wherein generating a response comprises generating an audio response file, and wherein providing the response comprises broadcasting the audio response file via the speaker.

3. The method of claim 1 wherein at least one of the qualifying parameter values includes a patient identity.

4. The method of claim 1 wherein at least one of the qualifying parameter values includes a patient's disease state.

5. The method of claim 1 wherein at least one of the qualifying parameter values includes a genetic mutation.

6. The method of claim 1 wherein at least one of the qualifying parameter values includes a procedure type.

7. The method of claim 1 further including the step of storing a general knowledge database in the system database that includes non-patient specific data about specific topics, wherein the first data operation is associated with the specific patient's molecular report information and the second data operation is associated with the general knowledge database.

8. The method of claim 7 wherein the second data operation associated with the general knowledge database is executed first to generate second data operation results, the second data operation results are used to define the first data operation and the first data operation associated with the specific patient's molecular report information is executed second to generate the first set of response data.

9. The method of claim 7 wherein the first data operation associated with the specific patient's molecular report information is executed first to generate first data operation results, the first data operation results are used to define the second data operation and the second data operation associated with the general knowledge database is executed second to generate the first set of response data.

10. The method of claim 1 wherein the step of identifying at least one intent includes determining that the query is associated with the specific patient, accessing the specific patient's molecular report information, determining the specific patient's cancer state from the molecular report information and then selecting an intent from a pool of cancer state related intents.

11. The method of claim 10 further including the step of storing a general knowledge database in the system database that includes non-patient specific data about specific topics, the method further including the steps of, upon determining that the query is not associated with any specific patient, selecting an intent that is associated with the general knowledge database.

12. The method of claim 1 wherein the collaboration device includes a portable wireless device that includes a wireless transceiver.

13. The method of claim 12 wherein the collaboration device is a handheld device.

14. The method of claim 12 wherein the collaboration device includes at least one visual indicator, the processor linked to the visual indicator and controllable to change at least some aspect of the appearance of the visual indicator to indicate different states of the collaboration device.

15. The method of claim 1, wherein the collaboration device includes a microphone, and wherein receiving a query comprises receiving an audible query via the microphone.

16. The method of claim 15 wherein the processor is programmed to monitor microphone input to identify a "wake up" phrase, the processor monitoring for the audible query after the wake up phrase is detected.

17. The method of claim 15 wherein a series of audible queries are received via the microphone, the at least one of the identified first data operations including identifying a subset of data that is usable with subsequent queries to identify intents associated with the subsequent queries.

18. The method of claim 15 further including the steps of, based on at least one audible query received via the microphone and related data in a system database, identifying at least one activity that a collaboration device user may want to perform and initiating the at least one activity.

19. The method of claim 18 wherein the step of initiating the at least one activity includes generating a second response and broadcasting the second response to the user seeking verification that the at least one activity should be performed and monitoring the microphone for an affirmative response and, upon receiving an affirmative response, initiating the at least one activity.

20. The method of claim 18, wherein the at least one activity includes periodically capturing health information from electronic health records included in the system database.

21. The method of claim 18 wherein the at least one activity includes checking status of an existing clinical or lab order.

22. The method of claim 18, wherein the at least one activity includes ordering a new clinical or lab order.

23. The method of claim 1, wherein the collaboration device is one of a smartphone, a tablet computer, a laptop computer, a desktop computer, or an Amazon Echo.

24. The method of claim 18 wherein the step of initiating the at least one activity includes automatically initiating the at least one activity without any initiating input from the user.

25. The method of claim 1 further including storing and maintaining a general cancer knowledge database, persistently updating the specific patient's molecular report information, automatically identifying at least one intent and associated data operation related to the general cancer knowledge database based on the specific patient's molecular report information, persistently executing the associated data operation on the general cancer knowledge database to generate a new set of response data not previously generated and, upon generating a new set of response data, using the new set of response data to generate another response and broadcasting the another response.

26. The method of claim 1 also for use with an electronic health records system that maintains health records associated with a plurality of patients including the specific patient, the method further including identifying a third data operation associated with the at least one intent and executing the third data operation on the specific patient's health record to generate additional response data.

27. The method of claim 26 wherein the step of using the first set of response data to generate a response includes using the first set of response data and the additional response data to generate the response.

28. A method of providing responses to a user based on user queries about a specific patient's molecular report information, the method for use with a collaboration device that includes a processor, the method comprising:
(i) storing separate molecular report information for each of a plurality of patients in a system database;
(ii) storing a general cancer knowledge database that includes non-patient specific data about cancer topics;
(iii) receiving a query answerable in part by reference to a genomic biomarker from the user;
(iv) identifying at least one intent associated with the query, the at least one intent including at least one qualifying entity, the at least one intent identified by a machine learning module recognizing the query as sufficiently corresponding to an intent phrase provided to or generated by the machine learning module;
(v) identifying at least one parameter value associated with the entity in the query corresponding to the at least one qualifying entity;
(vi) identifying at least a first data operation associated with the at least one intent, the at least one first data operation associated with the at least one qualifying entity and the specific patient's molecular report information;
(vii) identifying at least a second data operation associated with the at least one intent, the at least one second data operation associated with the at least one qualifying entity and the general cancer knowledge database;
(viii) identifying at least one third data operation associated with the genomic biomarker;
(ix) executing the at least a first data operation and at least one of the at least one third data operations on a first set of data in the system database, the first set of data comprising a genomic biomarker from the specific patient's molecular report information, to generate a first set of response data;
(x) executing the at least a second data operation and at least one of the at least one third data operations on the general cancer knowledge database, the general cancer knowledge database comprising genomic alteration knowledge, to generate a second set of response data;
(xi) using at least one of the first and second sets of response data to generate a response; and
(xii) providing the response.

29. A method of audibly broadcasting responses to a user based on user queries about a specific patient's molecular report information, the method for use with a collaboration device that includes a processor and a speaker linked to the processor, the method comprising:

(i) storing molecular report information for a plurality of patients in a system database;
(ii) receiving a query answerable in part by reference to a genomic biomarker from the user;
(iii) determining that the query is associated with the specific patient;
(iv) accessing the specific patient's molecular report information;
(v) determining the specific patient's cancer state from the molecular report information;
(vi) identifying at least one intent from a pool of intents related to the specific patient's cancer state and the query, the at least one intent including at least qualifying entity, the at least one intent identified by a machine learning module recognizing the query as sufficiently corresponding to an intent phrase provided to or generated by the machine learning module;
(vii) identifying at least one parameter value associated with the entity in the query corresponding to the at least one qualifying entity;
(viii) identifying at least one first data operation associated with the at least one intent, the at least one first data operation associated with the at least one qualifying entity;
(ix) identifying at least one second data operation associated with the genomic biomarker;
(x) executing (a) at least one of the identified at least one first data operations and (b) at least one of the identified at least one second data operations on a first set of data in the system database, the first set of data comprising a genomic biomarker from the specific patient's molecular report information, to generate a first set of response data;
(xi) using the first set of response data to generate an audible response file; and
(xii) broadcasting the audible response file via the speaker.

30. A method of providing responses to a user based on user queries about a patient, the method for use with a collaboration device that includes a processor and a microphone linked to the processor, the method comprising:
(i) storing health record information for a plurality of patients in a system database and storing a general cancer knowledge database;
(ii) receiving an audible query answerable in part by reference to a genomic biomarker from the user via the microphone;
(iii) identifying a specific patient associated with the audible query;
(iv) accessing the health record information for the specific patient;
(v) identifying cancer related data in the specific patient's health record information;
(vi) identifying at least one intent related to the identified cancer related data, the at least one intent including at least one qualifying entity, the at least one intent identified by a machine learning module recognizing the audible query as sufficiently corresponding to an intent phrase provided to or generated by the machine learning module;
(vii) identifying at least one parameter value associated with the entity in the cancer related data corresponding to the at least one qualifying entity;
(viii) identifying at least one first data operation related to the at least one intent, the at least one first data operation associated with the at least one qualifying entity;
(ix) identifying at least one second data operation associated with the genomic biomarker;
(x) executing (a) at least one of the at least one first data operations and (b) at least one of the at least one second data operations on the general cancer knowledge database, the general cancer knowledge database comprising genomic biomarker knowledge, to generate a first set of response data;
(xi) using the first set of response data to generate a response; and
(xii) providing the response.

* * * * *